(12) United States Patent
Landegren et al.

(10) Patent No.: US 10,597,701 B2
(45) Date of Patent: Mar. 24, 2020

(54) UNFOLDING PROXIMITY PROBES AND METHODS FOR THE USE THEREOF

(71) Applicant: Olink Bioscience AB, Uppsala (SE)

(72) Inventors: Ulf Landegren, Uppsala (SE); Rachel Yuan Nong, Uppsala (SE); Ola Söderberg, Österbybruk (SE); Irene Helbing, Heidelberg (DE)

(73) Assignee: NAVINCI DIAGNOSTICS AB, Uppsala (SE)

( * ) Notice: Subject to any disclaimer, the term of this patent is extended or adjusted under 35 U.S.C. 154(b) by 285 days.

(21) Appl. No.: 15/374,135

(22) Filed: Dec. 9, 2016

(65) Prior Publication Data

US 2017/0211133 A1 Jul. 27, 2017
US 2017/0362643 A9 Dec. 21, 2017

Related U.S. Application Data

(62) Division of application No. 14/116,706, filed as application No. PCT/EP2012/058841 on May 11, 2012, now Pat. No. 9,551,032.

(30) Foreign Application Priority Data

May 11, 2011 (GB) .................................. 1107863.1

(51) Int. Cl.
| C12Q 1/68 | (2018.01) |
| C07H 21/00 | (2006.01) |
| C12Q 1/6816 | (2018.01) |
| C12Q 1/6841 | (2018.01) |
| C12Q 1/6876 | (2018.01) |

(52) U.S. Cl.
CPC ......... *C12Q 1/6816* (2013.01); *C12Q 1/6841* (2013.01); *C12Q 1/6876* (2013.01)

(58) Field of Classification Search
CPC ..... C12Q 1/68; C12Q 2525/301; C07H 21/00
See application file for complete search history.

(56) References Cited

U.S. PATENT DOCUMENTS

| 5,424,413 | A | * | 6/1995 | Hogan ................ C12N 15/1068 |
| | | | | 435/6.1 |
| 6,194,149 | B1 | | 2/2001 | Neri et al. |
| 6,511,809 | B2 | | 1/2003 | Baez et al. |
| 6,558,928 | B1 | | 5/2003 | Landegren |
| 6,573,051 | B2 | | 6/2003 | Alsmadi et al. |
| 6,867,028 | B2 | | 3/2005 | Janulaitis et al. |
| 6,878,515 | B1 | | 4/2005 | Landegren |
| 7,074,564 | B2 | | 7/2006 | Landegren |
| 7,081,336 | B2 | | 7/2006 | Bao et al. |
| 7,306,904 | B2 | | 12/2007 | Landegren et al. |
| 7,320,860 | B2 | | 1/2008 | Landegren et al. |
| 8,828,661 | B2 | | 9/2014 | Lucero |

| 9,090,934 | B2 | 7/2015 | Lucero et al. |
| 2004/0248103 | A1 | 12/2004 | Feaver et al. |
| 2007/0026430 | A1 | 2/2007 | Anderson et al. |

FOREIGN PATENT DOCUMENTS

| WO | 97/00446 A1 | 1/1997 |
| WO | 01/61037 A1 | 8/2001 |
| WO | 03/012119 A2 | 2/2003 |
| WO | 03/044231 A1 | 5/2003 |
| WO | 2004/029489 A1 | 4/2004 |
| WO | 2004/094456 A2 | 11/2004 |
| WO | 2005/123963 A2 | 12/2005 |
| WO | 2006071582 A2 | 7/2006 |
| WO | 2006/108422 A2 | 10/2006 |
| WO | 2007/005649 A2 | 1/2007 |
| WO | 2007/019492 A2 | 2/2007 |
| WO | 2007/044903 A2 | 4/2007 |
| WO | 2007/054515 A1 | 5/2007 |
| WO | 2007/107743 A1 | 9/2007 |
| WO | 2009/012220 A2 | 1/2009 |
| WO | 2009/037659 A2 | 3/2009 |

OTHER PUBLICATIONS

Fredriksson et al, Nature Biotechnology, 20:473-477 (2002).
Söderberg et al, Nature Methods, 3(12):995-1000 (2006).
Söderberg et al, Methods: A Companion to Methods in Enzymology, 45(3):227-232 (2008).
Weibrecht et al, New Biotechnology, 29(5):589-598 (Aug. 31, 2011).
Nong, Acta Universitatis Upsaliensis, http://uu.diva-portal.org/smash/get/diva2:441225/FULLTEXT01, dated Oct. 7, 2011.
Dean et al, Rapid Amplification of Plasmid and Phage DNA Using Phi29 DNA Polymerase and Multiply-Primed Rolling Circle Amplification, Genome Research, vol. 11, pp. 1095-1099, (2001).
Fredriksson et al, Protein detection using proximity-dependent DNA ligation assays, Nature Biotechnology, vol. 20, pp. 473-477, May 2002.

(Continued)

*Primary Examiner* — Ethan C Whisenant
(74) *Attorney, Agent, or Firm* — Porter Wright Morris & Arthur LLP

(57) ABSTRACT

The present invention relates to a proximity-probe based detection assay for detecting an analyte in a sample and in particular to a method that comprises the use of at least one set of at least first and second proximity probes, which probes each comprise an analyte-binding domain and a nucleic acid domain and can simultaneously bind to the analyte directly or indirectly, wherein the nucleic acid domain of at least one of said proximity probes comprises a hairpin structure that can be unfolded by cleavage of the nucleic acid domain to generate at least one ligatable free end or region of complementarity to another nucleic acid molecule in said sample, wherein when the probes bind to said analyte unfolding said hairpin structure allows the nucleic acid domains of said at least first and second proximity probes to interact directly or indirectly.

10 Claims, 26 Drawing Sheets

Specification includes a Sequence Listing.

(56) References Cited

OTHER PUBLICATIONS

Gullberg et al, Cytokine detection by antibody-based proximity ligation, PNAS, vol. 101, No. 22, pp. 8420-8424, Jun. 1, 2004.

Landegren et al, Molecular tools for a molecular medicine: analyzing genes, transcripts and proteins using padlock and proximity probes, Journal of Molecular Recognition, vol. 17, pp. 194-197, (2004).

Soderberg et al, Direct observation of individual endogenous protein complexes in situ by proximity ligation, Nature Methods, vol. 3, No. 12, pp. 995-1000, Dec. 2006.

Ericsson et al, A dual-tag microarray platform for high-performance nucleic acid and protein analyses, Nucleic Acids Research, vol. 36, No. 8, e-45, pp. 1-9, Mar. 16, 2008 (online).

Soderberg et al, Characterizing proteins and their interactions in cells and tissues using the in situ proximity ligation assay, Methods, vol. 45(3), pp. 227-232, (2008).

Weibrecht et al, Simultaneous Visualization of Both Signaling Cascade Acitvity and End-Point Gene Expression in Single Cells, Plos ONE, vol. 6, Issue 5, e-20148, pp. 1-8, May 25, 2011 (online).

Nong, Proximity Ligation Assays for Disease Biomarkers Analysis, Digital Comprehensive Summaries of Uppsala Dissertations from the Faculty of Medicine 703, pp. 1-43, (Oct. 7, 2011).

Weibrecht et al, Visualising individual sequence-specific protein-DNA interactions in situ, New Biotechnology, vol. 29, No. 5, pp. 589-598, Jun. 2012 (online Aug. 31, 2011).

Official Action from corresponding European Application No. 12720203.4, dated Feb. 3, 2016.

Jenny Goransson et al., PLoS ONE, Journal Article, (2012), pp. 1-9, vol. 7(2).

Ulf Landegren et al., Comparative & Functional Genomics, Journal Article, (2003), pp. 525-530, vol. 4.

Ulf Landegren et al., J. Mol. Cognition, Journal Article, (2004), pp. 194-197, vol. 17.

Martin Lundberg et al., Nucleic Acids Res., Journal Article, (2011), pp. 108, vol. 39(15).

Weibrecht I. et al., Expert Rev. Proteomics, (2010), pp. 401-409, vol. 7(3).

Olink Bioscience, Proseek Multiplex User Manual, (2015), pp. 1-19.

Tyagi et al., Multicolor molecular beacons for allele discrimination, Nature Biotechnology 16:49 (1998).

Simon Fredriksson et al., Nature Biotechnology, Journal Article, (2000), pp. 473-477, vol. 20.

\* cited by examiner

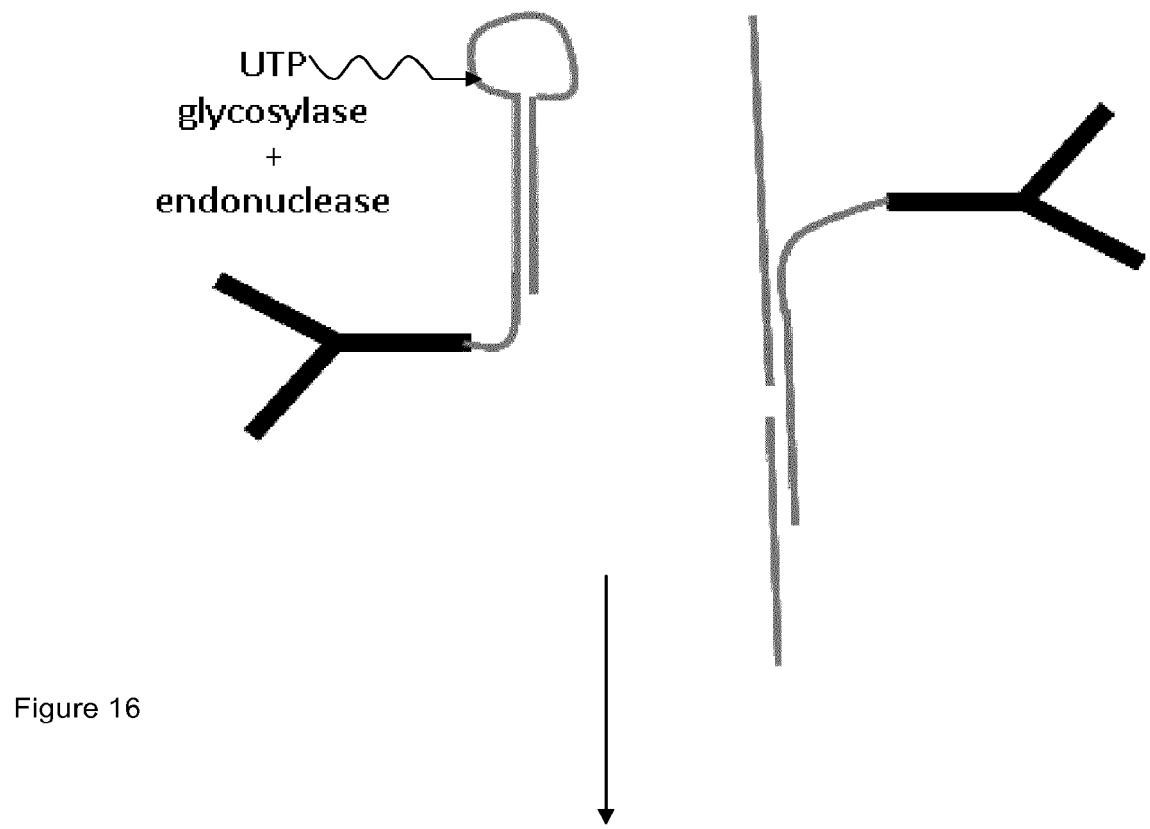
Figure 16
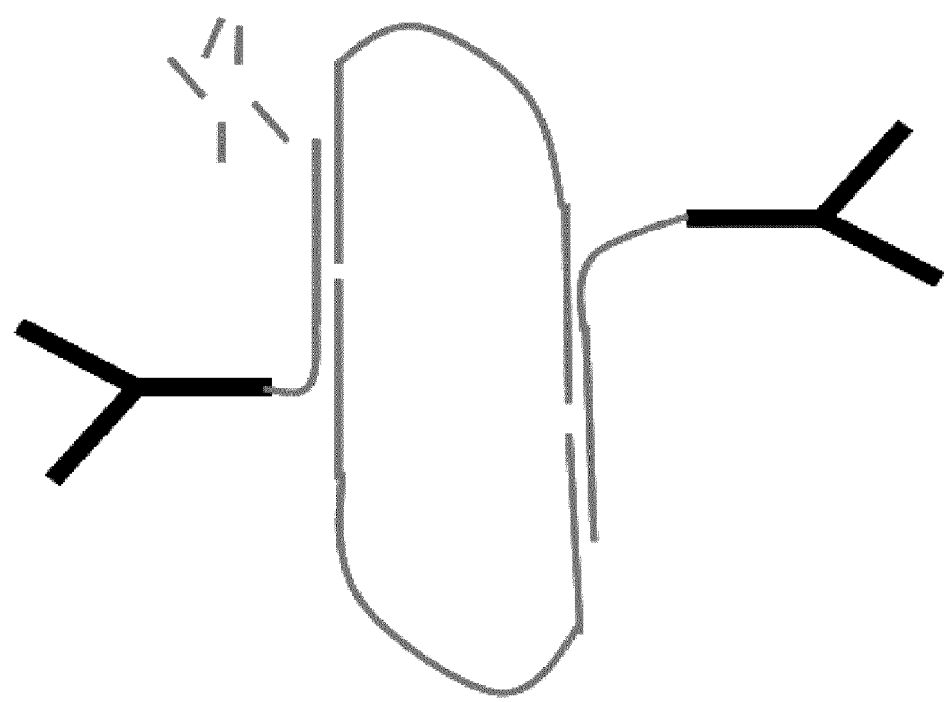

A

B

C a) Probing mRNA/DNA
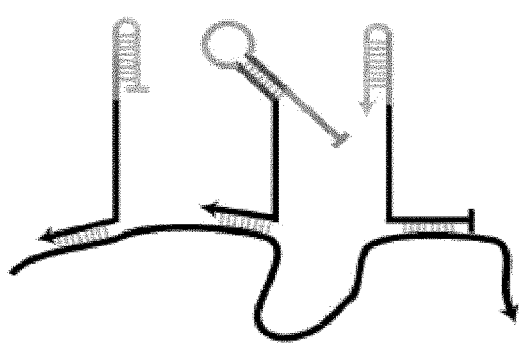
b) Proximity probes unfolding
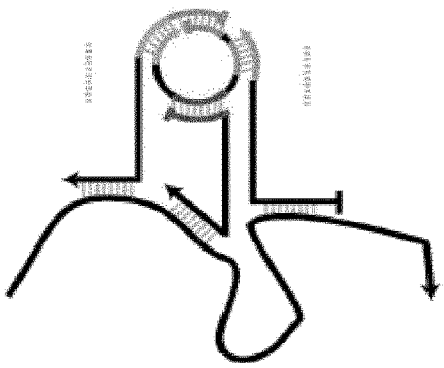
c) Reporter DNA ligating
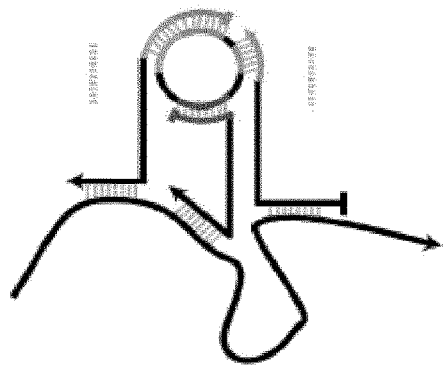
d) RCA and detection *in situ*
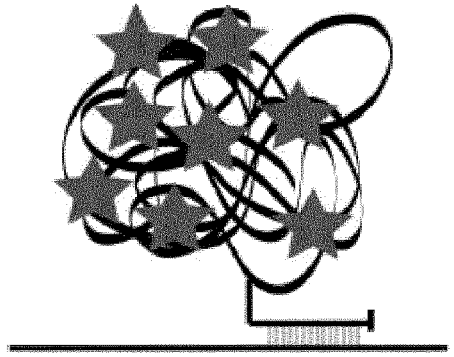
Figure 24
e) Probing protein
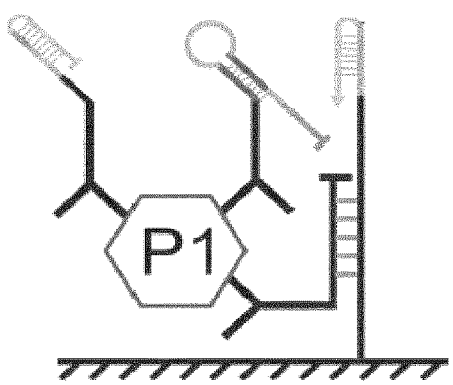
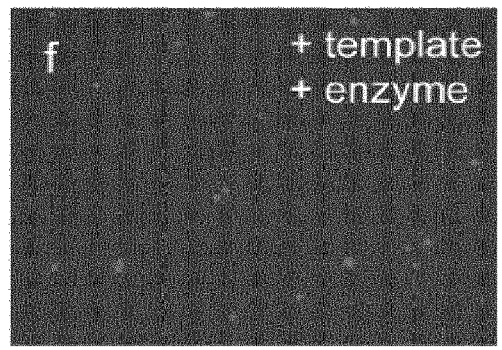
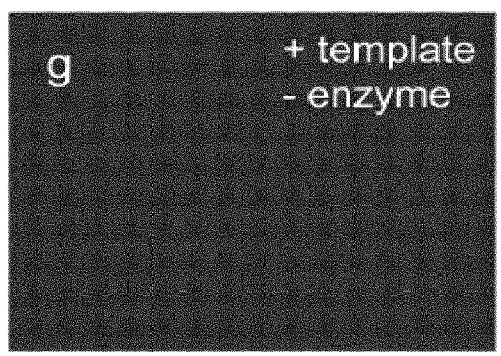
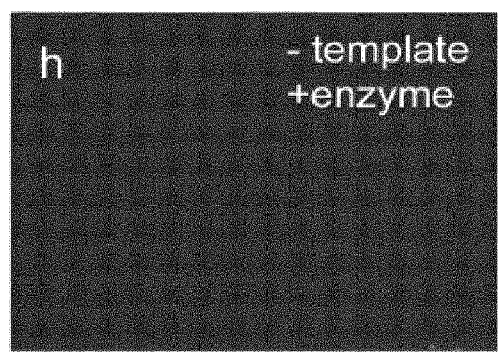

UNFOLDING PROXIMITY PROBES AND METHODS FOR THE USE THEREOF

SEQUENCE LISTING

The specification incorporates by reference the Sequence Listing filed herewith named "EP2012-058841-Sequence-Listing_ST25.txt." created Nov. 8, 2013 and having a size of 7863 bytes.

The present invention relates to a proximity-probe based detection assay ("proximity assay"), principally a proximity ligation assay, for an analyte in a sample. The invention relates particularly to an improvement in the method to reduce non-specific "background" signals, which arise in complex biological samples, and to simplify the assay. The improvement comprises the provision of one or more modified "unfolding" proximity probes for use in such assays, wherein at least part of the "reactive" or "functional" element of a nucleic acid domain of the one or more proximity probes is protected (shielded or masked) from interacting with other nucleic acid molecules when it is contacted with the sample comprising the analyte. The unfolding proximity probes are designed such that the nucleic acid domain of at least one proximity probe of the assay comprises one or more hairpin-loops such that at least part of the reactive (functional) element of the nucleic acid domain is prevented from interacting with other nucleic acid molecules. Once the analyte-binding domain of the proximity probes has been allowed to interact with the analyte (i.e. upon coincident analyte binding), the "protection" may be removed from the nucleic acid domain by "unfolding" the hairpin structure, enabling the reactive element of the nucleic acid domain to interact with other nucleic acid domains/molecules in the sample in a proximity dependent manner. The reactive (functional) element of the nucleic acid domain of at least one proximity probe in the reaction may be unfolded by a cleavage reaction to generate at least one free end or region of complementarity to another nucleic acid molecule in said sample that is capable of interacting with other nucleic acid domains/molecules in the sample.

Thus, in the present invention the effect of the unfolding proximity probes is to prevent probes added to a detection reaction from interacting with each other, despite having complementary sequence elements, i.e. nucleic acid domains that are capable of interaction. Therefore the proximity probes are able to interact with their target molecules (i.e. analyte) independently of each other, and the reactive elements of the nucleic acid domains (e.g. regions of complementarity) are displayed and allowed to interact only after unfolding. The unfolding mechanism also ensures that "new" reactive elements of the nucleic acid domains of the proximity probes are presented during the reaction. It is the "new" reactive elements (i.e. the previously shielded elements) that are capable of participating in ligation or extension reactions, e.g. as ligation or amplification templates or as the nucleic acid molecules that are ligated or extended. The unfolding mechanism can also achieve a reduction in the number of non-specific interactions (e.g. mis-pairings) between the nucleic acid molecules, e.g. nucleic acid domains of the proximity probes or other molecules present in the sample. Hence, the observable effect is thereby an increase in the specificity, sensitivity and efficiency of the assay. The present invention also provides certain unfolding proximity probes and a kit comprising said unfolding proximity probes for use in proximity assays, particularly proximity ligation and proximity extension assays.

A proximity assay relies on the principle of "proximity probing", wherein an analyte is detected by the coincident binding of multiple (i.e. two or more, generally two, three or four) probes, which when brought into proximity by binding to the analyte (hence "proximity probes") allow a signal to be generated. Typically, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when both the necessary two (or more) probes have bound to the analyte, thereby lending improved specificity to the detection system. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity assays.

Thus, in a proximity assay proximity probes may be used, which bind to the analyte and have nucleic acid domains, or moieties, which interact in a proximity-dependent manner upon said analyte binding, generally resulting the ligation of at least one, and preferably two or more, nucleic acid molecules, to form a detectable, preferably amplifiable, nucleic acid detection product by means of which said analyte may be detected.

Proximity-probe based detection assays, and particularly proximity ligation assays permit the sensitive, rapid and convenient detection or quantification of one or more analytes in a sample by converting the presence of such an analyte into a readily detectable or quantifiable nucleic acid-based signal, and can be performed in homogeneous or heterogeneous formats.

Proximity probes of the art are generally used in pairs, and individually consist of an analyte-binding domain with specificity to the target analyte, and a functional domain, e.g. a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the same analyte molecule (which may be a complex of interacting molecules), i.e. upon coincident binding of the probes to the target analyte, the functional domains (e.g. nucleic acid domains) are able to interact, directly or indirectly. For example, nucleic acid domains may be joined to form a new nucleic acid sequence generally by means of a ligation reaction, which may be templated by a splint oligonucleotide added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by realtime quantitative PCR (q-PCR).

Alternatively, rather than being ligated to each other, the nucleic acid domains of the proximity probes when in proximity may template the ligation of one or more added oligonucleotides to each other (which may be the nucleic acid domain of one or more proximity probes), including an intramolecular ligation to circularise an added linear oligonucleotide, for example based on the so-called padlock probe principle, wherein analogously to a padlock probe, the ends of the added linear oligonucleotide are brought into juxtaposition for ligation by hybridising to a template, here a nucleic acid domain of the proximity probe (in the case of a padlock probe the target nucleic acid for the probe). Various such assay formats are described in WO 01/61037.

WO 97/00446 and U.S. Pat. No. 6,511,809 disclose a heterogeneous format for proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101: 8420-8424.

Although pairs of proximity probes are generally used, modifications of the proximity-probe detection assay have been described, in e.g. WO 01/61037 and WO 2005/123963, where three proximity probes are used to detect a single analyte molecule, the nucleic acid domain of the third probe possessing two free ends which can be joined (ligated) to the respective free ends of the nucleic acid domains of the first and second probes, such that it becomes sandwiched between them. In this embodiment, two species of splint oligonucleotide are required to template ligation of each of the first and second probes' nucleic acid domains to that of the third.

In a further modification described in WO 2007/107743 the splint oligonucleotide to template ligation of the nucleic acid domains of two proximity probes is carried on a third proximity probe.

Not all proximity assays are based on ligation. WO 2007/044903 discloses proximity probe-based assays for detecting analytes which rely on the formation and detection of a released nucleic acid cleavage product. Some of the described embodiments involve a probe comprised of an analyte-binding moiety and an attached enzyme, which enzyme acts on a nucleic acid moiety attached to the analyte-binding moiety of a second probe, resulting in the release of a detectable nucleic acid cleavage product.

Analyte detection assays, including in some embodiments proximity probe-like reagents, wherein a polymerase enzyme attached to an analyte-binding moiety of one probe acts on a nucleic acid moiety attached to the analyte-binding moiety of a second probe, are described in WO 2009/012220. In these assays, the action of the "tethered" polymerase which is part of one of the probes of a probe pair results in the generation of a template, free in solution, which is susceptible to amplification by an added polymerase. Unlike the tethered polymerase, the added polymerase is only able to act on the template generated by the tethered polymerase, and not directly on the nucleic acid moiety of the non-polymerase-containing probe of the probe pair. The action of the added polymerase results in amplification of the generated template, the amplified copies being detectable and indicative of the presence of analyte in the sample, according to the proximity probing principle.

In addition to modification to the proximity-probe detection assay, modifications of the structure of the proximity probes themselves have been described, in e.g. WO 03/044231, where multivalent proximity probes are used. Such multivalent proximity probes comprise at least two, but as many as 100, analyte-binding domains conjugated to at least one, and preferably more than one, nucleic acid(s).

Proximity-probe based detection assays and particularly proximity ligation assays, have proved very useful in the specific and sensitive detection of proteins in a number of different applications, e.g. the detection of weakly expressed or low abundance proteins. However, such assays are not without their problems and room for improvement exists, with respect to both the sensitivity and specificity of the assay.

The sensitivity of the conventional proximity assays, e.g. proximity ligation assays, as described above, is limited by two main factors: (i) the affinity of the analyte-binding domains for the target analyte and (ii) the non-specific background signal arising from the random proximity of non-bound probes, particularly probe pairs. Using probes having binding domains with high affinity for the analyte, sensitivity is limited to the detection of approximately 6000 molecules. Traditionally, in order to achieve a low level of background, very low concentrations of proximity probes must be used. This precludes any attempt to compensate for probes comprising low affinity analyte-binding domains by using higher concentrations of probe. It has therefore been found that this may limit the sensitivity of the assay, and the range over which quantitative results may be obtained.

Other methods for reducing non-specific background signal have been proposed, such as coupling the splint (ligation template) oligonucleotide to a third proximity probe and/or using blocking agents such as blocking oligonucleotides, which bind to the free ends of the nucleic acid domains on the proximity probes until displaced by a splint oligonucleotide. Displacement readily occurs only when the proximity probes are bound to the target analyte (WO 2007/107743). Further methods for reducing background signal have centred on the improving the detection of the ligated nucleic acid.

However, there is still room to improve the level of background signal and in order to overcome the limitations of the proximity assay, particularly proximity ligation assays, known in the art. As described above, it has now been found that the use of an unfolding proximity probe significantly improves the sensitivity and specificity of the assay as it allows the reaction to proceed sequentially, i.e. in discrete and/or separable stages. Moreover, in some embodiments the use of such unfolding proximity probes simplifies the assay protocol as it allows all potentially interacting components to be contacted with the sample simultaneously, without their interaction, i.e. the reactive (functional) elements of the nucleic acid domains of the unfolding proximity probes are prevented from interacting due to their hairpin structure. Hence, in the first instance the proximity probes are allowed to interact with the sample such that only the analyte-binding domain of the proximity probes may interact with the analyte in the sample. Following sufficient conditions to allow for binding of the proximity probes to the analyte (i.e. upon coincident binding of the probes to the analyte), the nucleic acid domains of the unfolding proximity probes may be activated, i.e. unfolding the hairpin structure by a cleavage reaction, to release the reactive element of the nucleic acid domains, which may then interact in a proximity dependent manner. By protecting (shielding or masking) the nucleic acid domains of one or more of the proximity probes of the assay from reacting with other nucleic acid molecules or other components in the sample until the probes have bound to the analyte, it is possible to reduce the non-specific background signal present in the assay.

Whilst the use of reagents to block the reactive elements of proximity probes is known in methods used for detecting an analyte in a sample, the use of unfolding proximity probes and nature of the mechanism of the release of folded structure in the present invention provides a unique and unexpected advantage over previously described blocking agents.

The present invention is predicated on the development of an assay for the detection of individual, sequence-specific protein-DNA-interactions. However, it will be evident from the description herein that the unfolding proximity probes of the invention will find utility in numerous proximity probe assays and are not limited to the detection of protein-DNA-interactions. Indeed the methods of the invention may be used for the detection of any analyte in a sample, as defined below.

By way of background, a fundamental aspect of the control of gene expression arises from interactions between proteins and nucleic acid molecule, e.g. transcription factors, histones etc. In the past, such interactions have been studied only in bulk populations of cells by methods such as electrophoretic mobility shift assays and chromatin immunoprecipitation. Whilst such assays provide information about proteins that bind certain DNA sequences, this data provides only a general view of the interactions in said cells. Any interactions that occur only in a minority of cells are not detected in such assays, which generate a signal that is an average from a large number of cells.

It is understood that epigenetic modifications or changes in transcription factor activity play an important role in the control of gene expression. In fact these are hypothesized to be among the initial events transforming a cell into a so-called cancer stem cell (CSC). By studying protein-DNA interactions (PDI), like epigenetic changes, at the genomic DNA level during cancer development, or activation of specific transcription factors when cancer cells undergo epithelial-mesenchymal-transition, markers for CSC and metastatic tumour colonies could be identified. However, as CSCs represent only a fraction of all cells comprising a tumour from a patient biopsy they cannot be identified by bulk analyses averaging over the whole population of cells. Therefore, new methods are needed to enable investigation of PDIs at cellular and subcellular resolution in cells and tissues.

To address this need the inventors have developed a proximity ligation assay capable of detecting such interactions, an example of which is shown in FIG. 1. This figure depicts a representative embodiment of the invention and it will be apparent that many permutations of this assay are possible, based on the use of proximity probes comprising a nucleic acid domain that can be unfolded by cleavage.

Nevertheless, the steps shown in FIG. 1 represent a starting point from which the rest of the invention may be described. In this regard, the assay in FIG. 1 comprises a first proximity probe with a domain capable of binding (directly or indirectly) to the protein of the PDI complex (i.e. the analyte) coupled to a nucleic acid domain capable of interacting with the nucleic acid domain of the second proximity probe. In the specific embodiment shown in FIG. 1, the first proximity probe is an antibody coupled to a nucleic acid domain, wherein the antibody binds the analyte directly, i.e. it binds to the protein of the PDI complex.

The second proximity probe comprises a domain capable of binding (e.g. hybridizing) to the nucleic acid of the PDI complex in proximity to the protein of the PDI complex. The DNA-binding portion of the proximity probe (the analyte-binding domain) is coupled to a nucleic acid domain capable of interacting with the nucleic acid domain of the first proximity probe. However, the nucleic acid domain of the second proximity probe comprises at least one region of self-complementarity such that it forms a stem-loop or hairpin-loop that prevents its interaction with the nucleic acid domain of the first proximity probe. In the specific embodiment shown in FIG. 1, the second proximity probe is a circularisable oligonucleotide, a so-called padlock probe. A padlock probe comprising a region of self-complementarity is also known as a "horn" probe, as defined further below.

The first and second proximity probes are contacted with the sample and the analyte-binding domains (i.e. the proximity probe domains capable of interacting with the PDI complex) are allowed bind specifically to their respective targets. The specificity of the interaction of the second proximity probe with the analyte is confirmed by a first ligation reaction templated by the nucleic acid of the PDI complex to produce a circular oligonucleotide. The stem-loop of the second proximity probe (the so-called horn probe) is then unfolded (by a cleavage reaction) to release two regions of complementarity to the nucleic acid domain of the first proximity probe. The nucleic acid domains the first and second proximity probes are allowed to interact (i.e. hybridize or anneal) and the nucleic acid domain of the first proximity probe acts as a ligation template for the released ligatable ends of the nucleic acid domain of the second proximity probe. The ligatable ends of the nucleic acid domain of the second proximity probe may be ligated in a second ligation reaction to produce a circular oligonucleotide. The ligation reactions (i.e. both the first and second ligation reactions) may be a direct ligation, e.g. if the ends are directly adjacent to each other, or an indirect ligation, e.g. if there is a space between the free ligatable ends a "gap" oligonucleotide may be added to the reaction such that each free end is ligated to the gap oligonucleotide (as shown in FIG. 1). The gap oligonucleotide comprises at least one region of complementarity to the ligation template, in between the ligatable free ends of the nucleic acid domain of the proximity probe. The formation of the circular oligonucleotide may be detected, e.g. by rolling circle amplification (RCA) and hybridisation of labelled probes to the RCA product, thereby detecting the interaction between the two proximity probes. In some embodiments RCA may be primed by the nucleic acid domain of a proximity probe or by the analyte.

It will be seen, therefore, that the use of at least one unfolding proximity probe enables the reaction to proceed in controlled distinct (discrete or separable) stages. In the embodiment described above the stages can be considered as:

(i) binding of the proximity probes to the analyte;
(ii) a first ligation reaction;
(iii) unfolding of the protected proximity probe;
(iv) a second ligation reaction; and
(v) detection of the interaction between the proximity probes.

It will further be seen that the components of the assay may be contacted with the analyte-containing sample simultaneously without interaction of the nucleic acid domains of the proximity probes prior unfolding of the hairpin of the unfolding proximity probes. The combination of these features, i.e. that the reaction may proceed in stages whilst enabling the addition of the interacting components of the assay simultaneously, is particularly advantageous. The methods described herein reduce the complexity of the protocol of the assay whilst also increasing the sensitivity and specificity of proximity probes detection assays. Moreover, it will be evident that the unfolding proximity probes of the invention may be used in any suitable proximity probe assay further to prevent non-specific interaction of proximity probe nucleic acid domains and therefore reduce non-specific background signals.

Accordingly, at its broadest the invention can be seen to provide a method of detecting an analyte in a sample, being a proximity assay, which method comprises the use of at least one set of at least first and second proximity probes, which probes each comprise an analyte-binding domain and a nucleic acid domain and can simultaneously bind to the analyte directly or indirectly, wherein the nucleic acid domain of at least one of said proximity probes comprises a hairpin structure that can be unfolded by cleavage of the nucleic acid domain to generate at least one ligatable free end or region of complementarity to another nucleic acid molecule in said sample, wherein when the probes bind to said analyte unfolding said hairpin structure allows the nucleic acid domains of said at least first and second proximity probes to interact directly or indirectly.

Thus, it will be evident that in a particularly preferred embodiment of the methods of the invention the nucleic acid domains of said first and second proximity probes are, following unfolding, mutually complementary or complementary to a common template.

Thus, the interaction of the nucleic acid domains which is permitted by the unfolding may be hybridisation or ligation of the domains to each other, or hybridisation to a common template (e.g. a ligation template). It will seen therefore that the common template may be a nucleic acid molecule (e.g. oligonucleotide) to which the nucleic acid domains of the proximity probes (i.e. the "interacting" domains) may each hybridise. The common template may thus contain separate, or distinct, binding sites for hybridisation of the nucleic acid domains, such that they may both bind to the same (i.e. "common") molecule (i.e. at the same time).

The method of the invention thus comprises a step of cleaving the nucleic acid domain, to unfold the hairpin structure to generate, or release, at least one ligatable free end or region of complementarity. For example after binding of the probes to the analyte, the nucleic acid domain(s) may be cleaved to unfold the hairpin structure and allow interaction of the nucleic acid domains.

Alternatively viewed, the methods of the invention may be seen as providing a method of increasing the sensitivity and/or specificity of proximity assays. Expressed in another way, the invention may be seen to provide a method for reducing non-specific interactions between proximity probes in proximity assays. In another aspect, the method may be seen as reducing background noise in proximity assays or increasing the background noise to signal ratio in proximity assays.

A further aspect of the invention, as described in detail below, is the provision of unfolding proximity probes, e.g. horn probes, comprising a hairpin structure that can be unfolded by cleavage of the nucleic acid domain, for use in the methods of the invention and proximity assays in general. Notably, such assays will be proximity ligation assays, although this aspect of the invention is not limited to detecting interactions between the nucleic acid domains of proximity probes based on ligation (for example the interaction between the nucleic acid domains may be based on hybridisation, as disclosed for example in WO 97/00446 or WO 01/61037).

Rolling circle amplification using padlock probes (of which a horn probe is a specific type), e.g. as described in U.S. Pat. No. 6,558,928, or indeed any circular nucleic acid molecule as a template can also be used to generate a unique nucleic acid molecule and can be useful in amplifying an existing "signal" nucleic acid molecule (e.g. generated from a proximity probe ligation assay) or in the detection of a specific analyte, e.g. wherein the analyte is a nucleic acid molecule. It will be apparent from the below description that the methods of the application may generate circular oligonucleotides to which rolling circle amplification methods may be applied.

Accordingly, in one preferred aspect the present invention provides a method of detecting an analyte in a sample, comprising:

a) contacting said sample with at least one set of at least first and second proximity probes, which probes each comprise an analyte-binding domain and a nucleic acid domain and can simultaneously bind to the analyte directly or indirectly, wherein the nucleic acid domain of at least the first of said proximity probes comprises a hairpin structure that can be unfolded by cleavage of the nucleic acid domain to generate at least one ligatable free end, wherein when the probes bind to said analyte said at least one ligatable free end is capable of interacting with the nucleic acid domain of said second proximity probe;

(b) directly or indirectly ligating said at least one ligatable free end to the nucleic acid domain of a proximity probe: and (c) detecting said ligation.

The ligation in step (b) may be an intermolecular or intramolecular ligation. Thus, a ligatable free end which is released by cleavage may be ligated to the nucleic acid domain of a different proximity probe, or it may be ligated to the other end of the nucleic acid domain of the same proximity probe (the other end may also be released in the cleavage step, as discussed further below).

An alternative preferred embodiment of the invention provides a method of detecting an analyte in a sample, comprising:

a) contacting said sample with at least one set of at least first and second proximity probes, which probes each comprise an analyte-binding domain and a nucleic acid domain and can simultaneously bind to the analyte directly or indirectly, wherein the nucleic acid domain of at least the first of said proximity probes comprises a hairpin structure that can be unfolded by cleavage of the nucleic acid domain to generate at least one region of complementarity to a nucleic acid molecule in said sample, said at least one region of complementarity being a ligation template which is capable of hybridizing at least to the nucleic acid domain of said second proximity probe, wherein when the probes bind to said analyte the nucleic acid domain of the second proximity probe is ligatable to the nucleic acid domain of a proximity probe by means of an interaction mediated by said hybridised ligation template of said first proximity probe;

(b) directly or indirectly ligating the nucleic acid domain of said second proximity probe with the nucleic acid domain of a proximity probe; and (c) detecting said ligation.

Again the ligation of step (b) may be intra- or intermolecular, i.e. to the nucleic acid domain of the same or a different proximity probe.

A further alternative embodiment of the invention provides a method of detecting an analyte in a sample, comprising:

a) contacting said sample with at least one set of at least first and second proximity probes, which probes each comprise an analyte-binding domain and a nucleic acid domain and can simultaneously bind to the analyte directly or indirectly, wherein the nucleic acid domain of at least the first of said proximity probes comprises a hairpin structure that can be unfolded by cleavage of the nucleic acid domain to generate at least one region of complementarity to a nucleic acid molecule in said sample, said at least one region of complementarity being a primer which is capable of hybridizing directly or indirectly to the nucleic acid domain of said second proximity probe, wherein when the probes bind to said analyte the nucleic acid domain of the second proximity probe is a template for the extension of the nucleic acid domain of said first proximity probe;

(b) extending the nucleic acid domain of said first proximity probe; and (c) detecting said nucleic acid extension product.

Whilst not wishing to be bound by theory, it is believed that the methods of the invention rely upon the hairpin structure in the nucleic acid domains of the unfolding proximity probes to protect (shield or mask) of the reactive element(s) of said nucleic acid domains from interacting with the nucleic acid domains of other proximity probes when not bound to their target site of the analyte. This protective effect is thought to reduce non-specific interactions (i.e. interactions brought about by non-target specific proximity of the probes in the reaction mixture) between the nucleic acid domains of the proximity probes, thereby decreasing the amount of signal produced by non-target specific interactions.

As will be described in more detail below, a particularly preferred aspect of the invention concerns unfolding proximity probes wherein the hairpin structure of the nucleic acid domains is unfolded, preferably by cleavage of the hairpin structure, to release two free ends, a 5' and 3' end, which are both capable of interacting with other nucleic acid molecules in the sample, preferably wherein said nucleic acid molecules are nucleic acid domains of other proximity probes.

For example, in some embodiments, the free ends may hybridise to one or more nucleic acid domains (common template(s)) which act to template the ligation of the free ends to each other to generate a circular oligonucleotide. Such a ligation may be direct, i.e. where the free ends hybridise to the ligation template directly adjacent to each other. Alternatively, the ligation may be indirect, i.e. where the free ends hybridise to the ligation template with a space in between which is filled by a "gap" oligonucleotide such that each free end is ligated to one end of the gap oligonucleotide. In some embodiments, the space in between the free ends may be "filled-in" by extending the free 3' end, e.g. in a polymerase reaction, using the ligation template as an extension template. Once the free 3' end has been extended to be adjacent to the free 5' end, the two ends may be joined by a ligation reaction.

In yet further embodiments, one or both of the two free ends may be ligated to nucleic acid domains of further proximity probes, wherein such ligations are templated by one or more ligation templates (an oligonucleotide which contains a region of complementarity to each end of the nucleic acid domains of the proximity probes). In certain embodiments each free end is ligated to the nucleic acid domain of a different proximity probe. In another embodiment, the two free ends (5' and 3) are ligated to the respective 3' and 5' ends of the nucleic acid domain of a second proximity probe. In such an embodiment, the nucleic acid domains of two proximity probes may each be unfolded to release 5' and 3' ends, allowing the ligation of the respective ends of each of the two domains together to form a circular molecule. The release of the ligatable 5' and 3' ends of the nucleic acid domain of each probe can thus be viewed as the generation of a "half-circle" for circularisation by ligation of the two half-circles together. Such half-circles are known in the art as two parts of a two-part padlock probe. In some embodiments, the ligation template may be a nucleic acid domain of a further proximity probe.

In another embodiment, the "half-circles" of the two-part padlock probe may be provided as oligonucleotides hybridised to the nucleic acid domain of a first proximity probe. Such hybridisation may be before or after contacting the sample with the proximity probes, i.e. the two-part padlock probe may be viewed as part of the nucleic acid domain of the proximity probe or could be viewed as additional oligonucleotides added to the assay. The second proximity probe may be an unfolding proximity probe, wherein the nucleic acid domain comprises a ligation template. Hence, after the proximity probes have bound to the analyte, the second proximity probe may be unfolded, e.g. by cleavage, and two ligation reactions may be templated by the nucleic acid domains of the first and second proximity probes to yield a circular oligonucleotide (see e.g. FIG. 16).

As described above, the invention concerns the use of unfolding proximity probes. In its simplest form, unfolding can be defined as the release of at least part of the hairpin structure of the nucleic acid domain of an unfolding proximity probe to yield at least one ligatable free end or region of complementarity to another nucleic acid molecule. In other words, unfolding results in the opening of the hairpin structure. In some embodiments, the unfolding may be achieved by disruption of at least part of the double stranded element of the hairpin structure. In other embodiments, the double stranded element of the hairpin structure may be retained and the unfolding may be achieved by modifying, e.g. cleaving, the loop of the hairpin structure. In a particularly preferred embodiment, unfolding of a proximity probe results in the release to two free ends, a 5' and 3' end.

It is evident that unfolding may be achieved in a number of ways. Different means of unfolding may be used for different proximity probes used in the method. Whilst it is a requirement of the method of the invention that at least one nucleic acid domain of a proximity probe is unfolded by cleavage it is not required that each domain is unfolded by cleavage. Thus more than one unfolding probe may be used, but it is required that only one is unfolded by cleavage. In one preferred embodiment of the invention, unfolding of each unfolding probe is achieved by cleavage of the nucleic acid domain. In other embodiments at least one domain is unfolded by cleavage and at least one other domain is unfolded by other means. Preferably the site at which cleavage occurs is located in, i.e. forms part of, the hairpin structure of the nucleic acid domain. As discussed below, cleavage is preferably enzymatic cleavage.

As described above, the nucleic acid domains of the unfolding proximity probes of the invention comprise at least one hairpin structure. A hairpin structure may also be known as a hairpin-loop or a stem-loop and these terms are used interchangeably herein. A hairpin is an intramolecular base-pairing pattern that can occur in a single-stranded DNA or RNA molecule. A hairpin occurs when two regions of the same strand, usually complementary in nucleotide sequence when read in opposite directions, base-pair to form a double helix (a duplex) that ends in an unpaired, i.e. single-stranded, loop. The resulting structure can be described as lollipop-shaped.

In a preferred aspect a hairpin does not form the end of the nucleic acid domain of the proximity probe, i.e. the duplex of each hairpin is flanked by single-stranded regions at the 5' and 3' ends of duplex. In an alternative embodiment, a hairpin may be a one end of the nucleic acid domain, i.e. one end of the duplex (the 3' or 5' end) forms the end of the nucleic acid domain.

As mentioned above, unfolding may also be achieved by disrupting at least part of the double stranded element of the hairpin structure. This may be achieved by altering the conditions of the sample such that the hairpin structure is no longer a thermodynamically favourable structure, e.g. by altering the temperature or salt concentrations of the solution. Similarly, the hairpin structure may be destabilised by modification of one or more of the nucleotide bases in the duplex to disrupt the hydrogen bonds (so-called Watson-Crick base pairing) which anneal the two strands. For example, cleavage of the base from the nucleotide may be sufficient to disrupt the duplex enough to "unfold" the hairpin.

Alternatively, the hairpin structure may be unfolded outcompeting the double stranded element of the hairpin structure with "anti-blocking" oligonucleotides. For instance, in the presence of a high concentration of an anti-blocking oligonucleotide that is complementary to one of the strands of the hairpin structure, the interaction (hybridization) between the anti-blocking oligonucleotide and the nucleic acid domain of the proximity probe will be favoured over the hairpin structure. Thus, in the proximity assays of the present invention the "anti-blocking" oligonucleotide may be in the form of the nucleic acid domain of a proximity probe, e.g. a ligation template oligonucleotide or a primer oligonucleotide. It will be apparent that when the proximity probes are all bound to the analyte the nucleic acid domains of said probes are effectively present in a high local concentration. Hence, if the interaction (hybridization) between the nucleic acid domains of the proximity probes is more stable (thermodynamically favourable) than the interaction between the elements of the hairpin structure of the unfolding proximity probe, the hairpin structure will unfold to enable interaction between the nucleic acid domains of the proximity probes.

In some preferred embodiments the proximity assays comprise more than one unfolding proximity probe. In such embodiments it will be evident that the hairpin structure of such unfolding proximity probes may be unfolded in different ways in the same reaction, e.g. the first unfolding proximity probe may be unfolded by cleavage and the second unfolding proximity probe may be unfolded by competition with the nucleic acid domain of another proximity probe. For example, unfolding the first proximity probe may result in a region of complementarity that causes the disruption of a hairpin structure in the second proximity probe.

In other embodiments, one or more unfolding proximity probes may be used in combination with "standard" non-unfolding proximity probes. In preferred embodiments, such standard proximity probes may utilise blocking oligonucleotides (as described further below) to protect (mask or shield) the reactive elements of the nucleic acid domains of said proximity probes, to minimise their interaction with the nucleic acid domains of other proximity probes or other components in the sample.

According to the method of the present invention at least one of the unfolding proximity probes is unfolded by cleavage.

"Cleavage" is defined broadly herein to include any means of breaking or disrupting a nucleotide chain (i.e. a nucleotide sequence). Cleavage may thus involve breaking a covalent bond. This may involve, but does not require, cleavage of nucleotide chain (i.e. strand cleavage or strand scission), for example by cleavage of a phosphodiester bond.

In some embodiments, cleavage of the nucleic acid domain of the unfolding proximity probe concerns breaking at least one covalent bond linking adjacent nucleotide residues of the nucleic acid molecule, e.g. hydrolysis of the phosphodiester bond. Cleavage preferably involves the hydrolysis of one or more phosphodiester bond in one strand of the hairpin structure. Thus, in a particularly preferred embodiment, the hairpin structure comprises a cleavage recognition site, e.g. a sequence that is recognised by one or more enzymes capable of cleaving nucleic acid molecules. Any suitable enzyme may be used to cleave the hairpin structure to unfold the nucleic acid domain of the proximity probe.

For instance, the hairpin structure may comprise or may be engineered or modified to comprise a restriction endonuclease recognition sequence. In a preferred embodiment, e.g. where the hairpin structure comprises a restriction endonuclease recognition site, the restriction endonuclease will cleave only a single strand of the duplex portion of the hairpin structure.

In a preferred aspect, the hairpin structure may be engineered to comprise a restriction endonuclease recognition sequence. For example, this may be achieved by hybridising an oligonucleotide (termed herein a "restriction oligonucleotide") to the single-stranded loop of the hairpin structure to comprise a duplex within the loop. At least part of the formed duplex will comprise a restriction endonuclease recognition site, which can be cleaved resulting in unfolding of the hairpin structure. Any suitable restriction endonuclease may be used to unfold the hairpin structure. In some embodiments, the restriction oligonucleotide may be in the form of a nucleic acid domain of a proximity probe.

In yet further embodiments of the invention an exonuclease enzyme may be used to degrade one strand of the hairpin duplex, thereby releasing the single-stranded loop of the hairpin, i.e. unfolding the probe. The exonuclease enzyme may have 5' or 3' exonuclease activity depending on the orientation of the hairpin structure.

In other embodiments, cleavage may comprise breaking covalent bonds within one or more nucleotides in a nucleic acid sequence. For example, where the hairpin structure comprises uracil residues, at least a portion of the duplex in the hairpin structure may be disrupted by removing one or more uracil bases, i.e. cleavage of said bases from the nucleic acid using a uracil-DNA glycosylase enzyme. Removal of said one or more uracil bases results in the loss of some hydrogen bonds between the two strands of the hairpin duplex, resulting in a loss of stability and unfolding of the nucleic acid domain.

In some embodiments the cleavage recognition site is achieved by generating a nucleic acid domain wherein the hairpin structure comprises one or more Uracil residues. In a particularly preferred embodiment, the hairpin structure can be unfolded by treatment with a uracil-DNA glycosylase (UNG) enzyme in combination with an endonuclease enzyme capable of recognising apurinic/apyrimidinic (AP) sites of dsDNA, e.g. endonuclease IV.

In a further preferred embodiment the hairpin structure may be cleaved, and thereby unfolded, using a nickase enzyme, which cleaves only one strand in the duplex of the hairpin structure. Nickases are endonucleases which cleave only a single strand of a DNA duplex. As described above, a cleavage recognition site may be engineered in the single-stranded loop of the hairpin structure, e.g. by annealing (hybridising) and oligonucleotide to said loop.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is herein incorporated by reference in its entirety and any suitable nickase may be used in the methods of the invention.

In some preferred embodiments that utilise a nickase enzyme, the nickase enzyme is removed from the assay or inactivated following unfolding of the nucleic acid domain of the proximity probe to prevent unwanted cleavage of ligation products.

The detection itself depends upon the presence of an analyte in a sample and detecting the interaction between two (or more) proximity probes, when such probes are bound to the analyte (i.e. upon coincident binding of the proximity probes to the analyte). The interaction between the probes (or more specifically, between their respective nucleic acid domains is thus proximity-dependent; the binding of the proximity probes, together, on the analyte brings them into proximity, such that they (or more particularly, their nucleic acid domains) may interact. Accordingly, by detecting the interaction, for example a ligation reaction (e.g. by detecting a product of the interaction, e.g. the product of the ligation reaction), the analyte may be detected. Thus, in general terms the interaction between the nucleic acid domains of the proximity probes may lead to the generation of a product, typically a nucleic acid product, which may be detected in order to detect the analyte. Accordingly in step (c) of the methods set out above, by detecting said ligation (e.g. by detecting the product of said ligation reaction), the analyte may be detected. Similarly, in embodiments where the detection step involves detecting an extension product, e.g. the extension of a primer templated by the nucleic acid domain of another proximity probe, by detecting the extension product the analyte may be detected.

As noted above, proximity-dependent assays based on ligation represent a preferred embodiment of the invention (i.e. wherein at least first and second proximity probes used in the detection method comprise nucleic acid domains, at least one of which comprises a hairpin structure unfolded by cleavage, and the interaction between them involves a ligation reaction). Viewed generally, the nucleic acid domains of the probes may mediate (e.g. take part in), directly or indirectly, a ligation reaction. Such a ligation reaction may involve ligation of the nucleic acid domains of the proximity probes (e.g. where the nucleic acid domains hybridise to a common template), and/or the nucleic acid domains may template a ligation reaction (e.g. where the nucleic acid domains are mutually complementary).

By way of a more specific example, in one embodiment of a method of the invention, the proximity probes may interact by being joined to one another, for example by ligation. The interaction may be detected by detecting the joined product (interaction product; ligation product). In one format of the method the interaction of said nucleic acid domains requires one or more ligation template (splint) oligonucleotides to bind to the domains, and mediate their interaction (specifically in the case of ligation, the splint oligonucleotide which hybridises to the domains and acts as a template for the ligation reaction) and the splint assists in or mediates this interaction. As will be appreciated from the description of various proximity assays above and the specific examples described below, in other formats/embodiments, the splint may be provided as the nucleic acid domain of a third proximity probe, and/or the ligation of the nucleic acid domains may be direct (i.e. the nucleic acid domains may be ligated directly to one another), or indirect, i.e. they may be ligated indirectly, for example via the intermediacy of a gap oligonucleotide; in one such embodiment the nucleic acid domains may hybridise to the splint oligonucleotide leaving a gap between their respective ends—this gap may be filled by a gap oligonucleotide or by extending the end (a free 3' end) of one of the nucleic acid domains using a polymerase enzyme. Such "gap-fill" embodiments of proximity ligation assays are well-described in the literature, for example in WO 01/61037 or in WO 2007/107743.

In a particularly preferred embodiment, the nucleic acid domains of three proximity probes may be ligated together, mediated by two ligation template (splint) oligonucleotides, as shown in FIG. 2. In this embodiment, the nucleic acid domain of the first proximity probe is unfolded by cleavage to yield two free ligatable ends, a 5' and 3' end. Each free end is ligated to the nucleic acid domain of a second and third proximity probe respectively, each ligation mediated by a ligation template oligonucleotide (i.e. a common template). It will be apparent that one or both of the second and third proximity probes could be in the form of unfolding proximity probes. In embodiments where all of the unfolding proximity probes can be unfolded by a single mechanism, e.g. cleavage, the addition of a single reagent, e.g. a cleavage enzyme, after the probes have been allowed to bind to the analyte will result in unfolding of the nucleic acid domains facilitating their interaction. In embodiments where the unfolding proximity probes require different unfolding mechanisms, each probe may be unfolded separately as described above. The sequential nature of the unfolding may minimise unwanted interactions between nucleic acid molecules in the sample.

The ligation product from such a reaction may be detected by any suitable means, e.g. PCR amplification of part or all of the ligation product, wherein the amplification product is detected as described in detail below.

In a further preferred embodiment, following binding of the proximity probes to the analyte, a first proximity probe is unfolded by cleavage to yield a partially double stranded nucleic acid domain, wherein one strand comprises two free ligatable ends (akin to a padlock probe, described elsewhere herein). Each end comprises a region of complementarity to the nucleic acid domain of a second proximity probe. The nucleic acid domain of the second proximity probe acts as a ligation template to mediate the ligation of the two free ends of the first proximity probe to form a circular oligonucleotide (see e.g. FIG. 3A). This circular oligonucleotide, i.e. the ligation product, may be detected any suitable means, e.g. rolling-circle amplification. The embodiment shown in FIG. 3A may be seen as the release, by cleavage of the unfolding probe, of a circularisable oligonucleotide, namely a padlock probe. Whilst not depicted in FIG. 3A or FIG. 4, it will be evident that, in a representative embodiment, the nucleic acid domain of the second proximity probe could act as both the ligation template to mediate the ligation of the two free ends of the first proximity probe and as the primer for amplification of the ligation product, e.g. the primer for rolling-circle amplification.

As described in more detail below, FIG. 3B shows the release of a two-part padlock probe, namely the release of two half-circles for ligation, one from the each of the nucleic acid domains of two proximity probes (or alternatively the release of one half-circle for ligation to a half-circle provided by the nucleic acid domain of a second proximity probe).

In some embodiments, the ligation of the free ends of the unfolded proximity probe may be ligated indirectly, e.g. via one or more gap oligonucleotides or after the "gap-fill" extension of the 3' end of the oligonucleotide, as described elsewhere herein.

In further embodiments, one of the nucleic acid domains of the first or second proximity probes may act as a primer for rolling-circle amplification. Thus, the portion of the nucleic acid domain of the first proximity probe that does not participate directly in the ligation reaction may have an extensible 3' end. Alternatively, the ligation template of the second proximity probe may also act as a primer, following the ligation reaction. In another embodiment, the primer for amplification of the circularised oligonucleotide may be provided on a third proximity probe.

Thus, it may in some embodiments be desirable that the portion of the nucleic domain of the first proximity probe that is not ligated, or the nucleic acid domain of the second proximity probe which releases the ligation template do not have free 3' ends which enable them to act a primers (i.e. they have a free 5' end and cannot act as primers). Thus priming of amplification of the ligation product (e.g. circularised oligonucleotide) can only take place by the addition of primer or, for example, by a primer provided on a third proximity probe (which may also be unfolded).

Upon the addition of an appropriate polymerase (and if necessary primer(s)), the presence of analyte in the sample may be detected by an rolling circle amplification (RCA) of the circularised oligonucleotides. The concatemeric RCA products, which can only be formed when the proximity probes bind in proximity, i.e. to form a template for the hybridisation or the oligonucleotide and/or ligation reaction, provides the marker "signal" for detection of the analyte. Said signal may be detected by any appropriate means known in the art (see below for further examples) and as taught in U.S. Pat. No. 7,320,860, e.g. by hybridisation of labelled probes to the reporter domain sequence, which is repeated throughout the concatemeric RCA products. As mentioned above, the use of proximity probes that comprise nucleic acid domains with hairpin loops means that the nucleic acid domains of the proximity probes cannot interact with each other until the hairpin structures are unfolded. Accordingly, in representative embodiments, additional reagents that may be required to detect the interaction of the proximity probes, e.g. amplify the interaction product, may be added to the reaction at the same time as the proximity probes, thereby avoiding the need for the addition of specific detection reagents in a separate step. Minimising the number of steps in the proximity assay may facilitate the reduction in the overall time needed to carry out the assay, i.e. increase the efficiency of the assay, and contribute to the enhanced signal to noise ratio, i.e. help to reduce non-specific background.

In a further embodiment the nucleic acid domain of the second proximity probe may comprise a partially double stranded nucleic acid molecule, wherein one strand has two free ligatable ends. In this embodiment, ligation template oligonucleotides present in the assay mediate the ligation of the nucleic acid domains of the first and second proximity probes (directly or indirectly) to produce a circular oligonucleotide (see FIG. 3B). Hence, the ligation template oligonucleotides each have a region of complementary to one end of both the nucleic acid domains of the first and second proximity probes. For instance, the first ligation template oligonucleotide may have a region of complementarity to the 3' end of the first proximity probe and the 5' end of the second proximity probe, whereas the second ligation template oligonucleotide may have a region of complementarity to the 5' end of the first proximity probe and the 3' end of the second proximity probe. Hence, the ligation templates may be viewed as common templates to which the nucleic acid domains of the proximity probes bind coincidently or simultaneously, i.e. in this (and in other embodiments involving common ligation templates) the ligation templates comprise a different region of complementarity for each nucleic acid domain. As discussed above, more than one of the proximity probes of the assay may be an unfolding proximity probe, see e.g. FIGS. 4 and 5. Furthermore, one or both of the ligation template oligonucleotides may be provided as a nucleic acid domain of a proximity probe (see e.g. FIG. 6), which also may be unfolding proximity probes.

In a further specific example, one or more of the nucleic acid domains of the proximity probes may act to template the ligation of one of more added oligonucleotides. In one such embodiment, following the unfolding of one or more of the proximity probes, e.g. by cleavage of the hairpin, a first added oligonucleotide may hybridise to both nucleic acid domains, and one or more further oligonucleotides may be added which hybridise to only one of the domains, for example one to each of the nucleic acid domains, each adjacent to each end of the first oligonucleotide, which may be ligated to the first oligonucleotide in a reaction templated by the nucleic acid domains. Again, the ligation product may be detected by any suitable means.

In alternative embodiments, the added oligonucleotide(s) may be circularised by the ligation reaction (i.e. akin to a padlock probe as described above). Thus, by way of example the nucleic acid domains of a pair of proximity probes (of which at least one is an unfolding proximity probe unfolded by cleavage), which are attached to the analyte-specific binding moieties of the respective probes, may have complementarity, respectively, to (i) the 5' and 3' ends, and (ii) region between said ends, of an added linear oligonucleotide (akin to a "padlock probe"). When both probes of the proximity probe pair are brought into proximity due to binding to the same analyte, the nucleic acid domains of the respective probes are able to hybridise to the respective parts of the added oligonucleotide (which may be viewed as a common template), following unfolding of the hairpin of the unfolding proximity probe. The nucleic acid domain with complementarity to the 5' and 3' ends of the added oligonucleotide templates the juxtaposed hybridisation, and ligation (on addition of an appropriate ligase), of said ends, resulting in circularisation of the added oligonucleotide. This circularised oligonucleotide is then detected by rolling circle amplification (RCA) using the other nucleic acid domain as primer; the nucleic acid domain of the other probe of the pair, which is hybridised to a region of the added oligonucleotide between the ligated ends, has a free 3' end. Upon the addition of an appropriate polymerase, the presence of analyte in the sample may be detected by an rolling circle amplification (RCA) of the circularised oligonucleotide. The concatemeric RCA product, which can only be formed when the proximity probes bind in proximity, provides a "surrogate" marker for detection of the analyte.

It will be appreciated that the single added oligonucleotide can be replaced by two oligonucleotides which may be ligated together to form a circle (such a ligation may be templated by one or both nucleic acid domains, but one of the domains will have a free 3' end to act as a primer). Alternatively, the single added oligonucleotide may be in the form of a preformed circle such that no ligation reaction is required. For instance, the preformed circle may hybridise to the nucleic acid domain of a first proximity probe, which brings the circular oligonucleotide into proximity with the nucleic acid domain of a second proximity probe, which is able to act as a primer for RCA. In these embodiments, one or both of the proximity probes may be unfolding proximity probes. Hence, the preformed circle may only hybridise after unfolding or only template a RCA after unfolding, or both.

Proximity probing reactions can also be performed by utilizing two free 3' ends, one on each proximity probe with weak complementarity, and when in proximity (following unfolding of the at least one unfolded proximity probe to generate a region of complementarity), a DNA polymerase can extend these ends by adding dNTPs thus forming a detectable DNA template as described in U.S. Pat. Nos. 7,306,904 and 6,511,809.

In yet a further specific embodiment, which demonstrates the potential complexity of the methods of the invention, at least four proximity probes may be used, wherein any one or more of said proximity probes may be unfolding proximity probes, as defined herein. An example is shown in FIG. 14, in which the nucleic acid domain of the a first proximity probe comprises a primer for rolling-circle amplification. The nucleic acid domain of the second proximity probe is capable, e.g. when unfolded by cleavage, of forming a circular oligonucleotide (i.e. it may release a padlock probe, or circularisable oligonucleotide, on cleavage) and comprises a region of complementary to a preformed circular oligonucleotide, which is hybridised thereto. The nucleic acid domain of the third proximity probe comprises a region of complementarity to the nucleic acid domain of the second proximity probe, such that it is capable of mediating the interaction of the free ligatable ends of the nucleic acid domain of the second proximity probe following its cleavage, i.e. the nucleic acid domain of the third proximity probe comprises a ligation template. The nucleic acid domain of a fourth proximity probe comprises a region of complementarity to the preformed circle hybridised to the nucleic acid domain of the second proximity probe, so as to form a cleavage recognition site, preferably a restriction endonuclease cleavage site.

Hence in this embodiment, once the proximity probes have bound to the analyte, the nucleic acid domains may be unfolded as described elsewhere herein. Preferably the nucleic acid domain of at least the second proximity probe is unfolded by cleavage such that two free ligatable ends are released, i.e. the nucleic acid domain is cleaved such that two single strands of nucleic acid are produced that are partially hybridised, wherein one nucleic acid strand comprises a middle region that remains hybridised to part of the parent nucleic acid strand attached to the analyte binding domain.

Thus, the "unfolded" nucleic acid domains of the four proximity probes, only when bound to the analyte, may interact based on the interaction domains as described above and as shown in FIG. 14. The nucleic acid domain of the second proximity probe may be ligated to form a circular oligonucleotide, wherein said ligation is templated by the nucleic acid domain of the third proximity probe. Whilst the nucleic acid domain of the first proximity probe may hybridise to the ligated circular oligonucleotide, extension of the nucleic acid domain of the first nucleic acid domain (using the ligated circular oligonucleotide of the second proximity probe as a template for RCA) is inhibited by the presence of the preformed circular oligonucleotide, which is hybridised to the nucleic acid domains of both the second and fourth proximity probes. However, on cleavage of the cleavage recognition site formed by the interaction (hybridisation) between the preformed circular oligonucleotide and the nucleic acid domain of the fourth proximity probe, the RCA reaction may proceed, i.e. cleavage results in the linearisation of the preformed circular oligonucleotide. However, the linearised preformed circular oligonucleotide comprises a exonuclease block (described in detail below), which prevents it from acting as a primer for RCA. Hence, RCA may only proceed if the nucleic acid domain of the fourth proximity probe has been unfolded and allowed to hybridise to the ligated circular oligonucleotide of the second proximity probe. Detection of the RCA product corresponds to the ligation of the nucleic acid domain of the second proximity probe, thereby signalling the presence of the analyte in the sample.

An exonuclease block may be used in any proximity assays described herein, wherein it is useful to prevent one or more nucleic acid domains of the proximity probes from acting as a primer, e.g. to ensure that nucleic acid extension is achieved via the appropriate primer, which may be a nucleic acid domain of a proximity probe or a free nucleic acid molecule. It may also be useful to prevent nucleic acid domains from generating unwanted extension products. For instance, in embodiments where the analyze-binding domain is a nucleic acid molecule (see e.g. FIGS. 7 and 8) it may be useful to incorporate an exonuclease block in the nucleic acids that are not used as the primer for detecting the interaction between the nucleic acid domains of the proximity probes, e.g. to avoid extension of the nucleic acids, which may cause downstream displacement of nearby bound similar constructs. In representative embodiments, it is possible to detect simultaneously several regions on a single nucleic acid in tandem (e.g. using proximity probes represented in FIGS. 7 and 8) and extension of the nucleic acid analyte-binding domains could result in the displacement of other proximity probe complexes bound downstream of a proximity probe.

An exonuclease block is particularly useful in assays that utilise a polymerase with 3' exonuclease activity, e.g. rolling-circle amplification reactions, although any modification of the nucleic acid molecule that prevents it from being used as a primer would be appropriate, e.g. prevent the nucleic acid from being recognised by the polymerase. In a representative embodiment, rolling-circle amplification advantageously utilises a polymerase with 3' exonuclease activity, e.g. Phi29, wherein the exonuclease activity tracks from 3' to 5' along the strand while the polymerase extends the primer from 5' to 3'. If the enzyme encounters a blocking group attached to the DNA it is inhibited from functioning. Hence, a nucleic acid molecule that contains a blocking group cannot function as a primer for nucleic acid extension. Any suitable blocking group may be used, such as a nucleotide modification, e.g. modification of a nucleotide with a group that prevents the polymerase from binding to the primer, e.g. by steric hindrance, e.g. biotin, or a group that cannot be processed by the enzyme. In representative embodiments, the nucleic acid molecule to be blocked, e.g. exonuclease blocked, may incorporate any suitable modification known in the art, such as 2'O-Me-RNA residues, Locked Nucleic Acids (LNA), Peptide Nucleic Acids (PNA), phosphothioate-modified nucleic acids, Poly-ethylene-linker backbone stretches in between nucleic acids etc. There are several means of modifying nucleic acids so that they are exonuclease resistant and/or do not function as a primer and it is not intended that the methods of the invention are not limited to the examples listed above.

As described above, the analyte-binding domain may be any binding partner for the target analyte, and it may be a direct or indirect binding partner therefor. Thus it may bind to the target analyte directly or indirectly via an intermediary molecule or binding partner which binds to the target analyte, the analyte-binding domain binding to said intermediary molecule (binding partner). Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

In some embodiments where the proximity probe binds to the analyte via an intermediary molecule, the proximity probe may be pre-incubated with the intermediary molecule. For example, in embodiments where the proximity probe is a horn probe (as described elsewhere herein) that binds to the nucleic acid domain of a further proximity probe that binds target analyte directly, the horn probe may be pre-hybridized to the nucleic acid domain of the further proximity probe. In this embodiment, the horn probe may be seen as forming part of the nucleic acid domain of the further proximity probe. In a preferred embodiment, the horn probe is not pre-hybridized to the nucleic acid domain of a further proximity probe. Such a representation is depicted in FIG. 11. In such an embodiment, the horn probe may be viewed a first proximity probe (which is indirectly bound to the analyte). In such a situation the two proximity probes which are directly bound to the analyte may be viewed as second and third proximity probes. Alternatively viewed, the horn probe may be viewed as part of the nucleic acid domain of the "third" proximity probe.

The analyte binding domain may be selected to have a high binding affinity for a target analyte. By high binding affinity is meant a binding affinity of at least about $10^{-4}$ M, usually at least about $10^{-6}$ M or higher, e.g., $10^{-9}$ M or higher. The analyte binding domain may be any of a variety of different types of molecules, so long as it exhibits the requisite binding affinity for the target analyte when present as part of the proximity probe. In other embodiments, the analyte binding domain may be a ligand that has medium or even low affinity for its target analyte, e.g. less than about $10^{-4}$ M.

Hence, the analyte binding domain of the proximity probe may be any molecule capable of selectively binding to a target molecule. For example, the binding domain may be selected from a protein, such as a monoclonal or polyclonal antibody, lectin, soluble cell surface receptor, combinatorially derived protein from phage display or ribosome display, peptide, carbohydrate, nucleic acid, such as an aptamer or a nucleic acid molecule comprising the complementary sequence for a target nucleic acid, or combinations thereof. In a preferred embodiment of the invention, the analyte binding domain is a protein, preferably an antibody or derivative or fragment thereof.

In another preferred embodiment of the analyte-binding domain of the proximity probe is a nucleic acid molecule. The analyte-binding domains of the proximity probes may be made up of ribonucleotides and/or deoxyribonucleotides as well as synthetic nucleotide residues that are capable of participating in Watson-Crick type or analogous base pair interactions. Thus, the nucleic acid domains may be DNA and/or RNA or any modification thereof e.g. PNA or other derivatives containing non-nucleotide backbones. In some embodiments, the analyte-binding domain may comprise an exonuclease block, such that it cannot be used as a primer in a nucleic acid extension reaction, i.e. cannot be recognised as a primer by a polymerase enzyme.

Examples of proximity ligation reactions, as described above, wherein the analyte-binding domains of the proximity probes are nucleic acid molecules are shown in FIGS. 7 and 8. Whilst these examples depict assays where all of the proximity probes are unfolding proximity probes, it will be understood that the invention encompasses assays where only one proximity probe is an unfolding proximity probe, which is unfolded by cleavage. However, in a preferred embodiment, more than one proximity probe is an unfolding proximity probe. In a particularly preferred embodiment, all of the proximity probes in the reaction are unfolding proximity probes. However, as described above, the hairpin structures of the unfolding proximity probes may be unfolded in different ways. In a preferred embodiment, the nucleic acid domains of all of the unfolding proximity probes in a reaction are unfolded in the same way, preferably by cleavage.

In one embodiment, where the analyte-binding domain of at least one of the proximity probes is a nucleic acid, the at least one proximity probe is a padlock probe, i.e. a circularisable oligonucleotide. In a particularly preferred embodiment the padlock probe comprises at least one hairpin structure, i.e. is a so-called horn probe.

Thus, a horn probe is a particular type of unfolding proximity probe and may be defined as an oligonucleotide comprising:

(i) a first domain comprising two regions of complementarity to a first target sequence, wherein said the first region of complementarity is at the 5' end of the oligonucleotide and the second region of complementarity is at the 3' end of the oligonucleotide, and wherein said regions of complementarity hybridize to the first target sequence such that the 5' and 3' ends are directly or indirectly ligatable;

(ii) a second domain comprising two regions of complementarity to a second target sequence, wherein at least part of at least one of said regions of complementarity is complementary to a sequence within the oligonucleotide, such that it forms part of a hairpin structure, which inhibits said regions complementarity from hybridizing to the second target sequence;

wherein unfolding of the hairpin structure enables the regions of complementarity of the second domain to hybridize to the second target sequence.

Optionally, where the hairpin is unfolded by cleavage, the regions of complementarity of the second domain hybridize to the second target sequence such that the 5' and 3' ends are directly or indirectly ligatable. More particularly, the regions of complementarity of the second domain lie at the 5' and 3' ends of the second domain which are released by cleavage of the probe.

In embodiments where the regions of the first and/or second domains hybridize to their respective targets such that they are indirectly ligatable, i.e. there is a gap between the 5' and 3' ends, said gap may be filled by a gap oligonucleotide or by extension of the 3' end until it is directly ligatable to the 5' end of the second domain.

In the methods of the present invention, the first domain is preferably the analyte-binding domain, which binds to the analyte directly or indirectly, i.e. via an intermediary molecule, e.g. an aptamer capable of binding specifically to the target analyte or an analyte-binding domain as defined above coupled to a nucleic acid molecule comprising the first target sequence.

Similarly, the second domain is preferably the nucleic acid domain (namely the nucleic acid domain of a proximity probe). The second target of the probe may be the nucleic acid domain of a second proximity probe as defined herein.

The horn probes as described herein form one aspect of the present invention are particularly advantageous because they can utilise two proximity dependent ligation reactions to generate a circular oligonucleotide, in comparison to the single ligation of a "standard" padlock probe. It is believed that the additional ligation reaction improves the specificity and selectivity of the proximity probe assays.

In a preferred embodiment, the horn probe comprises two hairpin structures, e.g. wherein at least part of two of said regions of complementarity of the second domain are complementary to a different sequences within the oligonucleotide (see e.g. FIG. 9). Unfolding said hairpin structures enables the regions of complementarity of the second domain to hybridize to the second target sequence.

Thus, the horn probes of the invention may be used in methods for the detection of an analyte in a sample. In one aspect of the invention, one or more horn probes may be used when the analyte is a nucleic acid molecule. For instance, the first and second target sequences for a horn probe may be present in a single nucleic acid molecule. FIG. 15 depicts a horn probe, in which the first and second regions of complementarity of the first domain hybridise to a first target sequence in the analyte (a nucleic acid molecule), which templates the ligation of the first domain. The probe is unfolded, e.g. by cleavage, which enables the two regions of the second domain of the horn probe to hybridise to the second target sequence in the nucleic acid analyte. In this embodiment, the second target sequence templates the ligation of the second domain, which results in a circular oligonucleotide, which can be detected, e.g. by RCA. It will be evident that a similar reaction could be performed using two horn probes, see e.g. FIG. 10. In this embodiment the nucleic acid domains comprising the first target sequence for each horn probe is present on a single nucleic acid molecule and the second target sequence for one region of complementarity of the second domain of each horn probe is present in a ligation template oligonucleotide.

Hence, a further aspect of the invention provides the use of at least one horn probe in the detection of a nucleic acid analyte in a sample, wherein said nucleic acid analyte is at least partially single stranded.

Expressed another way, the invention provides a method for use in the detection of a partially single stranded nucleic acid analyte in a sample, comprising:

a) contacting said sample with at least one horn probe, comprising:
 (i) a first domain comprising two regions of complementarity to a first target sequence, wherein said the first region of complementarity is at the 5' end of the oligonucleotide and the second region of complementarity is at the 3' end of the oligonucleotide, and wherein said regions of complementarity hybridize to the first target sequence such that the 5' and 3' ends are directly or indirectly ligatable;
 (ii) a second domain comprising two regions of complementarity to a second target sequence, wherein at least part of at least one of said regions of complementarity is complementary to a sequence within the oligonucleotide, such that it forms part of a hairpin structure, which inhibits said regions complementarity from hybridizing to the second target sequence;
 wherein unfolding of the hairpin structure enables the regions of complementarity of the second domain to hybridize to the second target sequence;
(b) directly or indirectly ligating the first and second regions of complementarity of said first domain when the at least one horn probe binds to said analyte; and
(c) detecting said ligation.

In some embodiments the at least partially single stranded nucleic acid analyte comprises a first target sequence and a second target sequence that are complementary to the first and second domains of the horn probe, respectively. Thus, in a preferred embodiment, said method comprises also directly or indirectly ligating the first and second regions of complementarity of the second domain when the at least one horn probe binds to the analyte.

In other embodiments the at least partially single stranded nucleic acid analyte comprises at least a first target sequence that is complementary to the first domain of each horn probe. Thus, in a preferred embodiment, where the method uses more than one horn probe the second target sequence for one region of complementarity of the second domain of each horn probe is present in a ligation template oligonucleotide, which may form part of the nucleic acid analyte. Hence, in some embodiments, the first and/or second regions of complementarity of the second domain of the horn probes are ligated to the first and/or second regions of the second domain of another horn probe.

In a particularly preferred embodiment, the nucleic acid analyte is fully single stranded. If necessary, the nucleic acid analyte may be rendered partially or fully single stranded by any suitable means known in the art, e.g. enzymatic digestion/degradation, denaturation by heat, etc. The nucleic acid analyte may be rendered partially or fully single stranded before, after or contemporaneously with the contact of the sample with the at least one horn probe. Preferably the nucleic acid analyte is rendered partially or fully single stranded before the at least one horn probe is contact with said sample.

Another aspect of the invention concerns an unfolding proximity probe comprising an analyte-binding domain (as defined herein) coupled to a nucleic acid domain, wherein said nucleic acid domain comprises:
 (i) at least one region of complementarity to a target sequence; and
 (ii) a region of self-complementarity such that it forms a hairpin structure which inhibits said at least one region of complementarity from hybridizing to the target sequence;
 wherein unfolding of the hairpin structure results in a partially double stranded nucleic acid domain, which comprises a free 5' and 3' end and enables said at least one region of complementarity of the nucleic acid domain to hybridize to the target sequence.

In a representative embodiment, the nucleic acid domain of the unfolding proximity probe may be cleaved such that two single strands of nucleic acid are produced that are partially hybridised to each other, wherein one nucleic acid strand comprises a middle region that remains hybridised to part of the parent nucleic acid strand attached to the analyte binding domain.

In a preferred embodiment, the analyte-binding domain of the unfolding proximity probe described above is other than a nucleic acid.

The unfolding proximity probe set out above is for use in the methods of the invention as described herein. Hence, in one embodiment the target sequence comprises part of a ligation template, wherein said ligation template may be in the form of a nucleic acid domain of a proximity probe. Alternatively, said ligation template may be a free oligonucleotide, i.e. not coupled to an analyte-binding domain.

In a further embodiment, the free 5' and 3' ends of the partially double stranded nucleic acid domain may be ligated directly or indirectly to form a circular oligonucleotide. In an alternative embodiment, the 5' end of the partially double stranded nucleic acid domain may be ligated to the 3' end of the nucleic acid domain of a further proximity probe. In an additional or alternative embodiment, the 3' end of the partially double stranded nucleic acid domain may be ligated to the 5' end of the nucleic acid domain of a further proximity probe (see, e.g. FIG. 2).

It will be evident that different types of proximity probes can be used in combination in the methods of the invention. For example, the analyte-binding domain of the first proximity probe may comprise an antibody or fragment thereof and the analyte-binding domain of the second proximity probe may comprise a nucleic acid, e.g. the second proximity probe may be a horn probe. In a further representative example the analyte-binding domain of the first proximity probe may comprise a lectin and the analyte-binding domain of the second proximity probe may comprise a soluble cell surface receptor. All possible combinations are encompassed herein.

Similarly, various combinations of nucleic acid domains are also encompassed by the methods of the invention. For example, the first proximity probe may be an unfolding proximity probe and the second proximity probe may not comprise a hairpin structure. Similarly, in some embodiments the third, fourth etc proximity probes may not comprise a hairpin structure. Alternatively, all proximity probes may be unfolding proximity probes. Any such combination is encompassed by the methods of the present invention.

In particularly preferred embodiments, the analyte-binding domains of the at least first and second proximity probes comprise an antibody or fragment thereof. In a further preferred embodiment the at least first and second proximity probes comprise horn probes, see e.g. FIG. 10. In yet another preferred embodiment the first proximity probe is a horn probe and the second proximity probe is a non-horn probe, see e.g. FIG. 1. In some embodiments, the horn probe is indirectly bound to the analyte, e.g. via the nucleic acid domain of a further (e.g. "third") proximity probe (see FIG. 11).

Any indirect ligation reaction encompassed by the methods of the invention may encompass the use of a gap oligonucleotide. Hence, in embodiments that utilise a horn probe, both the first and second ligation reactions may involve a gap oligonucleotide (see e.g. FIG. 12). This is particularly advantageous in multiplex embodiments of the invention, i.e. where more than one analyte is detected in a single assay, wherein the gap oligonucleotide may comprise a unique "marker" or identification sequence (e.g. a bar-code sequence, or a binding site for a specific detection probe) to allow the separate detection and/or quantification of each analyte in the sample. Thus, in multiplex assays each proximity probe set may comprise a different marker and the detection of the interaction of the probes, i.e. the detection of each analyte, may be detected in parallel (i.e. at the same time), e.g. using oligonucleotides tagged with distinct fluorophores that may hybridise to their respective marker. Alternatively, each marker (and therefore each analyte) may be detected using sequential visualisation reactions, wherein each reaction is separated by, e.g. stripping or bleaching steps. Methods of sequential visualisation reactions suitable for using the methods of the invention are known in the art, e.g. Göransson et al., 2009 (A single molecule array for digital targeted molecular analyses. Nucleic Acids Res. 2009 January; 37(1):e7), Wählby et al., 2002 (Sequential immunofluorescence staining and image analysis for detection of large numbers of antigens in individual cell nuclei. Cytometry, 47(1):32-41, 2002), which are hereby incorporated by reference. In some representative embodiments of the invention, multiple analytes may be detected in parallel. In other representative embodiments of the invention, multiple analytes may be detected sequentially.

Thus embodiments that utilise more than one gap oligonucleotide in the generation of a single ligation product may incorporate more than one marker, such that the ligation is, e.g. dual labelled. In other embodiments, the nucleic acid domain of proximity probes of the invention may comprise a marker sequence, and the ligation of a gap oligonucleotide may introduce a further marker sequence.

In this respect, in some embodiments the gap oligonucleotide may comprise two regions of complementarity to the ligation template, which regions are separated by a sequence that is not complementary to the ligation template. Hence, the two regions of complementarity to the ligation template are at the 5' and 3' ends of the gap oligonucleotide, respectively. Consequently, the sequence that is not complementary to the ligation template forms a loop or bulge (see e.g. FIG. 13) and may comprise a marker sequence, e.g. a barcode sequence.

An advantage of an unfolding proximity probe of the present invention is that an unfolded nucleic acid domain of an unreacted probe, for example a probe which has not bound to its target analyte, may be prevented from participating in any unwanted reactions which may give rise to unwanted background signals. For example, it is known in the art that unreacted oligonucleotide probes (for example padlock probes which have not been circularised) which have a free 3' end may participate in priming unwanted extension reactions, including unwanted amplification reactions (e.g. PCR or RCA reactions), for example causing undesirable amplification of non-specific sequences. It is further known in the art that hairpins may be included in such probes in order to allow "inactivation" of the unreacted probes to prevent such unwanted priming reactions. Thus, where the 3' end in an unreacted probe is involved in a hairpin structure, the 3' end may be extended, using the remainder of the probe as template. Such extension stabilises the hairpin and removes the ability of the unreacted probe to function as a primer (in a reacted probe, the hairpin is opened on reaction with its target). Such a system is described in U.S. Pat. No. 6,573,051 (Alsmadi et al.) and in WO 03/012119. It will be seen that unfolding nucleic acid domains of proximity probes according to the present invention may be designed in analogous manner to the above-described "suicide probes", such that the unfolded nucleic acid domains of any unreacted probes may be extended from the 3' end using a part of the domain sequence as template, so as to stabilise the hairpin structure.

The term "detecting" is used broadly herein to include any means of determining the presence of the analyte (i.e. if it is present or not) or any form of measurement of the analyte. Thus "detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g., through generation of a standard curve). Alternatively, relative quantification can be accomplished by comparison of detected levels or amounts between two or more different target analytes to provide a relative quantification of each of the two or more different analytes, i.e., relative to each other.

The "analyte" may be any substance (e.g. molecule) or entity it is desired to detect by the method of the invention. The analyte is the "target" of the assay method of the invention. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. It will be seen therefore that the analyte can be any substance or entity for which a specific binding partner (e.g. an affinity binding partner) can be developed. All that is required is that the analyte is capable of simultaneously binding at least two binding partners (more particularly, the analyte-binding domains of at least two proximity probes). Proximity probe-based assays, such as that of the present invention, have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. regulatory factors, such as transcription factors, and DNA or RNA. In other representative embodiments, the analyte may be a nucleic acid molecule or region thereof. Hence, the analyte may be DNA (e.g. genomic, mitochondrial) or RNA (e.g. messenger RNA, ribosomal RNA, microRNA etc). Advantageously, the nucleic acid may be detected in situ, i.e. without removing or extracting the nucleic acid from the cell.

All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins or an interaction between different molecules), the analyte-binding domains will be different.

Since the length of the nucleic acid domain of the proximity probes can be constructed to span varying molecular distances, binding sites on the analyte for the analyte-binding domain need not be on the same molecule. They may be on separate, but closely positioned, molecules. For example, the multiple binding domains of an organism, such as a bacterium or cell, or a virus, or of a protein complex or interaction can be targeted by the methods of the present invention.

The proximity probes for use in the detection method of the invention comprise an analyte-binding domain and functional domain which is preferably a nucleic acid domain, but as noted above, one or more of the proximity probes used in a proximity assay may comprise a different functional group such as an enzyme. Proximity probes are in effect detection probes which bind to the analyte (via the analyte-binding domain), the binding of which may be detected (to detect the analyte) by means of detecting the interaction which occurs between the functional (e.g. nucleic acid) domains thereof upon such binding. Accordingly, where the functional domain is a nucleic acid molecule, the probes may be viewed as nucleic acid-tagged affinity ligands or binding partners for the analyte, the analyte-binding domain being the affinity binding partner, and the nucleic acid domain the nucleic acid tag. The nucleic acid domain is coupled to the analyte-binding domain and this "coupling" or connection may be by any means known in the art, and which may be desired or convenient and may be direct or indirect, e.g. via a linking group. Where both the analyte-binding domain and the functional domains are nucleic acids, it is preferred that the domains are coupled by a nucleotide bond, i.e. a phosphodiester bond. Examples of the way in which a protein may be coupled to a nucleic acid are described in detail below. Preferably, where the proximity probes do not comprise only nucleic acids the linker or the means used to couple the analyte-binding domain and the nucleic acid domain of the proximity probe is same for each proximity probe.

In a preferred aspect of the methods of the invention, the analyte-binding domain of at least one proximity probe (further preferably of at least two, or more preferably of all the proximity probes) is a proteinaceous molecule. Thus, the analyte-binding domain may be a small peptide molecule or a larger polypeptide or protein. A peptide may, for example range in size from about 5 to about 100 amino acid residues, usually from about 5 to about 50 residues and more usually from about 10 to about 30 residues. By large polypeptide or protein is meant a molecule ranging in size from about 100 amino acid residues or greater. Of particular interest as analyte-binding domains are antibodies, as well as binding fragments and derivatives or mimetics thereof. Where antibodies are the analyte-binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same nucleic acid. As such, the analyte-binding domain may be either a monoclonal or polyclonal antibody. In yet other embodiments, the affinity-binding domain is an antibody fragment or derivative or mimetic thereof, where these fragments, derivatives and mimetics have the requisite binding affinity for the target analyte. Examples of antibodies, antibody fragments, mimetics and derivatives thereof are described above and the present invention contemplates the affinity-binding domain may be any type of these molecules, provided they have the requisite binding affinity for the target analyte.

The term "antibody" as used herein can mean an antibody binding fragment or derivative or mimetic thereof, where these fragments, derivatives and mimetics possess the binding affinity for the target analyte. For example, antibody fragments, such as Fv, F(ab)$_2$ and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies, i.e. that they are not capable of binding specifically to the target analyte. Such antibody fragments or derivatives generally include at least the $V_H$ and $V_L$ domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

In other preferred embodiments, as described above, the analyte-binding domain of one or more (preferably two or more or all) of the proximity probes may be a nucleic acid molecule.

Importantly, the analyte-binding domain will be one that includes a moiety that can be covalently attached to the nucleic acid domain without substantially abolishing the binding affinity of the analyte-binding domain to its target analyte.

In one embodiment of the method of the present invention the proximity probes may be multivalent proximity probes. Such multivalent proximity probes comprise at least two, analyte binding domains conjugated to at least one, and preferably more than one, nucleic acid(s). Thus, multivalent proximity probes may comprise at least 5, 10, 20, 50, 100, 200, 500 or 1000 analyte-binding domains conjugated to at least one, and preferably more than one, nucleic acid(s).

The "coupling" or connection as described above may be by any means known in the art, and which may be desired or convenient and may be direct or indirect e.g. via a linking group. For example, the domains may be associated with one another by covalent linkage (e.g. chemical cross-linking) or by non-covalent association e.g., via streptavidin-biotin based coupling (biotin being provided on one domain and streptavidin on the other).

The two components of the proximity probes may be joined together either directly through a bond or indirectly through a linking group. Where linking groups are employed, such groups may be chosen to provide for covalent attachment of the binding domain and nucleic acid domain through the linking group. Linking groups of interest may vary widely depending on the nature of the component domains. The linking group, when present, is in many embodiments biologically inert. A variety of linking groups are known to those of skill in the art and find use in the subject proximity probes. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the nucleic acid domain or protein component. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids. N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject markers include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyitartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

The proximity probes employed in the subject methods may be prepared using any convenient method. In representative embodiments, the analyte-binding domains and the nucleic acid domains may be coupled, either directly or through a linking group. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the proximity probe include: hydroxy, sulfhydryl, amino, and the like. The particular portion of the different components that are modified to provide for covalent linkage may be chosen so as not to substantially adversely interfere with that component's binding affinity for its target. In other words, the covalent linkage should not inhibit the analyte-binding domain of the proximity probe from binding the target analyte and should not encourage the nucleic acid domain to bind to the target analyte. Where necessary and/or desired, certain moieties on the components may be protected using blocking groups, as is known in the art, see e.g. Green & Wuts, Protective Groups in Organic Synthesis (John Wiley & Sons) (1991). Methods for producing nucleic acid/antibody conjugates are well known to those of skill in the art. See e.g. U.S. Pat. No. 5,733,523, the disclosure of which is herein incorporated by reference.

In other embodiments, the proximity probes may be produced using in vitro protocols that yield nucleic acid-protein conjugates, i.e. molecules having nucleic acids, e.g. coding sequences, covalently bonded to a protein, i.e. where the analyte-binding domain or protein component is produced in vitro from vectors which encode the proximity probe. Examples of such in vitro protocols of interest include: RepA based protocols (see e.g., Fitzgerald, Drug Discov. Today (2000) 5:253-258 and WO 98/37186), ribosome display based protocols (see e.g., Hanes et al., Proc. Natl Acad. Sci. USA (1997) 94:4937-42; Roberts, Curr Opin Chem Biol (1999) June; 3: 268-73; Schaffitzel et al., J Immunol Methods (1999) December 10; 231: 119-35; and WO 98/54312), etc.

As noted above, the analyte-binding domain may bind to the analyte directly or indirectly. In the case of indirect binding, the target analyte may first be bound by a specific binding partner (or affinity ligand), and the analyte-binding domain of the proximity probe may bind to the specific binding partner. This enables the design of proximity probes as universal reagents. For example the analyte-specific binding partner may be an antibody, and a universal proximity probe set may be used to detect different analytes by binding to the Fc regions of the various different analyte-specific antibodies.

The nucleic acid domains of the proximity probes may be regarded as the nucleic acid "tags" which interact to form a detectable product, which may be detected to report the detection of the analyte. The nucleic acid domains may thus be regarded as reactive nucleic acid functionalities, or as comprising reactive elements, which interact to provide the signal by means of which the analyte is detected (for example to form a signal-giving product (e.g. they may be ligated together to form a ligation product) or to mediate the formation or assist in the formation of a signal-giving product, e.g. as a ligation template and/or primer, for example as an RCA primer). Put another way, the nucleic acid domains may be regarded as "detection tags", which may interact to form a "detectable" tag or product. When two or more analytes are present in the same sample they may be detected simultaneously using two or more sets of proximity probes, each set of proximity probes being designed to form on interaction a unique nucleic acid sequence "detectable tag". These unique "detectable tags" may be detected and quantified (optionally after amplification) separately using methods well known in the literature including liquid chromatography, electrophoresis, mass spectrometry, DNA array technology, DNA sequencing and multi-colour real-time PCR. In some embodiments where the assay is a hetergeneous assay, e.g. the reaction is performed on a slide or array, the detection tags may be detected visually. For instance, the nucleic acid concatamer produced by RCA may be detected by hybridizing fluorescently labelled nucleic acid probes, yielding "spots" on a slide that can be visualised, e.g. using microscopy. As mentioned above, in assays for the detection of multiple analytes, the different analytes may be detected or visualised in parallel or sequentially. Hence, detection can be performed and quantified by counting individual reaction products. Therefore, in some embodiments the methods of the invention may be used for in situ detection of an analyte in a sample.

As described above, proximity probe based detection assays are well described in the prior art, e.g. WO 97/00446, WO 01/61037, WO 03/044231, WO 2005/123963 and WO 2007/107743, which are hereby incorporated by reference. Other proximity assays are also known and described in the art, for example in WO 2007/044903 and WO 2009/012220, also incorporated herein by reference. Thus, it is clear that the skilled person would be capable of modifying the detection methods as described herein using methods disclosed in the art, insofar as those methods extend to proximity probe based detection assays that utilise proximity probes. However, particularly preferred aspects of the detection methods of the invention are explained herein.

In one preferred method of detection of the present invention, the nucleic acid domains of first and second proximity probes may be joined together, for example by ligation. This "joining" (or "conjugation") may be direct, i.e. the respective nucleic acid domains may be directly joined to one another, or it may be indirect, i.e. the respective nucleic acid domains may be joined indirectly e.g. by joining each to one of the two ends of a further intermediary nucleic acid molecule (e.g. a "gap" oligonucleotide, also known in the art as a "a cassette" oligonucleotide). This "conjugation" or "interaction" (typically ligation) may be mediated by one or more ligation template (splint) oligonucleotides. As such, the splint or gap/cassette oligonucleotide may be added to the sample in the form of an independent nucleic acid, or it may be provided as the nucleic acid domain of a third proximity probe, as explained further below. The interaction (by ligation) results in the formation of a new nucleic acid molecule or sequence, which may be detected.

As mentioned above, and discussed further below, the ligation template oligonucleotide may hybridise to the nucleic acid domains of the first and second proximity probes, enabling their ligation. Alternatively, the ligation template may form the nucleic acid domain of one of more of the proximity probes. The ligation template may be viewed as a common template to which the nucleic acid domains of the proximity probes bind coincidently or simultaneously, i.e. the ligation template comprises a different region of complementarity for each nucleic acid domain.

Whilst the nucleic acid domain of at least one of the proximity probes in the methods of the invention comprises a hairpin structure that can be unfolded by cleavage, as described above, the nucleic acid domains of the second, third, fourth etc. proximity probes may be in any suitable form for a proximity assay. Hence, the nucleic acid domain of said proximity probes may be a single stranded nucleic acid molecule (e.g. an oligonucleotide), a partially double stranded and partially single stranded molecule, or a double stranded molecule that includes of a region that is double stranded and a region where the two nucleic acid strands are not complementary and therefore single stranded. As such, in certain embodiments, the nucleic acid domain is made up of a single stranded nucleic acid. In other embodiments, the nucleic acid domain may be made up of two partially complementary nucleic acid strands, where the two strands include a hybridized region and non-hybridized region.

The nucleic acid domains of the proximity probes are generally of a length sufficient to allow ligation template-mediated interaction with the nucleic acid domain of another proximity probe when bound to a target analyte. Nucleic acid domains are usually in the range of between about 8 up to about 1000 nucleotides in length, where in certain embodiments they may range from about 8 to about 500 nucleotides in length including from about 8 to about 250 nucleotides in length, e.g., from about 8 to about 160 nucleotides in length, such as from about 12 to about 150 nucleotides in length, from about 14 to about 130 nucleotides in length, from about 16 to about 110 nucleotides in length, from about 8 to about 90 nucleotides in length, from about 12 to about 80 nucleotides in length, from about 14 to about 75 nucleotides in length, from about 16 to about 70 nucleotides in length, from about 16 to about 60 nucleotides in length, and so on. In certain representative embodiments, the nucleic acid domain may range in length from about 10 to about 80 nucleotides in length, from about 12 to about 75 nucleotides in length, from about 14 to about 70 nucleotides in length, from about 34 to about 60 nucleotides in length, and any length between the stated ranges. In some embodiments, the nucleic acid domains are usually not more than about 28, 29, 30, 31, 32, 33, 34, 35, 36, 37, 38, 39, 40, 41, 42, 44, 46, 50, 55, 60, 65, or 70 nucleotides in length.

The at least one hairpin structure of the nucleic acid domain of the unfolding proximity probes may comprise any suitable number of nucleotide residues such that the hairpin can be unfolded. Preferably the hairpin structure will unfold only under suitable conditions, e.g. on the addition of a cleavage agent. It will be apparent that this structure of the hairpin will depend on the method used to promote its unfolding. In a representative example the portion of the nucleic domain forming the hairpin structure will be between from about 20 to about 1000 nucleotides in length, where in certain embodiments they may range from about 20 to about 500 nucleotides in length including from about 20 to about 250 nucleotides in length, e.g., from about 20 to about 160 nucleotides in length, such as from about 20 to about 150 nucleotides in length, from about 20 to about 130 nucleotides in length, from about 20 to about 110 nucleotides in length, from about 20 to about 90 nucleotides in length, from about 20 to about 80 nucleotides in length, from about 20 to about 75 nucleotides in length, from about 20 to about 70 nucleotides in length, from about 20 to about 60 nucleotides in length and any length between the stated ranges. Thus, the duplex part of the at least one hairpin structure may be at least 8 base pairs in length, preferably at least 9, 10, 11, 12, 13, 14, 15, 20, 25, 30, 40 or 50 base pairs in length. In other embodiments, the duplex part of the at least one hairpin structure of unfolding proximity probe may be at least 100, 200, 300 or 400 base pairs in length.

The single-stranded loop of the at least one hairpin structure preferably comprises at least 8 nucleotides, preferably at least 9, 10, 11, 12, 13, 14, 15, 20, 25, 30, 40 or 50 nucleotides. In other embodiments, the single-stranded loop of the at least one hairpin structure may be at least 100, 200, 300 or 400 nucleotides in length.

In preferred aspects of the invention the at least one hairpin structure of the nucleic acid domain of the unfolding proximity probes comprises at least one uracil residue, preferably at least 2, 3, 4, 5, 6, 7, 8, 9 or 10 uracil residues.

The nucleic acid domain of the proximity probes may be made up of ribonucleotides and/or deoxyribonucleotides as well as synthetic nucleotide residues that are capable of participating in Watson-Crick type or analogous base pair interactions. Thus, the nucleic acid domain may be DNA or RNA or any modification thereof e.g. PNA or other derivatives containing non-nucleotide backbones.

The sequence of the nucleic acid domain of the first and second proximity probes (i.e. the "detection" nucleic acid domains) may be chosen or selected with respect to the ligation template. In embodiments where the nucleic acid domains of the first and second proximity probes are complementary to a common ligation template (complementary to different regions of the same ligation template), i.e. when the nucleic acid domains are ligated to each other, the common ligation template may be provided on a third proximity probe. Thus, the sequence of the various nucleic acid domains is not critical as long as the first and second domains may interact, either directly or indirectly, e.g. they can hybridise to each other or a third nucleic acid domain (e.g. a ligation template). However, with the exception of the sequences required for the hairpin structures of the unfolding proximity probes, the sequences of the nucleic acid domains should be chosen to avoid the occurrence of hybridization events other than between the nucleic acid domains of the first and second proximity probes with that of the ligation templates. For example, the nucleic acids of the proximity probes should not be capable of hybridising to the gap/cassette oligonucleotide(s). Once the sequence of the nucleic acid domains is selected or identified, the nucleic acid domains may be synthesized using any convenient method.

The ligation template may be viewed as a "connector" oligonucleotide which acts to connect or "hold together" the nucleic acid domains of the first proximity probe, e.g. in embodiments where the nucleic acid domain ligates to itself to produce a circular ligation product. The ligation template may been seen as holding together the nucleic acid domains of the first and second (and in some embodiments, third) proximity probes, such they may interact, e.g. may be ligated together.

In particular the ligation template hybridises with the nucleic acid domains of the first and/or second proximity probes. More particularly, the ligation template hybridises (anneals) simultaneously with the nucleic acid domains of at least the first and/or second proximity probes. Where the ligation template is in the form of a nucleic acid domain of a third proximity probe the hybridisation of the nucleic acid domains of all of the set of proximity probes to each other increases the avidity of the probe-target complex upon binding to the target analyte. This avidity effect contributes to the sensitivity of the assay by supporting the formation of signal-giving proximity probe-target analyte complexes.

The term "hybridisation" or "hybridises" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity in a nucleic acid domain of a proximity probe refers to a portion of that nucleic acid domain that is capable of forming an intra- or intermolecular duplex, i.e. either a duplex within the same molecule (a hairpin structure) or a duplex with a different molecule. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule. In some embodiments the nucleic acid domains of the first and second proximity probes contain a region of complementarity for one or more ligation template oligonucleotides, and conversely the nucleic acid domain of the ligation template oligonucleotide contains regions of complementarity for each of the nucleic acid domains of the first and second proximity probes. In embodiments where the nucleic acid domain of the first proximity probe is a ligation template, the nucleic acid domain of the second proximity probe may contain two regions of complementarity for the nucleic acid domain of the first proximity probe, i.e. a region of complementarity at each end, 5' and 3', of the nucleic acid domain of the second proximity probe, such that the ends may be ligated directly or indirectly.

The regions of complementarity (i.e. hybridisation regions) may have a length in the range of 4-30 bp e.g. 6-20, 6-18, 7-15 or 8-12 bp.

The ligation template nucleic acid domain is generally of a length sufficient to provide for the above described simultaneous binding of nucleic acid domains of the first and second probes, of the two ends of a single probe. In representative embodiments, the ligation template oligonucleotides range in length from about 6 to about 500 nucleotides, including from about 20 to about 40 nucleotides, e.g. from about 25 to about 30 nucleotides.

As noted above, in a preferred embodiment described above, the interaction between the nucleic acid domains of the first and second proximity probes is a joining of the respective domains. This joining may preferably be a ligation, particularly a template-directed ligation. In such a case, it will clearly be understood that the ligation template will be provided by the ligation template (splint) oligonucleotide. Such a ligation may be carried out using a ligase enzyme.

Thus, in a preferred embodiment of the method of the invention, the nucleic acid domains of the first and second probes are ligatable by means of a reaction templated by the hybridised splint, said nucleic acid domains are ligated and the ligation product is detected. In such an embodiment, the splint may therefore be viewed as a "splint template" or "ligation template" or "template oligonucleotide".

For the interaction, or more particularly ligation, to take place, one of the nucleic acid domains of the first and second proximity probes will typically be coupled to the proteinaceous analyte-binding domain by its 5' end (leaving a free 3' hydroxyl end), while the other domain will be coupled via its 3' end (leaving a free 5' phosphate end). One of the first and second proximity probes will thus be a 5' probe having a free 3' hydroxyl group capable of interacting with the 5' phosphate of the other 3' probe.

To be ligatable, the respective first and second nucleic acid domains (either of the same probe or of different probes) hybridise to the ligation template with the 3' end of one lined up to the 5' phosphate of the other. However, as mentioned above and described in more detail elsewhere herein, the ligation of the respective domains need not be direct and they may be ligated together by means of an intermediary oligonucleotide, or whichever of the first or second proximity probe carries a free 3' nucleic acid domain end may be extended using a polymerase to fill the gap until the first and second nucleic acid domains can be joined by a ligation reaction. Thus, the respective 3' and 5' ends need not be hybridised immediately adjacent to one another on the splint (ligation and/or extension template) but may hybridise to the splint leaving a space (or a stretch of nucleotides) between them.

The hybridisation of the splint simultaneously to both nucleic acid domains of the first and second proximity (i.e. upon coincident binding of the nucleic acid domains of the proximity probes to the splint oligonucleotide) produces a stable duplexed structure that contains all three nucleic acid domains. For example, such a duplexed structure brings together the 3' hydroxyl free end of the nucleic acid domain of the first proximity probe and the 5' phosphoryl free end of the nucleic acid domain of the second proximity probe (although as mentioned above, these need not be immediately adjacently juxtaposed).

Thus, the ligation template (splint) may include a first 3' region of complementarity for the nucleic acid domain of the 5' free proximity probe and a second 5' region of complementarity for the nucleic acid domain of the 3' free proximity probe. The first and second regions of the splint may be 3 to 20, 6 to 17, 6 to 15 or 6 to 12 or 8 to 12 nucleotides in length, e.g. about 13 to 17, 12 to 16, 11 to 15, or 12 to 14 nucleotides in length or about 6 to 12, 7 to 11 or 8 to 10 nucleotides in length.

As will be described in more detail below, amplification of the interaction (e.g. ligation) product may be used as part of the detection process. Accordingly, it may in some embodiments be desirable to design the splint so as to minimise any false amplification which may take place in such a step, for example any possibility of the splint acting as a template for the polymerase used in the amplification.

Thus for example the splint may be provided as an RNA oligonucleotide or a DNA/RNA hybrid; Taq polymerase typically used in amplification reactions cannot use an RNA template. Alternatively, a similar effect may be achieved using a DNA splint with two short hybridisation regions; since the hybridisation is weak, such a splint will not template DNA polymerisation at the high temperatures used in PCR.

As mentioned above, in one embodiment, the nucleic acid domains of the first and second probes may hybridise to the splint not immediately adjacent to each other, but to leave a gap between them. To enable their conjugation (e.g. ligation) a further oligonucleotide, referred to herein as a "gap" or "cassette" oligonucleotide, may hybridise to the splint in this gap, more particularly to span this gap. Such a gap/cassette oligonucleotide may be hybridised with each of its ends directly adjacent to the end of each of the respective domains, such that each such domain end may be ligated to the gap/cassette oligonucleotide to form a single new nucleic acid product. This requires two ligation events, both of which are templated by the splint. Both the 5' and the 3' end of the gap/cassette oligonucleotide are joined (ligated) to the free end of the nucleic acid domain of the first and second probe, as appropriate. The first and second domains are thus connected, or joined, via the gap/cassette oligonucleotide. Such an arrangement may add flexibility to the nucleic acid domains of the probes. The gap oligonucleotide, may as discussed above, be used to introduce a marker or identification sequence e.g. a barcode. As depicted in FIG. 13 the use of a gap oligonucleotide with a non-complementary sequence between complementary ends may facilitate the introduction of one or more, or longer, such marker sequences. The length of the gap/cassette oligonucleotide (and hence the gap between the ends of the first and second domains when hybridised to the splint) may vary, for example between 4 to 50, eg. 6-30, 6-25, 6-22, 8-22, 10-22, 6-20, 8-20, 10-20 nucleotides.

The gap/cassette oligonucleotide, which functions as an intermediary oligonucleotide in the ligation of the first and second nucleic acid domains, may be added after the probes have been contacted with the sample. Alternatively, it may be added at the same time or it could be pre-hybridized to the splint oligonucleotide.

The gap may also be filled by extending the nucleic acid domain of whichever of the first or second proximity probe carries a free 3' end, using a polymerase. Once the gap has been filled, the ends are joined by a ligation step.

To carry out the method of the invention, the sample may be contacted with a blocking reagent prior to contact with at least one set of probes to reduce non-specific proximity probe interactions.

In certain embodiments a sample may be assayed for two or more different target analytes. In such embodiments, the sample is contacted with a set of proximity probes for each target analyte, such that the number of sets contacted with the sample may be two or more, e.g., three or more, four or more etc. Such methods find particular use in multiplex and high-throughput applications. In this respect, the methods of the invention are particularly advantageous for the detection of multiple analytes in a sample, both in homogeneous and heterogeneous formats. In some embodiments, e.g. for the detection of highly mutable analytes such as viral sequences, multiple probe sets may be used for the same analyte (e.g. transcript) to optimise the efficiency of the detection. In other representative embodiments, the analyte-binding domain may be designed to encompass tolerance for some mismatches, e.g. the where the analyte-binding domain and analyte are both nucleic acids the sequences do not need to be 100% complementary, e.g. the sequences may share at least 85, 90 or 95% sequence identity.

The amount of proximity probes that is added to a sample may be selected to provide a sufficiently low concentration of proximity probe in the reaction mixture to ensure that the proximity probes will not randomly come into close proximity with one another in the absence of binding to a target analyte, at least not to any great or substantial degree. As such, it is intended that only when the proximity probes bind the analyte through the binding interaction between the analyte-binding domains of the proximity probes and the binding sites of the analyte, do the proximity probes come into close proximity to one another (i.e. upon coincident binding of the proximity probes to the analyte). In representative embodiments, the concentration of the proximity probes in the reaction mixture following combination with the sample ranges from about 1 fM to 1 µM, such as from about 1 µM to about nM, including from about 1 µM to about 100 nM.

Following combination of the sample and set(s) of proximity probes, the reaction mixture may be incubated for a period of time sufficient for the proximity probes to bind target analyte, if present, in the sample. As described above, once the proximity probes have bound to the analyte the unfolding proximity probe(s) in the sample are "unfolded", by cleavage and any other appropriate mechanism, to allow at least the nucleic acid domains of the proximity probes to interact, i.e. the nucleic acid domains of the proximity probes bound to the analyte and in proximity to each other. Where more than one type of unfolding proximity probe is used in the assay, each different type of unfolding probe may be "unfolded" separately, e.g. the first set of probes may be unfolded by cleavage and the second set of proximity probes may be unfolded by subsequently altering the conditions of the sample to promote unfolding. In some embodiments, the proximity probes may be contacted with the sample in more than one step. Thus, one or more unfolding proximity probes may be contacted with the sample and allowed to interact with the analyte (in the case of horn probes, this may involve a ligation reaction). The unfolding proximity probes are "unfolded" and then additional proximity probes, which may be unfolding proximity probes, are contacted with the sample. Hence, the proximity probes may be contacted with the sample in one, two, three or more stages. In a particularly preferred embodiment, the proximity probes are contacted with the sample at the same time. In some representative embodiments, e.g. in situ assays or other assays in which the analyte is immobilised, wash steps may be included between the addition of different proximity probes, or between adding the proximity probes and unfolding the nucleic acid domain(s) of the probes, or more particularly before the cleavage step, e.g. the analyte may be captured by a probe immobilised on a substrate, which may be washed to remove unbound or non-specifically bound analyte or sample followed by the addition of other proximity probes, see e.g. FIGS. 21 and 22. Alternatively, or additionally, a washing step may be included after the proximity probes have been added to the sample and allowed to bind, but before the unfolding or cleavage step.

In representative embodiments, the (unfolding) proximity probes and sample may be pre-incubated for a period of time ranging from 5 minutes to about 24 hours prior to the addition of the proximity probes. Preferably said pre-incubation is from about 20 minutes to 12 hours at a temperature ranging from 4 to about 50° C., preferably at room temperature, e.g. 18-30° C. Conditions under which the reaction mixture is maintained should be optimized to promote specific binding of the proximity probe to the analyte, while suppressing unspecific interaction.

Following pre-incubation, if such a step is included, nucleic acid domains of the unfolding proximity probes are unfolded and the product mixture may be incubated for a period of time ranging from about 5 minutes to about 48 hours, including from about 30 minutes to about 12 hours, at a temperature ranging from about 4 to about 50° C., including from about 20 to about 37° C. Conditions should allow for efficient and specific hybridization between the nucleic acid domains as described above.

In certain embodiments, the effective volume of the incubation mixture is reduced, at least during the portion of the incubation step in which the proximity probes are binding to target analyte, if present in the sample. In these embodiments, the effective volume of the incubation mixture may be reduced for a number of different reasons. In certain embodiments, the effective volume of the incubation mixture is reduced in order to allow for the use of medium and low affinity analyte-binding domains and/or increase the sensitivity of the assay. For example, in certain embodiments where the effective volume of the incubation mixture is reduced, the analyte-binding domains may be medium or low affinity binders, by which is meant that the analyte-binding domains may have a binding affinity for their target analyte that is less than about $10^{-4}$ M, such as about 1 mM $K_d$. In certain embodiments, the sensitivity of the assay may be increased such that the assay can detect as few as about 100 or fewer target analytes in a 1 µl sample, including as few as about 75 or fewer target analytes in a 1 µl sample, including as few as about 50 or fewer target analytes in a 1 µl sample.

In certain embodiments, a "crowding agent" or "volume excluder" is included in the mixture during the incubation step reviewed above, e.g., to reduce the effective volume of the incubation mixture during binding of the proximity probes to their target analyte. Typically, the "crowding agent" is a water soluble macromolecular material. Suitable macromolecular materials broadly comprise biocompatible natural or synthetic polymers having an average molecular weight of from about 1500 to several million, which do not specifically interact with the other reagents in the mixture, or the product. Such polymers are known in the art as "volume-excluders", as their primary function is to occupy volume in the in vitro reaction medium and provide a highly concentrated environment for biochemical reactions, e.g., approximating in vivo conditions. The volume-excluding polymers must of course be sufficiently soluble to provide the required concentration. Suitable exemplary polymers include, but are not limited to: commercially available polyethylene glycol (PEG) polymers, e.g., having an average molecular weight greater than about 2000, FICOLL polymers such as those having an average molecular weight of about 70,000, bovine plasma albumin, glycogen, polyvinylpyrrolidone, dextran, etc. PEG polymers of higher molecular weights, especially, PEG 1450, PEG 3350, PEG 6000 (also sold as PEG 8000), and PEG 20,000, having average molecular weights of about 1450, 3000-3700, 6000-7500, and 15,000-20,000, respectively, are employed in representative embodiments. PEG 6000 and PEG 8000 are employed in representative embodiments. The concentration of the volume-excluding polymers in the incubation reaction in representative embodiments falls within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

In those embodiments where a volume excluder is employed, prior to the next step of the method, the incubation mixture may be diluted to account for the presence of the volume excluder, e.g., by at least about 2-fold or more, such as at least about 5-fold or more, including at least about 10-fold or more, depending on the amount of volume excluder that is present, the nature of the dilution fluid, etc., where in representative embodiments the dilution fluid is water or some other suitable aqueous fluid of water and one or more solutes, e.g., salts, buffering agents, etc.

Instead of, or in addition to, the use of a volume excluder, the incubation mixture may be reduced in volume during incubation by removing a portion of the water from the incubation mixture, e.g., via evaporation. In these embodiments, the volume of the fluid may be reduced by at least about 2-fold or more, such as at least about 5-fold or more, including at least about 10-fold or more, as desired. Importantly, not all of the water is removed from the incubation mixture in these embodiments. Any convenient protocol may be employed for reducing the volume of the incubation mixture by removing a select portion of the water therefrom. An instrument for controlling evaporation rate by monitoring and adjusting humidity and temperature may be employed, where in certain embodiments the volume of the incubation mixture is monitored, e.g., by continuously measuring the volume of the incubation mixture, where when appropriately evaporated, the ligation and PCR-mixes may be added, as described above. As desired, a heating block could be used to enhance the evaporation. Alternatively, the volume of the incubation mixture may be reduced by filtrating out water. In representative embodiments, a size exclusion filter is used to selectively contain molecules of sizes larger than a cut off limit while smaller molecules and water is removed by passage through the filter. The force placed on the solution to move it through the filter may be by either centrifugation or vacuum suction.

Upon binding of the analyte-binding domains of the proximity probes to the analyte, the nucleic acid domains of the proximity probes come into close proximity to one another. However, the nucleic acid domains will not be capable of interacting until the unfolding proximity probes have been "unfolded". Once unfolding has been achieved the ligation template oligonucleotide, if used, is able to bind (hybridise) to, e.g. the nucleic acid domain of the first and second probes.

Following the combination of the sample with the proximity probes, the gap/cassette oligonucleotide(s) may be added, if used, and allowed to hybridise. Alternatively or additionally, one or more gap oligonucleotides may be added with the proximity probes. In some embodiments, the gap oligonucleotides may be prehybridized to the ligation template. As described above, in some embodiments the nucleic acid domains of the first and second probes, which may be hybridised to the splint, are then joined together by nucleic acid ligation of the free 3' hydroxyl and 5' phosphate ends of the nucleic acid domains of the first and second proximity probes. The reaction mixture is then assayed for the presence of the interaction. Thus, ligation of the first and second nucleic acid domains is detected, generally by detecting the ligation product thereof. It will be evident from the above examples, that the ligation may be between two regions of the same nucleic acid domain or may include the ligation of a nucleic acid domains of a third proximity probe.

In general, any convenient protocol that is capable of detecting the presence of proximity dependent interactions may be employed. The detection protocol may or may not require a separation step.

In these representative embodiments, ligation of the splint stabilised nucleic acid domains of the proximity probes is achieved by contacting the reaction mixture with a nucleic acid ligating activity, e.g. provided by a suitable nucleic acid ligase, and maintaining the mixture under conditions sufficient for ligation of the nucleic acid domains to occur.

As is known in the art, ligases catalyze the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a template). Any convenient ligase may be employed, where representative ligases of interest include, but are not limited to: Temperature sensitive and thermostable ligases. Temperature sensitive ligases include, but are not limited to, bacteriophage T4 DNA ligase, bacteriophage T7 ligase, and E. coli ligase. Thermostable ligases include, but are not limited to, Taq ligase, Tth ligase, Ampligase® and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

In this ligation step, a suitable ligase and any reagents that are necessary and/or desirable are combined with the reaction mixture and maintained under conditions sufficient for ligation of the hybridized ligation oligonucleotides to occur. Ligation reaction conditions are well known to those of skill in the art. During ligation, the reaction mixture in certain embodiments may be maintained at a temperature ranging from about 4° C. to about 50° C., such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. In a representative embodiment, the ligation reaction mixture includes 50 mM Tris pH7.5, 10 mM $MgCl_2$, 10 mM DTT, 1 mM ATP, 25 mg/ml BSA, 0.25 units/ml RNase inhibitor, and T4 DNA ligase at 0.125 units/ml. In yet another representative embodiment, 2.125 mM magnesium ion, 0.2 units/ml RNase inhibitor; and 0.125 units/ml DNA ligase are employed.

It will be evident that the ligation conditions may depend on the ligase enzyme used in the methods of the invention. Hence, the above-described ligation conditions are merely a representative example and the parameters may be varied according to well known protocols. For example, a preferred ligase of the methods of the invention, namely Ampligase®, may be used at temperatures of greater than 50° C. However, it will be further understood that the alteration of one parameter, e.g. temperature, may require the modification of other conditions to ensure that other steps of the assay are not inhibited or disrupted, e.g. binding of the proximity probe to the analyte. Such manipulation of the proximity assay methods is routine in the art.

Following ligation, the ligation products (ligated nucleic acid domains of the proximity probes) are detected as an indication of the presence, or as a measure of the amount and optionally the location, of analyte in the sample. In these embodiments, the ligated product comprises a single stranded nucleic acid molecule (which is the product of the ligation of the two proximal nucleic acid domains of at least the first and/or second probes, and any intermediary gap/cassette oligonucleotide(s), if used). In some embodiments, the single stranded nucleic acid molecule may terminate at each end in an analyte binding domain. In other embodiment, the single stranded nucleic acid molecule may be a circular molecule, which may be hybridised to the nucleic acid domain of one or more proximity probes.

The next step of the method following ligation step is to determine the presence of the ligated product in the reaction mixture in order to detect the target analyte in the sample. In other words, the reaction mixture is screened etc. (i.e., assayed, assessed, evaluated, tested, etc.) for the presence of any resultant ligation products in order to detect the presence of the target analyte in the sample being assayed.

The ligated product produced by the above-described methods may, in the broadest sense, be detected using any convenient protocol. The particular detection protocol may vary depending on the sensitivity desired and the application in which the method is being practiced. In certain embodiments, the nucleic acid ligation product may be directly detected without any amplification, while in other embodiments the detection protocol may include an amplification component, in which the copy number of the ligated product nucleic acid is increased, e.g., to enhance sensitivity of the particular assay. Where detection without amplification is practicable, the nucleic acid ligation product may be detected in a number of different ways. For example, one or more of the nucleic acid domains of the proximity probes may be directly labelled, e.g., fluorescently, or otherwise spectrophotometrically, or radioisotopically labelled or with any signal-giving label, such that the ligation product is directly labelled. In these embodiments, the directly labelled ligation product may be size separated from the remainder of the reaction mixture, including unligated directly labelled ligation oligonucleotides (i.e. nucleic acid domain oligonucleotides or gap/cassette oligonucleotides), in order to detect the ligated nucleic acid. Alternatively, conformationally selective probes, e.g., molecular beacons (as described in greater detail below) may be employed to detect to the presence of the ligation product, where these probes are directed to a sequence that spans the ligated nucleic acids and therefore only exists in its entirety in the ligation product.

As indicated above, in certain embodiments of the subject methods, the detection step includes an amplification step, where the copy number of ligated nucleic acids is increased, e.g., in order to enhance sensitivity of the assay. The amplification may be linear or exponential, as desired, where representative amplification protocols of interest include, but are not limited to: polymerase chain reaction (PCR); isothermal amplification, rolling-circle amplification (RCA) etc.

Where the detection step includes an amplification step (more specifically a step of in vitro amplification of the conjugated product), the amplified product (or amplification product) may be detected, to detect the analyte.

The polymerase chain reaction (PCR) is well known in the art, being described in U.S. Pat. Nos. 4,683,202; 4,683,195; 4,800,159; 4,965,188 and 5,512,462, the disclosures of which are herein incorporated by reference. In representative PCR amplification reactions, the reaction mixture that includes the above ligated nucleic acids or ligation product (which may also be viewed as a template nucleic acid in an amplification reaction) is combined with one or more primers that are employed in the primer extension reaction, e.g., the PCR primers (such as forward and reverse primers employed in geometric (or exponential) amplification or a single primer employed in a linear amplification). The oligonucleotide primers with which the template nucleic acid (hereinafter referred to as template DNA for convenience) is contacted will be of sufficient length to provide for hybridization to complementary template DNA under annealing conditions (described in greater detail below). The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers (forward and reverse primers), depending on whether primer extension, linear or exponential amplification of the template DNA is desired. In some embodiments, the primer(s) may be provided as a nucleic acid domains of a proximity probe. In other embodiments, the ligation template may also act as a primer.

In addition to the above components, the reaction mixture produced in the subject methods typically includes a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in Barnes et al, Proc. Natl. Acad. Sci USA (1994) 91:2216-2220); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) as described in Perler et al., Proc. Natl. Acad. Sci. USA (1992) 89:5577-5581; *Pyrococcus* species GB-D (Deep Vent); *Pyrococcus furiosus* DNA polymerase (Pfu) as described in Lundberg et al., Gene (1991) 108:1-6, *Pyrococcus woesei* (Pwo) and the like. Where the reaction mixture includes both a Family A and Family B polymerase, the Family A polymerase may be present in the reaction mixture in an amount greater than the Family B polymerase, where the difference in activity will usually be at least 10-fold, and more usually at least about 100-fold. Usually the reaction mixture will include four different types of dNTPs corresponding to the four naturally occurring bases present, i.e. dATP, dTTP, dCTP and dGTP. In the subject methods, each dNTP will typically be present in an amount ranging from about 10 to 5000 μM, usually from about 20 to 1000 μM.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, $NH_4$-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^2$ present in the buffer may range from 0.5 to 10 mM, but will preferably range from about 3 to 6 mM, and will ideally be at about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

Rolling-circle amplification (RCA) is well known in the art, being described in Dean et al., 2001 (Rapid Amplification of Plasmid and Phage DNA Using Phi29 DNA Polymerase and Multiply-Primed Rolling Circle Amplification, *Genome Research*, 11, pp. 1095-1099), the disclosures of which are herein incorporated by reference. In representative RCA reactions, the reaction mixture that includes the above ligated, i.e. circularised nucleic acids or ligation product (which may also be viewed as a template nucleic acid in an amplification reaction) is combined with one or more primers that are employed in the primer extension reaction, e.g., RCA may be templated by a single primer to generate a single concatameric product or multiple primers, each annealing to a different region of the circular oligonucleotide to produce multiple concatameric products per circle. The oligonucleotide primers with which the template nucleic acid is contacted will be of sufficient length to provide for hybridization to complementary template DNA under annealing conditions (described in greater detail below). The primers for RCA can be defined similarly to those for PCR, as described above. In some embodiments, the primer(s) may be provided as a nucleic acid domain of proximity probe. In other embodiments, the ligation template may also act as a primer.

In addition to the above components, the reaction mixture produced in the subject methods typically includes a polymerase, e.g. phi29 DNA polymerase and other components required for a DNA polymerase reaction as described above. The desired polymerase activity may be provided by one or more distinct polymerase enzymes.

In preparing the reaction mixture of this step of the subject methods, the various constituent components may be combined in any convenient order. For example, the buffer may be combined with primer, polymerase and then template DNA, or all of the various constituent components may be combined at the same time to produce the reaction mixture.

The amplified products of the amplification reaction may be detected using any convenient protocol, where the particular protocol employed may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-amino-actinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled probe nucleic acids are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled probe nucleic acid, e.g., oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence (e.g. a barcode sequence) found in the amplification product of interest (as described above), e.g., under stringent hybridization conditions (as defined above). This target binding domain typically ranges in length from about 10 to about 60 nucleotides, usually from about 15 to about 30 nt. Depending on the nature of the oligonucleotide and the assay itself, the target binding domain may hybridize to a region of the template nucleic acid or a region of the primer extension product. For example, where the assay is a 5' nuclease assay, e.g., in which a TaqMan® type oligonucleotide probe is employed, the target binding domain hybridizes under stringent conditions to a target binding site of the template nucleic acid, which is downstream or 3' of the primer binding site. In alternative embodiments, e.g., in molecular beacon type assays, the target binding domain hybridizes to a domain of a primer extension product. The overall length of the energy transfer labelled oligonucleotides employed in these embodiments, which includes all three domains mentioned above, typically ranges from about 10 to about 60 nucleotides, usually from about 15 to about 30 nucleotides.

In certain embodiments, the energy transfer labelled oligonucleotide is structured such that energy transfer occurs between the fluorophore and acceptor of the energy transfer labelled oligonucleotide probe upon fluorophore excitation when the energy transfer labelled oligonucleotide is not hybridized to target nucleic acid.

In certain embodiments, the oligonucleotide is a single stranded molecule that does not form intramolecular structures and in which energy transfer occurs because the spacing of the donor and acceptor provides for energy transfer in the single stranded linear format. In these embodiments, energy transfer also occurs between the fluorophore and acceptor of labelled oligonucleotide probe upon fluorophore excitation when the labelled oligonucleotide probe is hybridized to a target nucleic acid. Specific examples of such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). In many of these embodiments, the target nucleic acid binding domain is one that hybridizes to, i.e. is complementary to, a sequence of the template nucleic acid, i.e. the target nucleic acid of the target nucleic acid binding domain is a sequence present in the template nucleic acid (i.e., the pseudotarget or surrogate nucleic acid).

In other embodiments, the probe oligonucleotides are structured such that energy transfer does not occur between the fluorophore and acceptor of the energy transfer labelled oligonucleotide probe upon fluorophore excitation when the energy transfer labelled oligonucleotide probe is hybridized to a target nucleic acid. Examples of these types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference). In many of these embodiments, the target binding sequence or domain comprises a hybridization domain complementary to a sequence of the primer extension product of the amplification reaction, and not to a sequence found in the pseudotarget nucleic acid.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid via detection of the pseudotarget nucleic acid and/or amplification products thereof. Depending on the particular label employed, detection of a signal may indicate the presence or absence of the target nucleic acid.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample on a microscope slide, fluorescence may be detected using a fluorescence microscope. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target analyte present in the sample, e.g., as correlated to the amount of amplification product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of target analyte(s). The methods are suitable for detection of a single target analyte as well as multiplex analyses, in which two or more different target analytes are assayed in the sample. In these latter multiplex situations, the number of different sets of probes that may be employed typically ranges from about 2 to about 20 or higher, e.g., as up to 100 or higher, 1000 or higher, etc. wherein the multiple analytes in a sample may be detected in parallel or sequentially.

The analysis of many analytes simultaneously and in a single reaction using several different proximity probe sets (multiplexing) is enhanced by the increased specificity and sensitivity obtained when using the unfolding proximity probes of the invention. Each probe set can be designed to produce a unique interaction (e.g. ligation) product that can be used to determine the presence or absence, quantity and/or location of the analytes being interrogated by the probe set. The interaction product may be detected directly or after amplification using any of the well established methods for analysis of nucleic acid molecules known from the literature including liquid chromatography, electrophoresis, mass spectrometry, microscopy, real-time PCR, fluorescent probes etc. Of particular interest is the combination of the methods described herein with a "DNA array" readout format. Several unique interaction products from a multiplexed proximity assay may be hybridized to a standardized DNA array carrying a number of oligonucleotide sequences (tags) complementary to the ligation product sequences. Each interaction product hybridized to the array may be identified by its location on the DNA array and the detected intensity in a given hybridization spot will be indicative of the quantity of that specific interaction product and hence also of the analyte giving rise to that interaction product. Detection of the interaction products may be accomplished by spectrometry, fluorescence, radioisotopes etc. Fluorescent moieties may conveniently be introduced into the interaction products using fluorescently labelled primers or fluorescently labelled nucleotides in the amplification reaction (PCR). The DNA array may be a simple dot-blot array on a membrane containing a small number of spots or a high density array carrying hundreds of thousands of spots.

The detection step of the method of the invention may be modified in order to further reduce the background associated with non-specific nucleic acid hybridization events. Such modifications include adjustments to the method that will reduce any non-specific nucleic acid hybridization events. In some embodiments, a protein may be added to the mixture containing the sample and the proximity probes in order to reduce weak and non-specific DNA hybridization events. For example, E. coli single strand DNA binding protein has been used to increase the yield and specificity of primer extension reactions and PCR reactions. (U.S. Pat. Nos. 5,449,603 and 5,534,407.) The gene 32 protein (single strand DNA binding protein) of phage T4 apparently improves the ability to amplify larger DNA fragments (Schwartz, et al., Nucl. Acids Res. 18: 1079 (1990)) and enhances DNA polymerase fidelity (Huang, DNA Cell. Biol. 15: 589-594 (1996)). When employed, such a protein will be used to achieve a concentration in the reaction mixture that ranges from about 0.01 ng/µL to about 1 µg/µL; such as from about 0.1 ng/µL to about 100 ng/µL; including from about 1 ng/µL to about 10 ng/µL.

As explained above, the method of the invention is designed such that interaction between the nucleic acid domains of the proximity probes (e.g ligation) should occur only if the proximity probes are bound to the analyte and after the unfolding proximity probes have been "unfolded". However, as is the case with all assays of this type, this cannot always be guaranteed and there may be some background interaction, e.g. ligation of the nucleic acid domains of "standard" proximity probes used in the assay, if the probes come into proximity randomly in solution. The possibility of this is reduced by requiring the nucleic acid domains of all the probes to hybridise in juxtaposition to one another by means of the ligation template oligonucleotide, in order for such interaction to occur. Similarly, the possibility of background interaction is reduced where more than one proximity probe is an unfolding proximity probe, i.e. at least one proximity probe is an unfolding proximity probe, preferably two, three, four or more. Thus, to further reduce or minimise the possibility of background due to unreacted (i.e. unbound) probes, blocking oligonucleotides may be used in addition to the unfolding proximity probes as described above.

The blocking oligonucleotides bind (i.e. hybridise or anneal) to the free ends of the nucleic acid domains of the "standard" proximity probes. Thus a blocking oligonucleotide may bind to the free 3' OH end of the nucleic acid domain of a 5' proximity probe and to the free 5' phosphate end of the nucleic acid domain of a 3' proximity probe. The binding of the blocking oligonucleotide may be out-competed in the presence of a high concentration of an anti-blocking oligonucleotide, which may be, e.g. the ligation template. In embodiments where the ligation template is an anti-blocking oligonucleotide, when all the probes are bound together on the analyte the ligation template can be seen as being in a high local concentration and therefore is capable of binding to the nucleic acid domain of the proximity probe(s) in preference to the blocking oligonucleotide. In this way the blocking oligonucleotide may prevent the nucleic acid domains from hybridising to the ligation template in the absence of analyte binding. Thus the free ends of the "standard" proximity probes may be prevented from interaction in the absence of binding to the analyte. When all the probes are bound to the analyte, the local concentration of the anti-blocking oligonucleotide, e.g. splint, especially when the splint forms the nucleic acid domain of proximity probe, is sufficient to out-compete the blocking oligonucleotides; the nucleic acid domains hybridise to the splint and the blocking oligonucleotides are replaced.

The blocking oligonucleotides thus allow a competition-based strategy to be used to reduce background and thus further increase sensitivity of the assay.

The blocking oligonucleotides may range in length from about 4-100 nucleotides, e.g. 6-75 or 10-50. They may hybridise to a region at or near the free end of the nucleic acid domain of the first or second probe ("near" meaning within 1-20 or 1-10, e.g. 1-6 nucleotides of the free 3' or 5' end). The region of hybridisation may be 3-15 nucleotides long e.g. 3-12, 3-10, 3-8, 4-8, 3-6, 4-6.

The blocking oligonucleotides may conveniently be designed to have a hairpin structure such that the blocking oligonucleotide may be ligated to the end of proximity probes which have failed to hybridise to the splint.

The blocking oligonucleotides are typically used in an excess over the respective probes, e.g. an excess of 2-1000 fold, e.g. 20-500, 50-300, 100-500, or 100-300 fold e.g., 20, 200 or 300 fold.

In the case of detecting an analyte with proximity-probes of low affinity and slow binding kinetics, the proximity-probes may be contacted with the sample and incubated at a sufficiently high concentration to promote binding of the proximity probes to the analyte. This incubation step may be quickly diluted in a large volume of cold buffer (e.g., buffer that does not include the analyte or the proximity probes), and a portion of this dilution subsequently added to a ligation reaction mixture. This ligation reaction mixture may contain the gap/cassette oligonucleotide(s) (if used), ATP and ligase enzyme. The low temperature, e.g., ranging from about 0° C. to about 20° C., including from about 4° C. to about 10° C., minimizes the dissociation of existing proximity-probe-analyte complexes while the vast dilution results in a decrease of the concentration of the unbound proximity-probes, thereby lowering their reactivity and minimizing the background signal.

In such embodiments, the assay is performed by using a small incubation volume of from about 1 μl to about 20 μl, such as about 1 μl, or about 2 μl, or about 3 μl, or about 4 μl, or about 5 μl or about 6 μl, of sample and proximity probes and then adding the gap/cassette in a larger incubation volume of from about 8 μl to about 1.5 ml or more, such as from about 20 μl to about 1.3 ml, such as from about 50 μl to about 1 ml, such as from about 75 μl to about 800 μl, such as from about 100 μl to about 500 μl, such as from about 200 μl to about 300 μl. The effective concentration of the proximity probes in the final incubation volume is thus diluted, reducing the background while maintaining the signal since the binding between the probes and analyte does not have time to dissociate before the nucleic acid domains are ligated. This approach enables extremely high sensitivity as long as the ligation products can be concentrated from the larger volumes, such as over 100 μl or more, and then detecting the proximity dependent interaction. In such embodiments, the probe-probe interactions can be reduced by using single strand binding proteins.

Problems associated with complex samples may be further addressed by diluting the complex sample prior to the analysis. Dilution of complex samples may, in combination with the unfolding proximity probes of the present invention, further reduce the background signal. In essence, the step of diluting the sample will greatly decrease the amount of proteins the probes may bind unspecifically to thereby lowering concentration of probes required. While the analyte will also be diluted, the high sensitivity of the proximity probing will provide good detection and quantification.

The method of the present invention may be employed homogeneously (i.e. in solution) as described above, or alternatively heterogeneously, using a solid phase, for example, in which analyte becomes immobilised on a solid phase, permitting the use of washing steps. The use of solid phase assays offers advantages, particularly for the detection of difficult samples: washing steps can assist in the removal of inhibiting components, and analytes can be enriched from an undesirably large sample volume. Higher concentrations and greater amounts of proximity probes can be used, as unbound analytes and probes can be removed by washing. The ability to remove unbound probes, or probes which have not interacted, by washing also means that the solid phase assay tolerates lower purity proximity probes by comparison with the homogeneous assay. In some embodiments, washing steps may be performed in between the addition of proximity probes, e.g. if the probes are added to the sample in stages or after addition of the probes and before the unfolding/cleavage step.

Immobilisation of the analyte on a solid phase may be achieved in various ways. Accordingly, several embodiments of solid phase proximity probe assays are contemplated. In one such embodiment, one (or more) of the first or second (or third, if used) proximity probes may be (or may be capable of being) immobilised on a solid phase (or solid support). The analyte can firstly be captured by the one (or more) immobilised (or immobilisable) probes and secondly be bound by subsequently added probe(s).

The immobilised proximity probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the probe may be directly bound to the support, for example via the analyte-binding domain (e.g. chemically crosslinked), it may be bound indirectly by means of a linker group, or by an intermediary binding group(s) (e.g. by means of a biotin-streptavidin interaction). Thus, a proximity probe may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support. The probe may be immobilised before or after binding to the analyte. Further, such an "immobilisable" probe may be contacted with the sample together with the support.

The solid support may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps.

In another embodiment, an immobilised (or immobilisable) analyte-specific probe comprising only a binding domain (i.e. an analyte capture probe) can be used in addition to the non-immobilised proximity probes of the homogeneous binding splint assay. Thus in such an embodiment the analyte is first captured by the immobilised or immobilisable capture probe which serves only to immobilise the analyte on the solid phase, and subsequently the immobilised analyte is incubated with the proximity probes. In such an embodiment, the capture probe may be any binding partner capable of binding the analyte, directly or indirectly (e.g. as discussed above in relation to the analyte-binding domain of the proximity probe). More particularly, such a capture probe binds specifically to the analyte. Since this embodiment of the method requires the simultaneous binding of at least three probes (binding domains) to the analyte or analyte complex, potentially at least three different epitopes can be interrogated, conferring high specificity on the assay.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

The above-described methods result in detection of proximity dependent interactions that are present in the reaction mixture, which in turn provides a measure of the amount of target analyte in the sample being assayed. The measure may be qualitative or quantitative.

Accordingly, the above described methods of detecting the presence of one or more target analytes in a complex sample finds use in a variety of different applications.

The subject methods may be used to screen a sample for the presence or absence of one or more target analytes in a sample. As indicated above, the invention provides methods of detecting the presence or quantifying the amount of one or more target analytes in a sample.

The subject methods can be employed to detect the presence of one or more target analytes in a variety of different types of samples, including complex samples having large amounts of non-target entities, where the unfolding proximity probes of the subject methods allows for superior detection of the target analytes(s) over equivalent methods that do not utilise the unfolding proximity probes of the invention. As such, the subject methods are highly sensitive methods of detecting one or more target analytes in a simple or complex sample. The sample that is assayed in the subject methods is, in many embodiments, from a physiological source, as discussed in more detail above.

In addition to detecting a wide variety of analytes, the subject methods may also be used to screen for compounds that modulate the interaction between the analyte binding domain of the proximity probe with the binding region of the analyte i.e. the binding of the analyte-binding domain to the analyte. The term modulating includes both decreasing (e.g., inhibiting) and enhancing the interaction between the two molecules. The screening method may be an in vitro or in vivo format, where both formats are readily developed by those of skill in the art.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents identified in the above screening assays find use in the a variety of methods, including methods of modulating the activity of the target analyte, and conditions related to the presence and/or activity thereof.

Also provided are kits that find use in practicing the subject methods, as mentioned above. For example, in some embodiments, kits for practicing the subject methods include at least one set of first and second proximity probes, which probes each comprise an analyte-binding domain and a nucleic acid domain, wherein at least one of said proximity probes is an unfolding proximity probe, wherein the nucleic acid domain comprises a hairpin structure that can be cleaved to generate a ligatable free end or a region of complementarity to another nucleic acid molecule, as described above. Said kits may further comprise at additional, e.g. third, fourth etc. proximity probes, as described above. As indicated above, certain protocols will employ two or more different sets of such probes for simultaneous detection of two or more target analytes in a sample, e.g., in multiplex and/or high throughput formats. As such, in certain embodiments the kits will include two or more distinct sets of proximity probes. Furthermore, additional reagents that are required or desired in the protocol to be practiced with the kit components may be present, which additional reagents include, but are not limited to one or more of the following: means for unfolding the proximity probes (e.g. an enzyme or combination of enzymes such as a nickase, restriction endonuclease or uracil-DNA glycosylase enzyme and endonuclease, e.g. endonuclease IV), a ligase, gap/cassette oligonucleotide, ligatable oligonucleotides, blocking oligonucleotides, solid support for immobilisation of probe, binding domain or analyte, means for immobilisation of probe, binding domain or analyte, detection means e.g. fluorescently labelled nucleotides or oligonucleotides, pairs of supplementary nucleic acids, single strand binding proteins, and PCR amplification reagents (e.g., nucleotides, buffers, cations, etc.), and the like. In certain embodiments, the kits may include elements employed in reducing the effective volume of an incubation mixture, as reviewed above, e.g., a volume excluder. The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Accordingly, in a further aspect the present invention provides a kit for use in method for detecting an analyte in a sample, said kit comprising:

(a) at least one set of at least first and second proximity probes, which probes each comprise an analyte-binding domain and a nucleic acid domain and can simultaneously bind to the analyte directly or indirectly, wherein the nucleic acid domain of at least one of said proximity probes comprises a hairpin structure that can be cleaved to generate at least one ligatable free end or region of complementarity to another nucleic acid molecule in said sample, which allows the nucleic acid domains of said at least first and second proximity probes to interact, directly or indirectly;

(b) optionally, means for mediating the interaction between the nucleic acids of said first and second proximity probes (e.g. a common template, for example a ligation template oligonucleotide, and/or a ligase enzyme);

(c) optionally, means for unfolding the at least one proximity probe comprising a hairpin structure (e.g. enzymatic means such as a nickase, restriction endonuclease or uracil-DNA glycosylase enzyme and endonuclease, e.g. endonuclease IV); and (d) optionally, means for detecting said interaction.

As indicated above, the means for mediating the interaction between the nucleic acids may include one or more ligation template (splint) oligonucleotides and/or a ligase enzyme, and such means may optionally further comprise other reagents necessary for the ligase reaction. The means for detecting the interaction, may be any of the means discussed above in the context of the assay methods, e.g. a label provided on the nucleic acid domains of the first and second probe or it may be amplification means and means for detecting amplification products thereof e.g. reagents for a PCR reaction (e.g. amplification primers, and optionally polymerase and/or nucleotides, etc.) and for detecting PCR amplicons etc (e.g. Taqman® probes etc.).

The kit may further optionally comprise a gap/cassette oligonucleotide and/or blocking oligonucleotides for the standard proximity probes.

The kit may further optionally comprise an immobilised capture probe for the analyte, or a capture probe provided with means for immobilisation. Alternatively, the kit may comprise a solid phase for capture of, or binding to, the analyte, or one or more said first, second or third proximity probes may be immobilised or provided with means for immobilisation.

It will be evident from the description above and the representative examples described below that the methods and products of the invention have numerous advantages over existing methods. Advantageously, the use of unfolding proximity probes (preferably wherein at least one probe is unfolded by cleavage) renders the methods of the invention particularly useful for the simultaneous detection of multiple analytes in a sample, i.e. multiplex assays. Furthermore, each probe set may result in an interaction product that is tagged uniquely, which allows multiple analytes to be detected in parallel. Alternatively, for assays used to detect a large number of analytes, it may be useful to detect (e.g. visualise) the interaction products sequentially, e.g. one at a time or one group at a time. The unfolding probes used in the methods described herein also enable other reagents to be added to the assay at the same time as the probes. As the interaction domains of the probes (i.e. nucleic acid domains) cannot interact with each other, or other components in the sample, until they have been unfolded the addition of components used to detect the interaction product can be added to the assay without generating products that arise from non-specific interactions. Reducing the number of steps in the assay minimises potential errors and renders the protocol more suitable for automation. Further advantages will be evident from the description of the invention.

It is evident from the detailed description herein that various different embodiments are encompassed by the invention, and different such embodiments can give rise to different advantages. For example it is recognised that padlock probes cannot readily be amplified by RCA if the padlock probes remain linked to their target molecules, due to topological obstruction by the target molecule. However, in certain embodiments of the invention described herein cleavage of a nucleic acid domain generates a circularisable molecule, ligation of which gives rise to a circular reporter molecule which is unlinked to the target molecule, and hence which may readily be amplified by RCA, but yet allows a locally anchored amplified signal (i.e. the RCA product generated by a primer which is or results from the nucleic acid domain of a bound proximity probe).

The invention will be further described with reference to the following non-limiting Examples with reference to the following drawings in which:

FIG. 1 shows a proximity ligation assay using two proximity probes, of which one is an unfolding proximity probe, as so-called horn probe. In this representative embodiment, the analyte is a protein-DNA complex, which in the first proximity probe is bound to the protein element of the analyte (depicted as a circle) and the second proximity probe (horn probe) is bound to the DNA element of the analyte. The DNA acts as a ligation template of the analyte-binding ("first") domain of the horn probe, and the nucleic acid domain of the first proximity probe acts as a ligation template for the nucleic acid ("second") domain of the second proximity probe, wherein the ligation involves a gap oligonucleotide between the two ends of the nucleic acid ("second") domain of the horn probe.

FIG. 2 shows a proximity ligation assay using three proximity probes, of which one is an unfolding proximity probe. The nucleic acid domain of the unfolding proximity probe is unfolded by cleavage, and each end is ligated to the nucleic acid domain of a different proximity probe. Each ligation reaction is templated by ligation template ("splint") oligonucleotide. The analyte to which the proximity probes are bound is not shown.

FIG. 3 shows a proximity ligation assay using two proximity probes, of which one is an unfolding proximity probe. (A) The nucleic acid domain of the unfolded proximity probe is capable of forming a circular oligonucleotide only when in proximity to the nucleic acid domain of a second proximity probe, which acts as a ligation template. (B) The nucleic acid domain of the unfolded proximity probe forms one part of a two-part padlock probe. The second part of the padlock probe is provided as the nucleic acid domain of a second proximity probe. The two parts are capable of forming a circular oligonucleotide only when the probes are bound in proximity (to the analyte, not shown). Two "splint" oligonucleotides template the ligation reactions. The free 3' end of the nucleic acid domain of the unfolding proximity probe (depicted as an arrow) in both (A) and (B) is capable of priming an RCA reaction.

Figure 1:
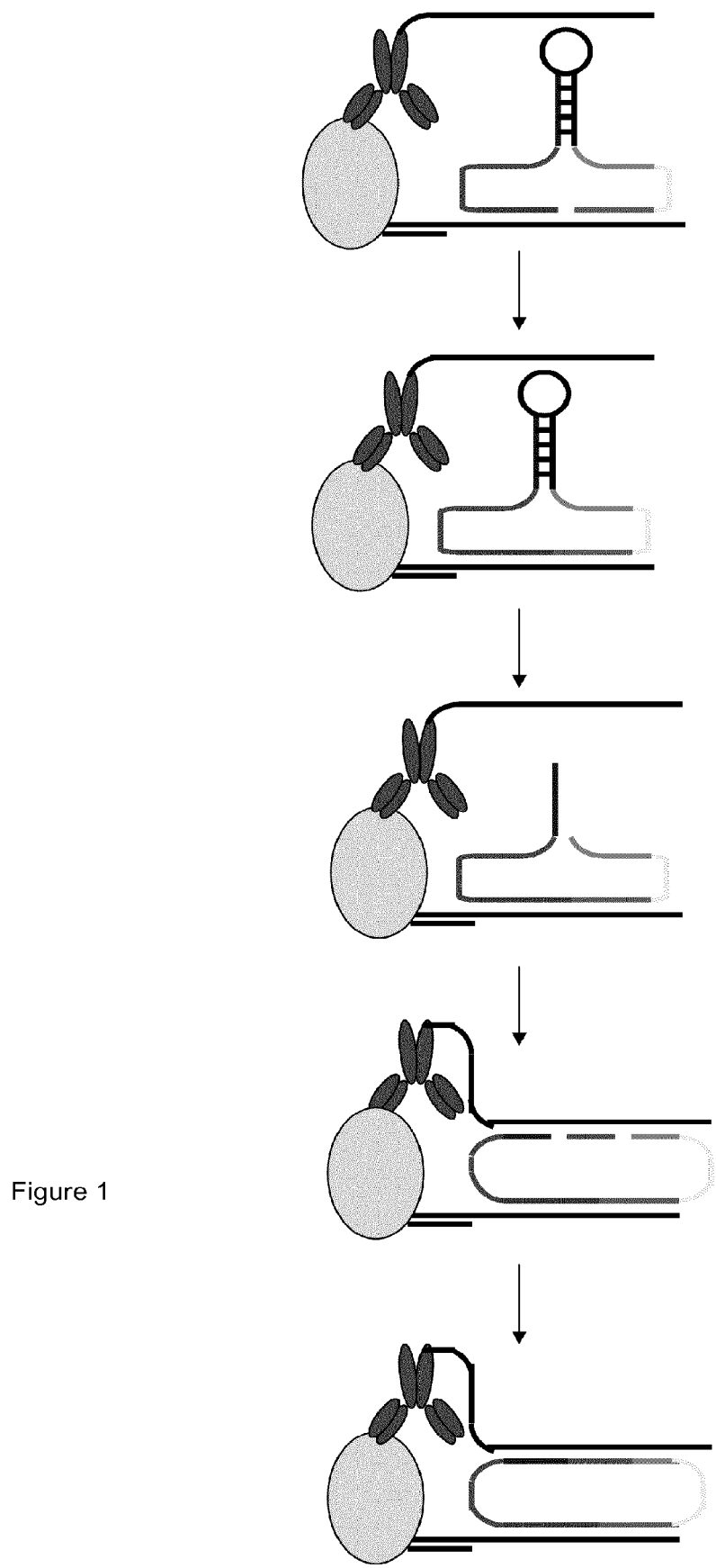
Figure 2:
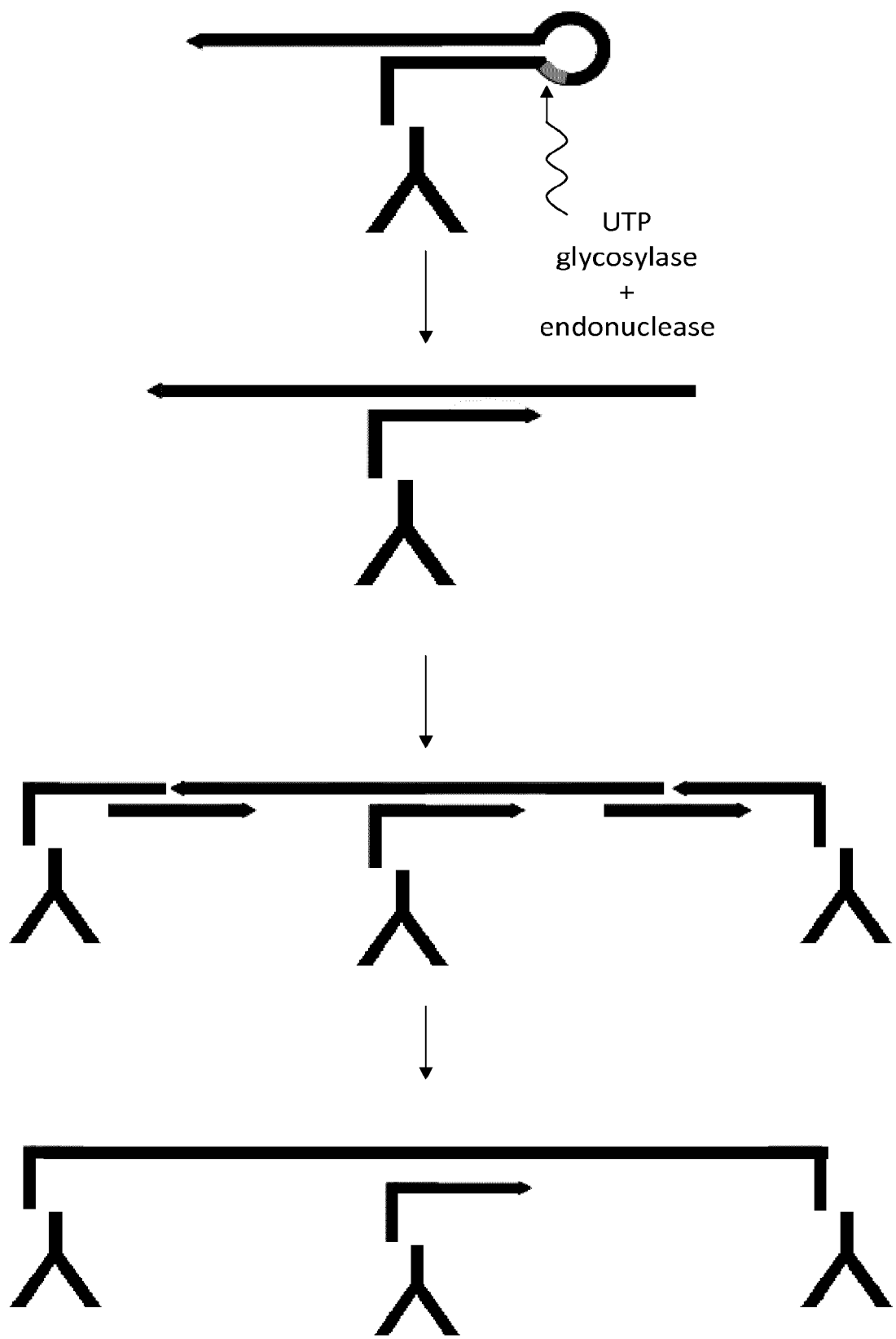
Figure 3:
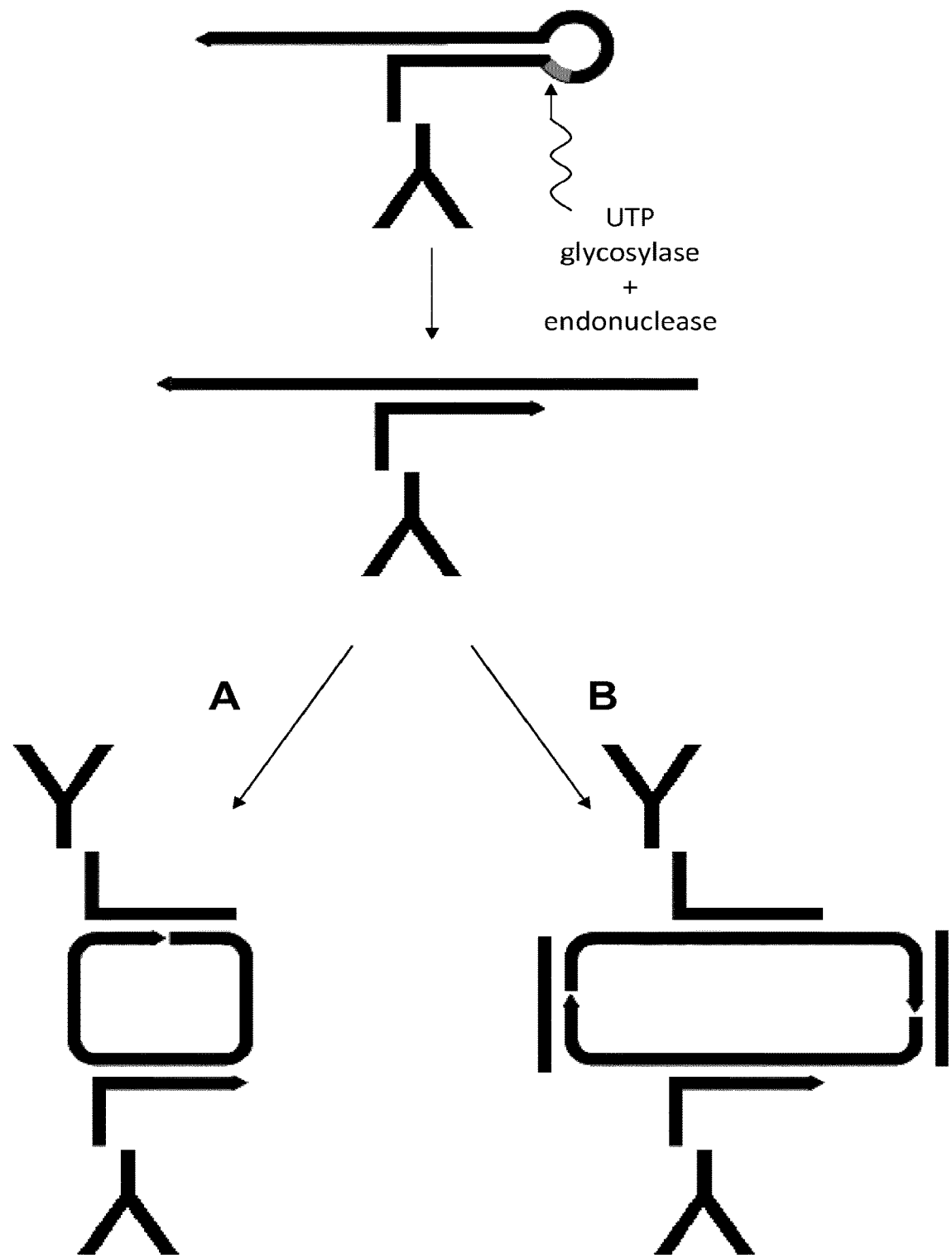
Figure 6:
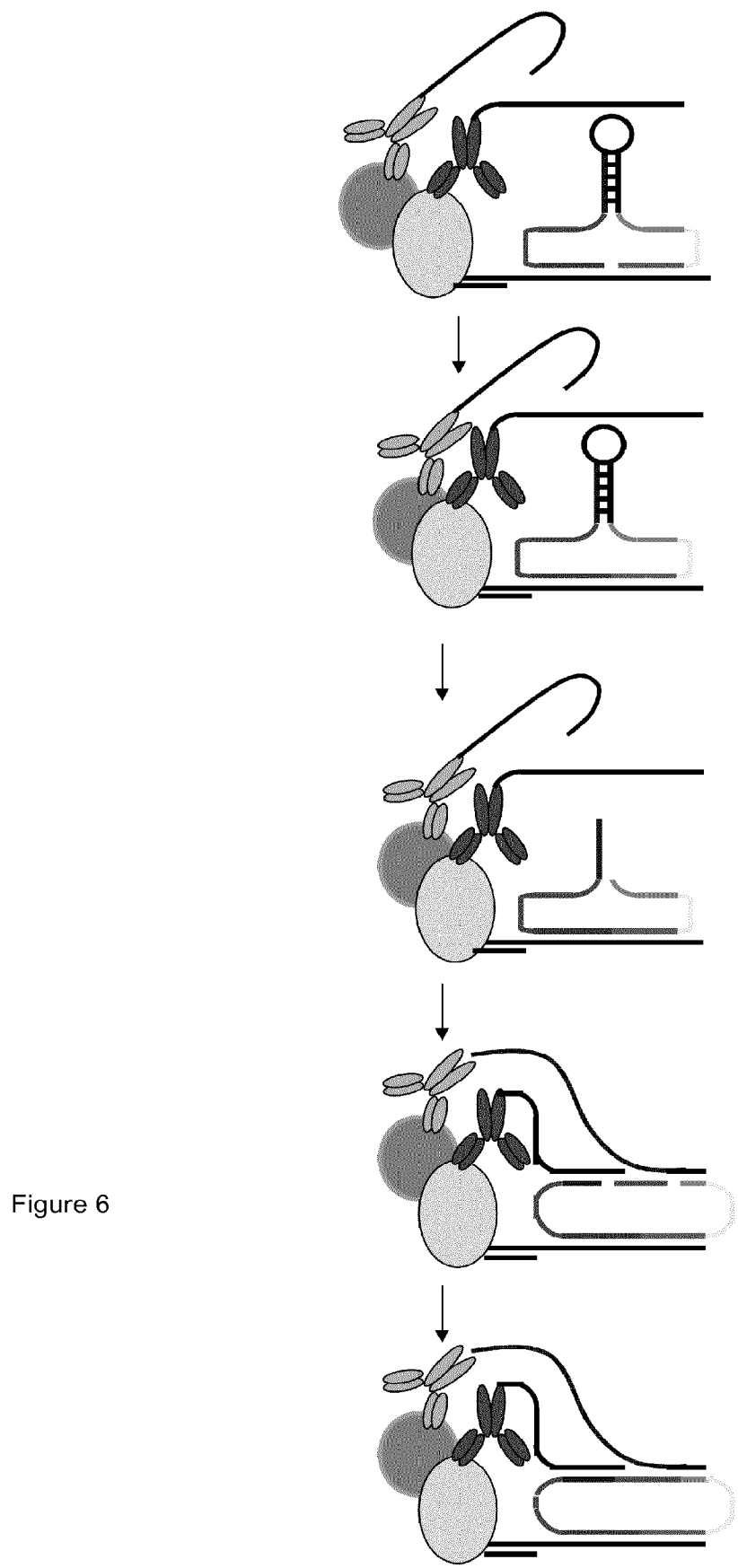

FIG. 6 shows a proximity ligation assay similar to that of FIG. 1, with the addition of a third proximity probe, bound to another protein in the protein-DNA complex (analyte), i.e. the third proximity probe may be seen as being indirectly bound to the analyte or the analyte may be seen as a complex. The two regions of the nucleic acid ("second") domain of the horn probe are ligated indirectly, i.e. via a gap oligonucleotide, utilising the nucleic acid domain of the other proximity probes as a ligation template for each ligation.

Figure 4:
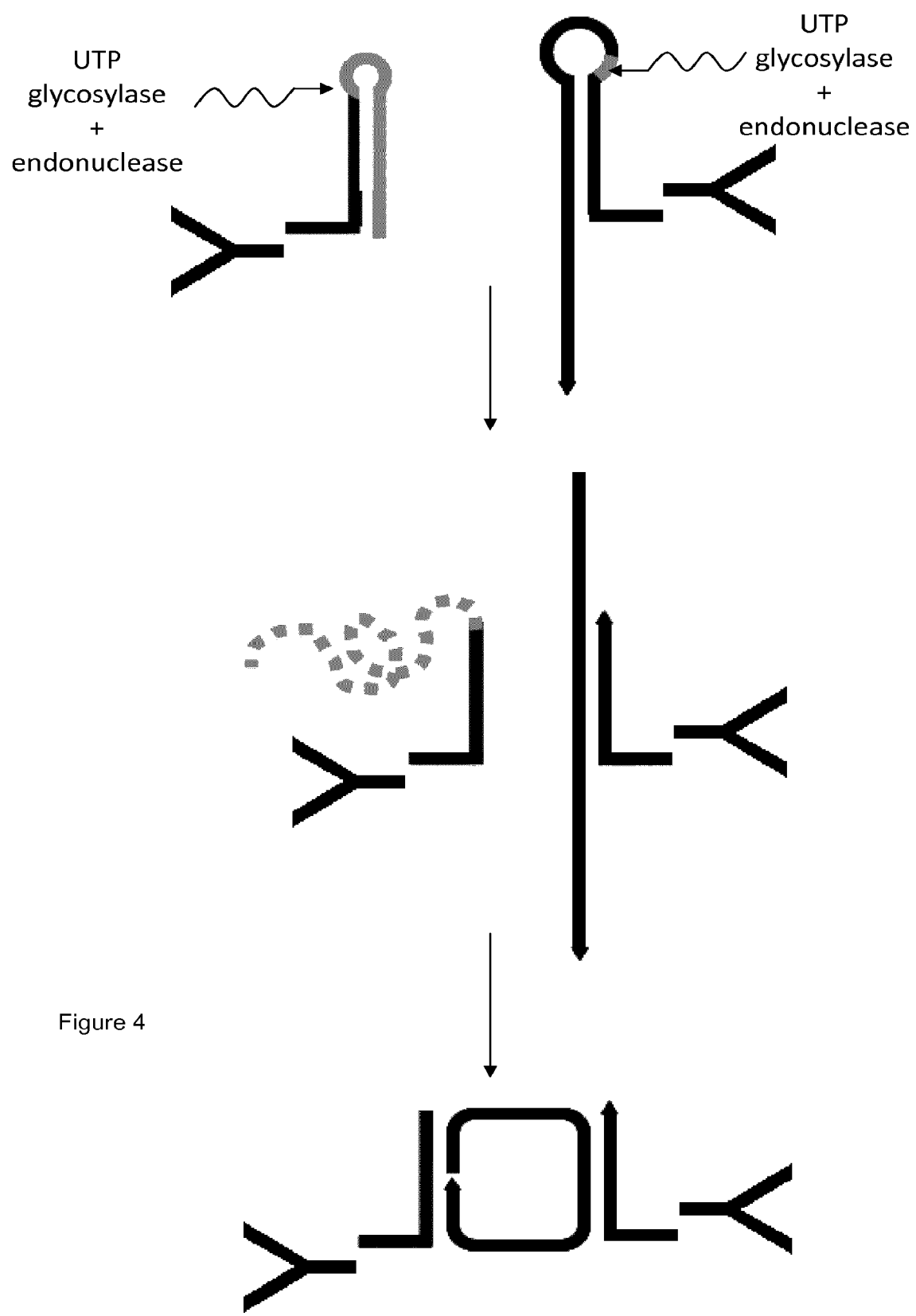
FIG. 4 shows a proximity ligation assay similar to that of FIG. 3A, where both proximity probes comprise a hairpin structure.
Figure 7:
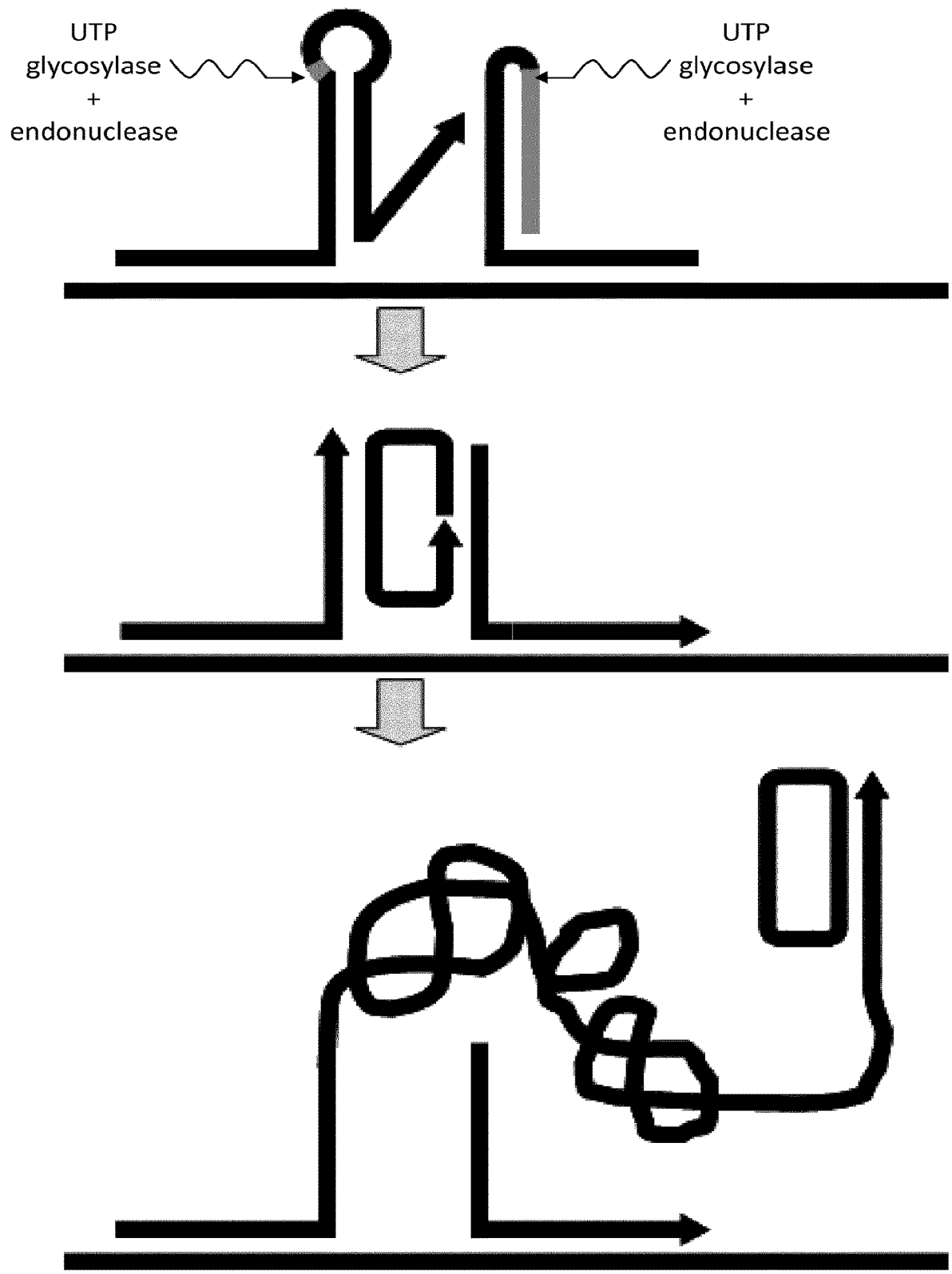

FIG. 7 shows a proximity ligation assay akin to that shown in FIG. 4, wherein the analyte-binding domains of the proximity probes and the target analyte are nucleic acid molecules. This figure demonstrates how the nucleic acid domain of a proximity probe may also act as the primer for RCA.

Figure 5:
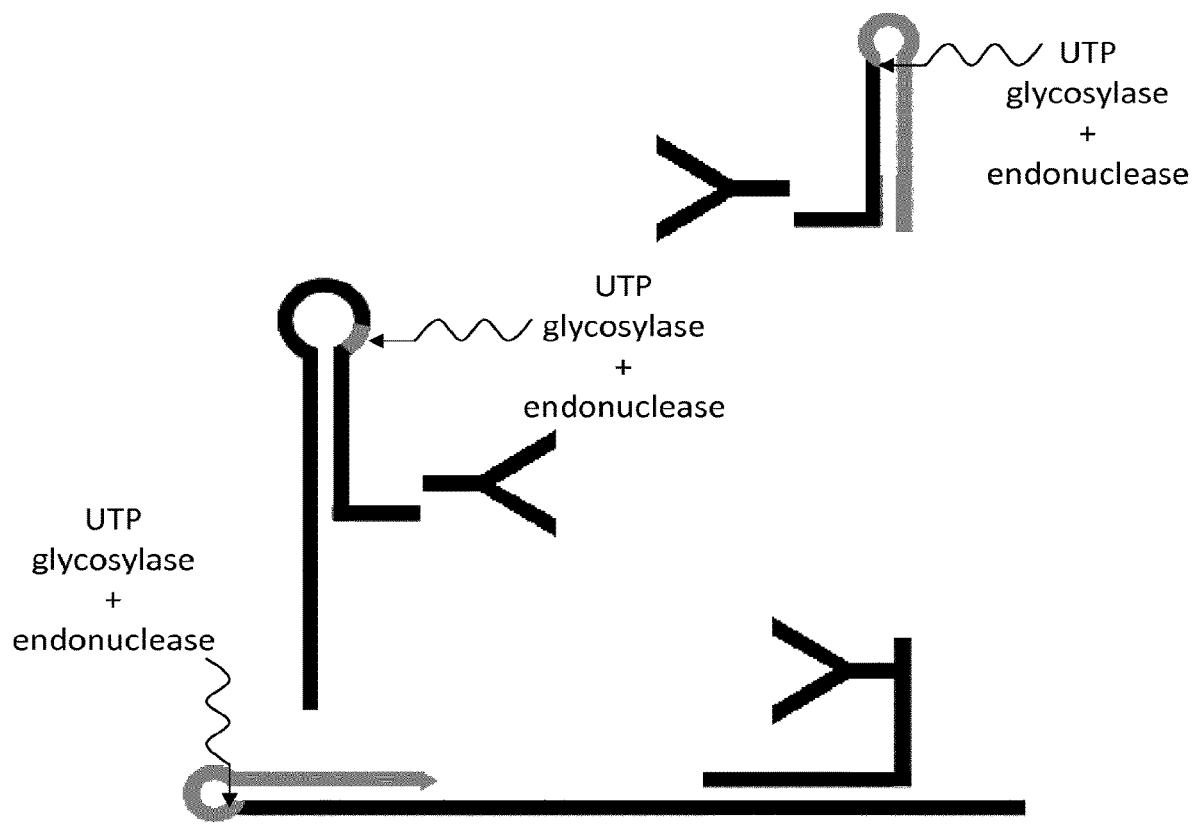
FIG. 5 shows a proximity ligation assay similar to that of FIG. 4, with the addition of a third proximity probe with a hairpin protected nucleic acid domain, which is capable of priming a RCA reaction of the circularised oligonucleotide of the unfolding proximity probe.
Figure 5:
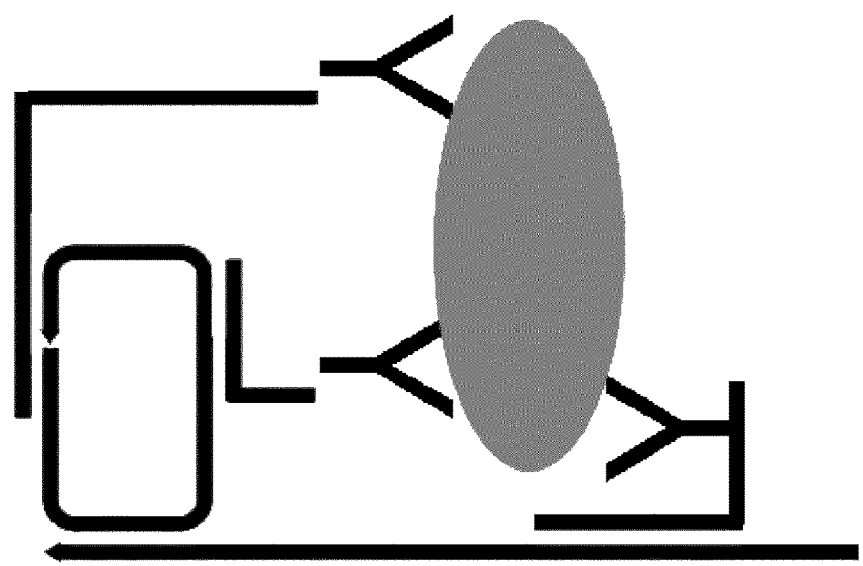
Figure 8:
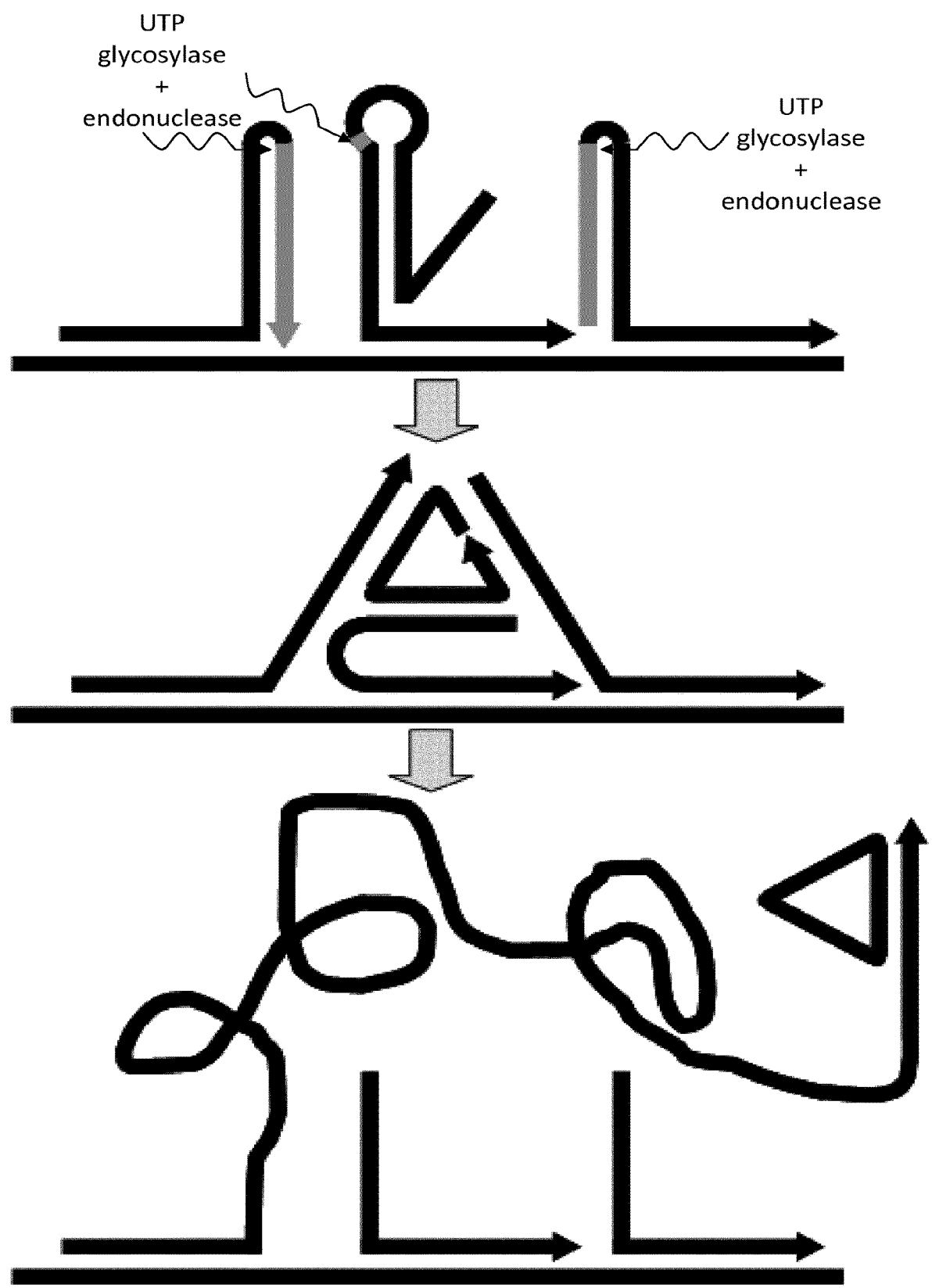

FIG. 8 shows a proximity ligation assay akin to that shown in FIG. 5, wherein the analyte-binding domains of the proximity probes and the target analyte are nucleic acid molecules.

Figure 9:
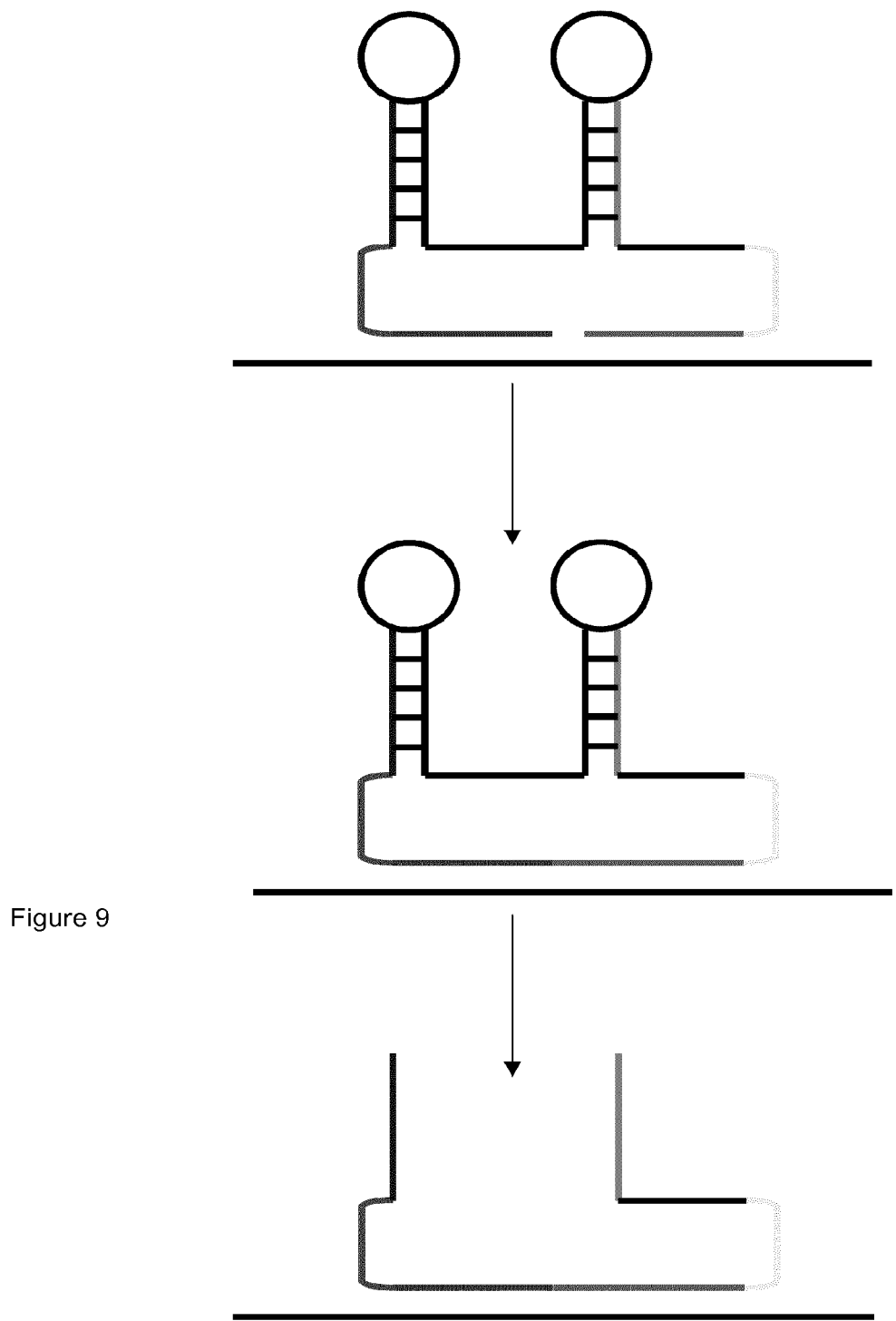

FIG. 9 shows a horn probe with two hairpin structures.

Figure 10:
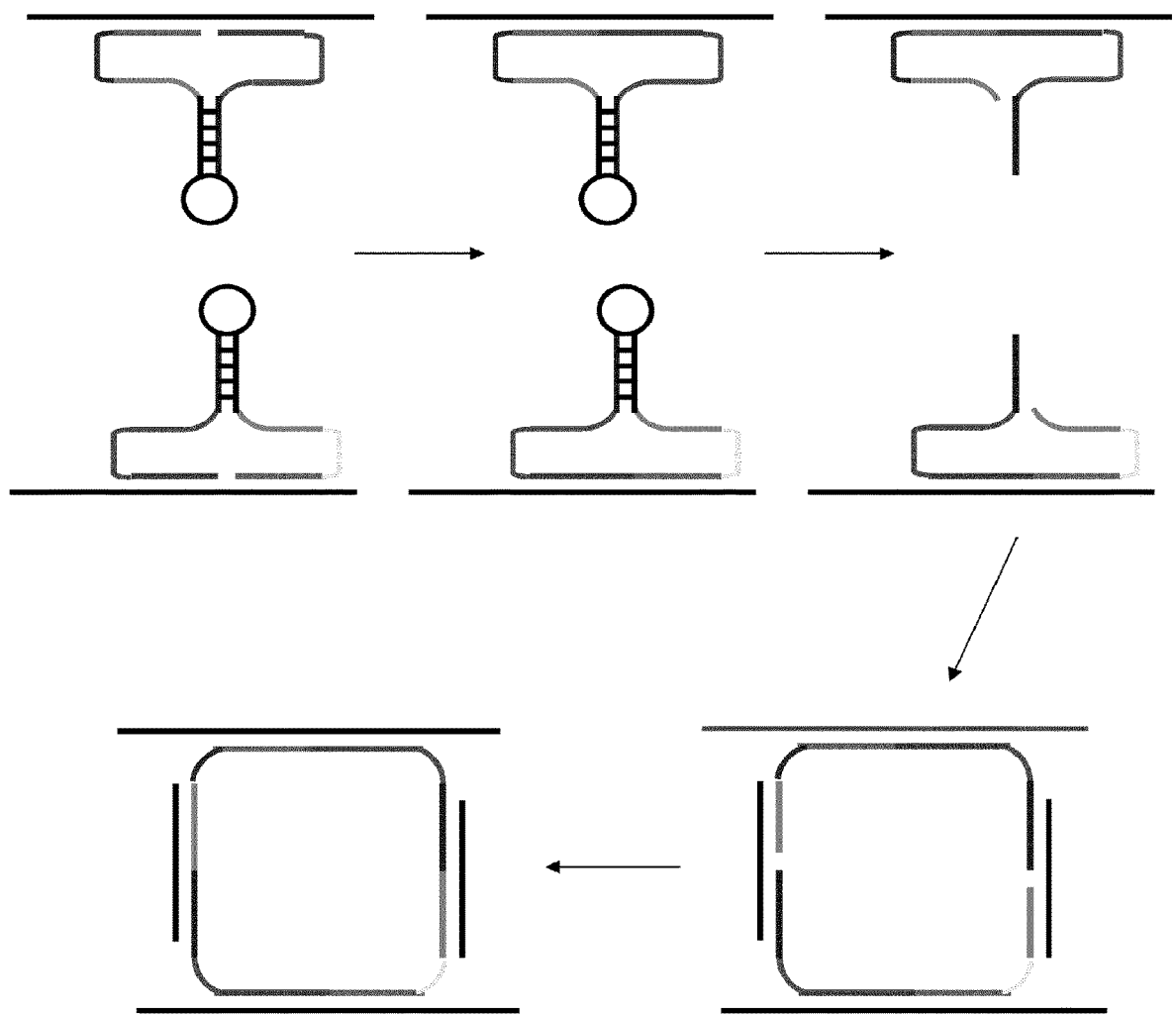

FIG. 10 shows how two horn probes can interact to form a circular oligonucleotide, via two ligation template oligonucleotides. The analyte could be viewed as a single nucleic acid molecule comprising two target sequences for the first domain of each horn probe, wherein the intervening sequence of the analyze nucleic acid is not shown. Alternatively, the horn probes may be viewed as binding to the nucleic acid domains of proximity probes bound to the analyte (not shown), i.e. as binding to the analyte indirectly.

Figure 11:
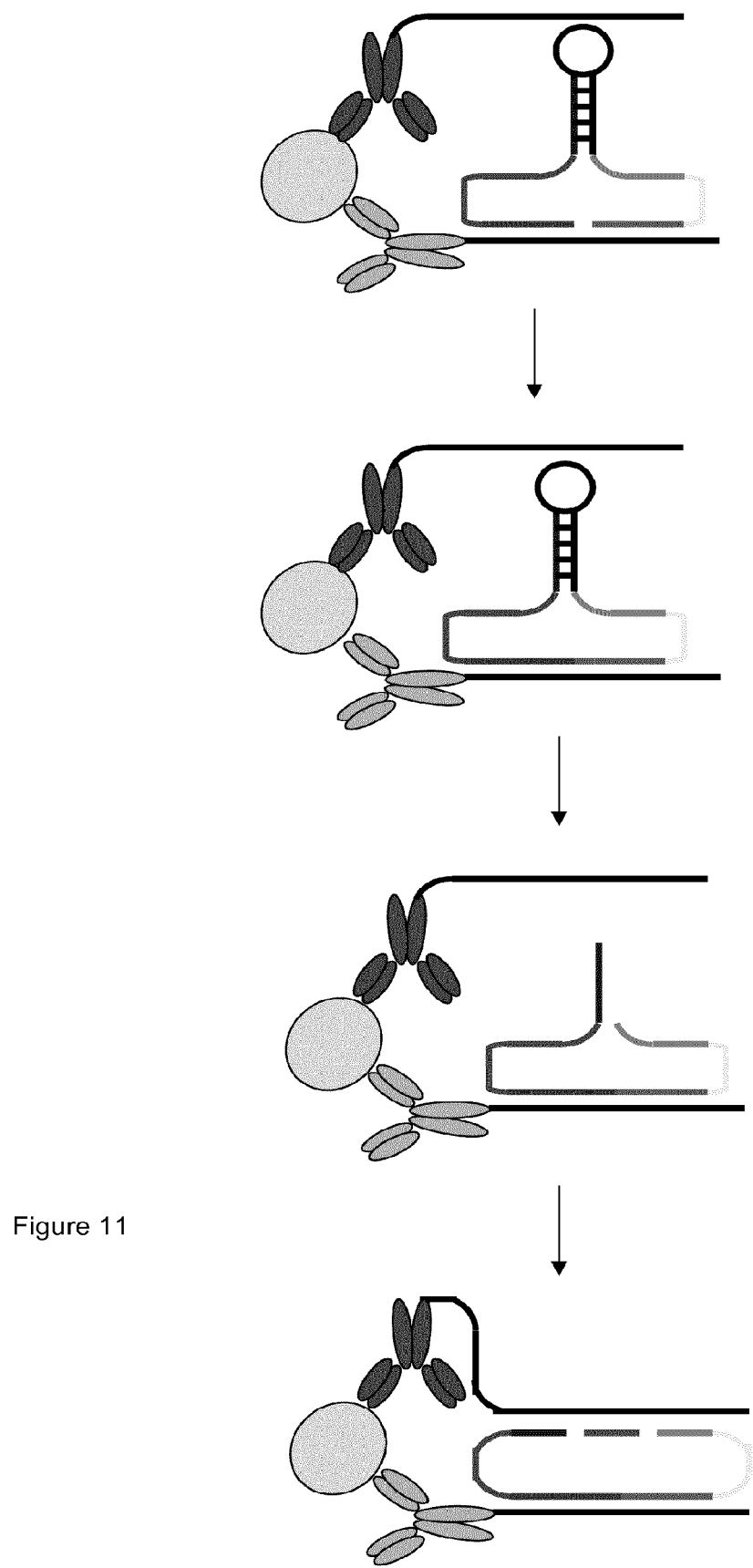

FIG. 11 shows a proximity ligation assay akin to that of FIG. 1, wherein the DNA of the protein-DNA complex is replaced by a proximity probe. Hence, the horn probe can be viewed as binding to the analyte indirectly.

Figure 12:
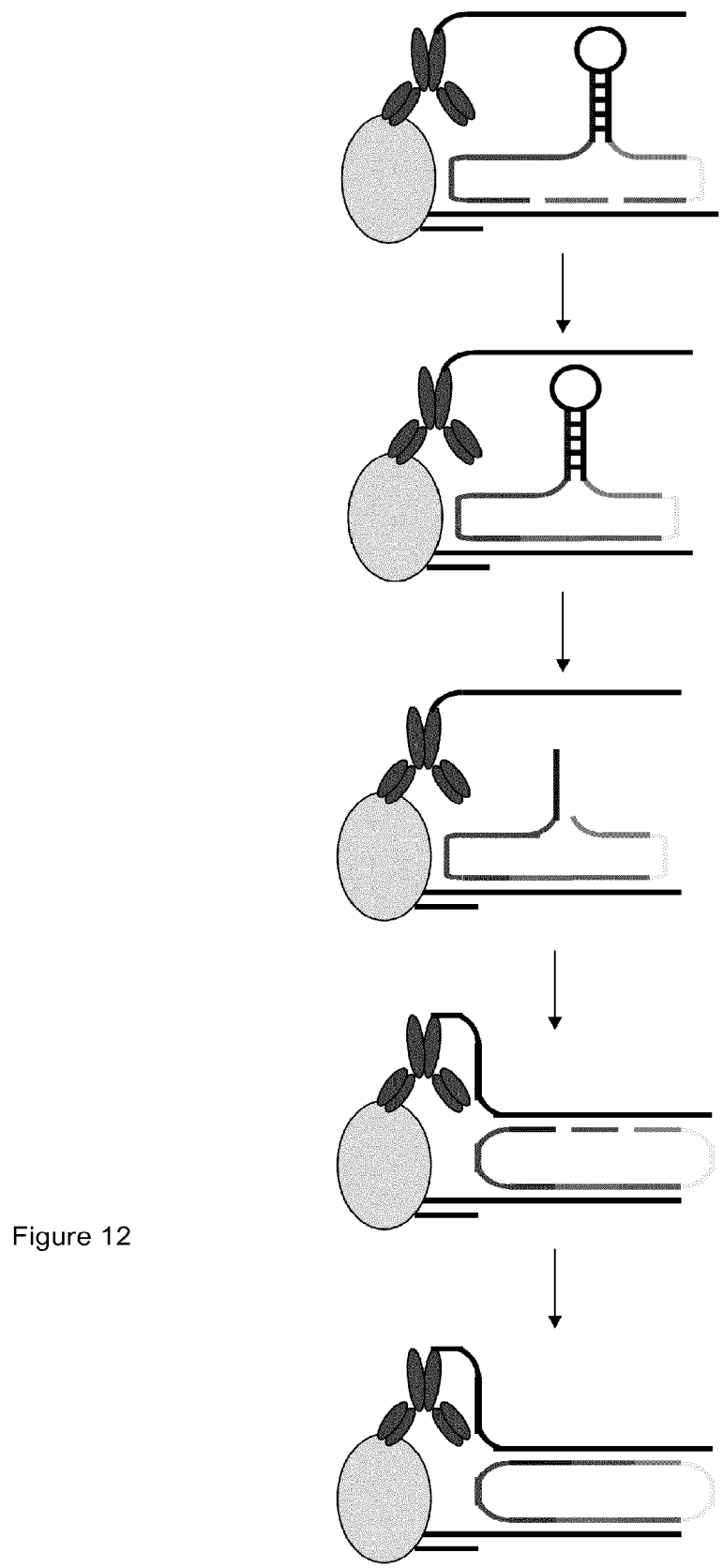

FIG. 12 shows a proximity ligation assay akin to that of FIG. 1, wherein both the first and second ligations of the horn probe involve a gap oligonucleotide.

Figure 13:
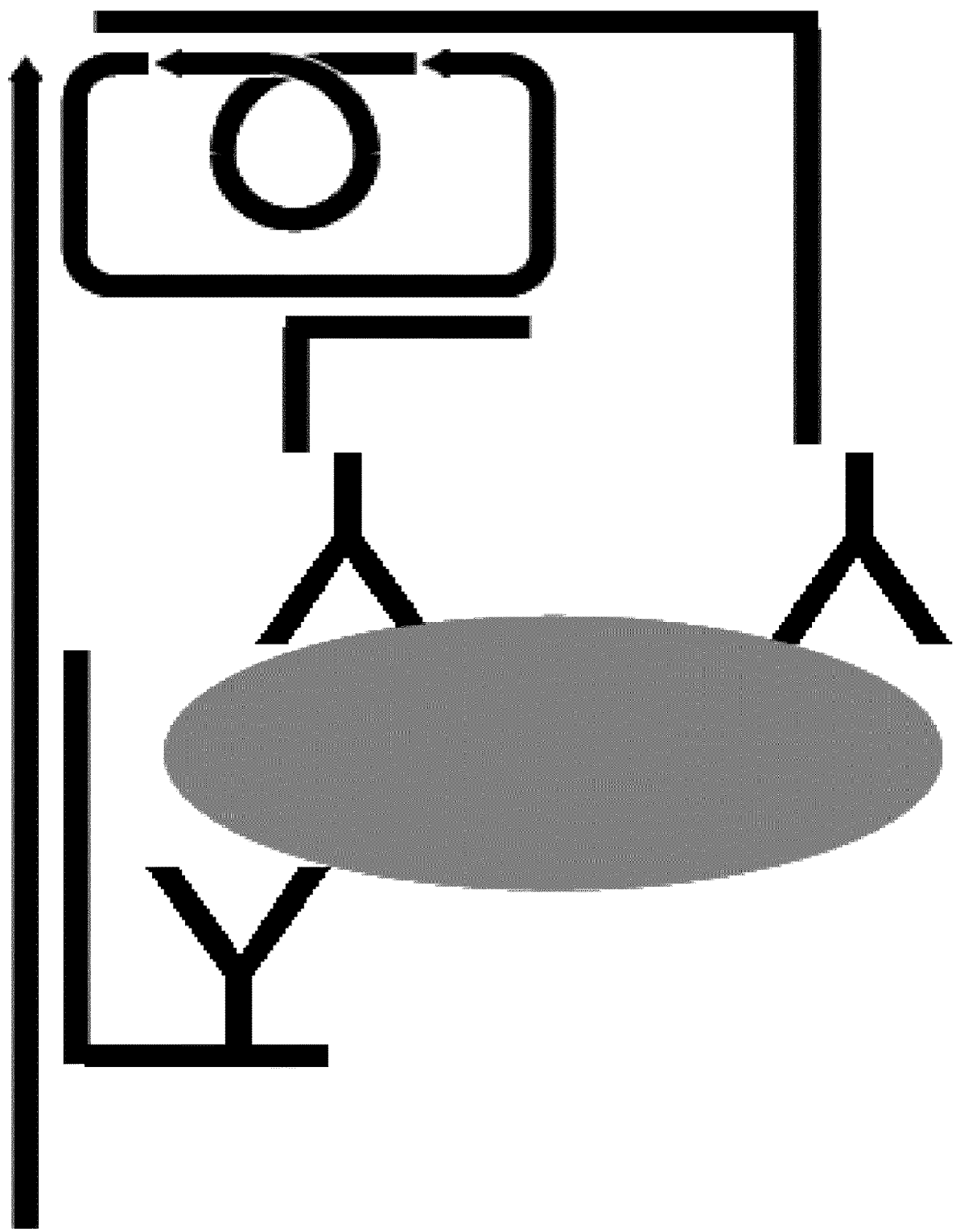

FIG. 13 shows a proximity ligation assay akin to that of FIG. 5, where in the ligation of the circular oligonucleotide involves a gap oligonucleotide. In this representative example, the gap oligonucleotide comprises two regions of complementarity to the ligation template nucleic acid domain, such that it forms are "bulge" or "loop". The additional "loop" sequence may act as a marker sequence to be incorporated into the circular oligonucleotide for detection.

Figure 14:
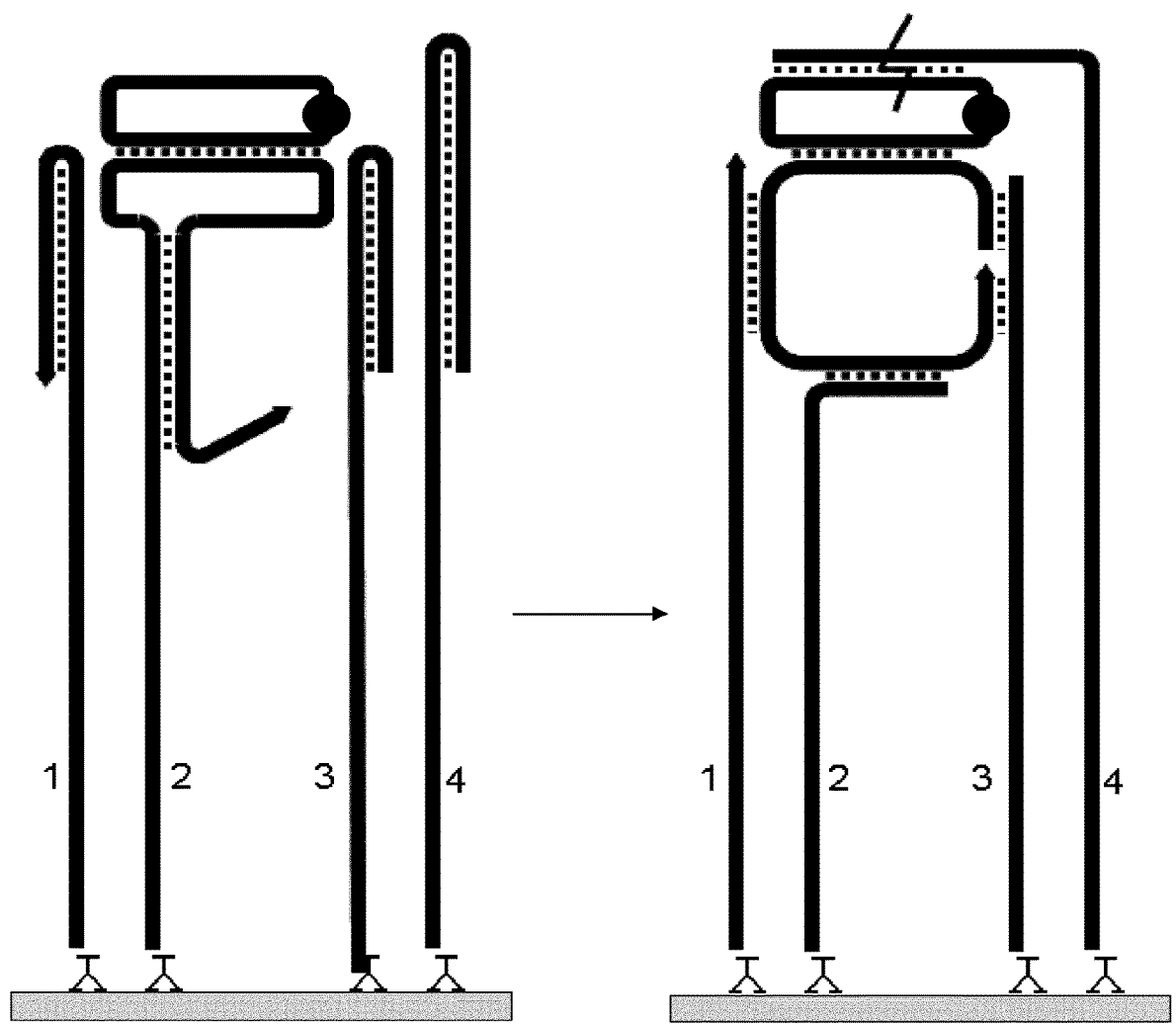

FIG. 14 shows a proximity ligation assay comprising four proximity probes, wherein the reactive element of the nucleic acid domain of each probe is protected by a hairpin structure. The preformed circle oligonucleotide, which is hybridised to the nucleic acid domain of the second proximity probe contains an exonuclease block (depicted as a black circle on the preformed circle oligonucleotide), so that it cannot be used as a primer for rolling-circle amplification after it is cleaved.

Figure 15:
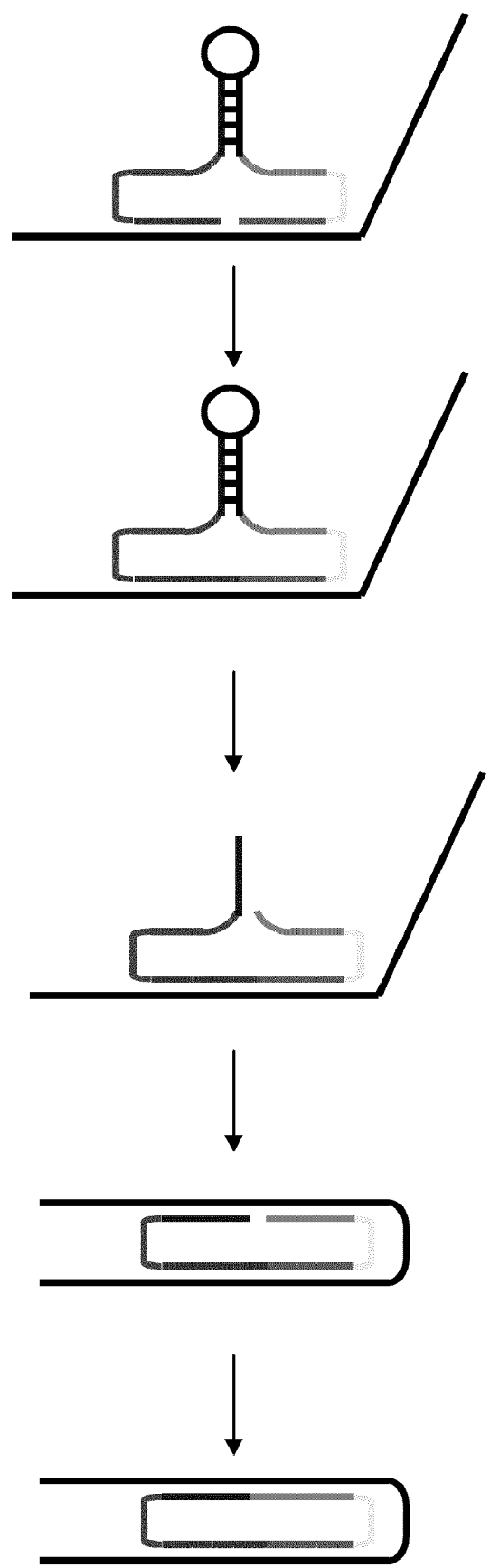

FIG. 15 shows how a single horn probe may be used to detect a nucleic acid molecule in a sample.

FIG. 16 shows how the nucleic acid domain of a proximity probe may comprise both parts of a two part padlock probe. The first proximity probe is an unfolding proximity probe, which when unfolded, e.g. by cleavage, provides a ligation template for the two parts of the padlock probe. The other ligation template is provided as the nucleic acid domain of the second proximity probe.

Figure 17:
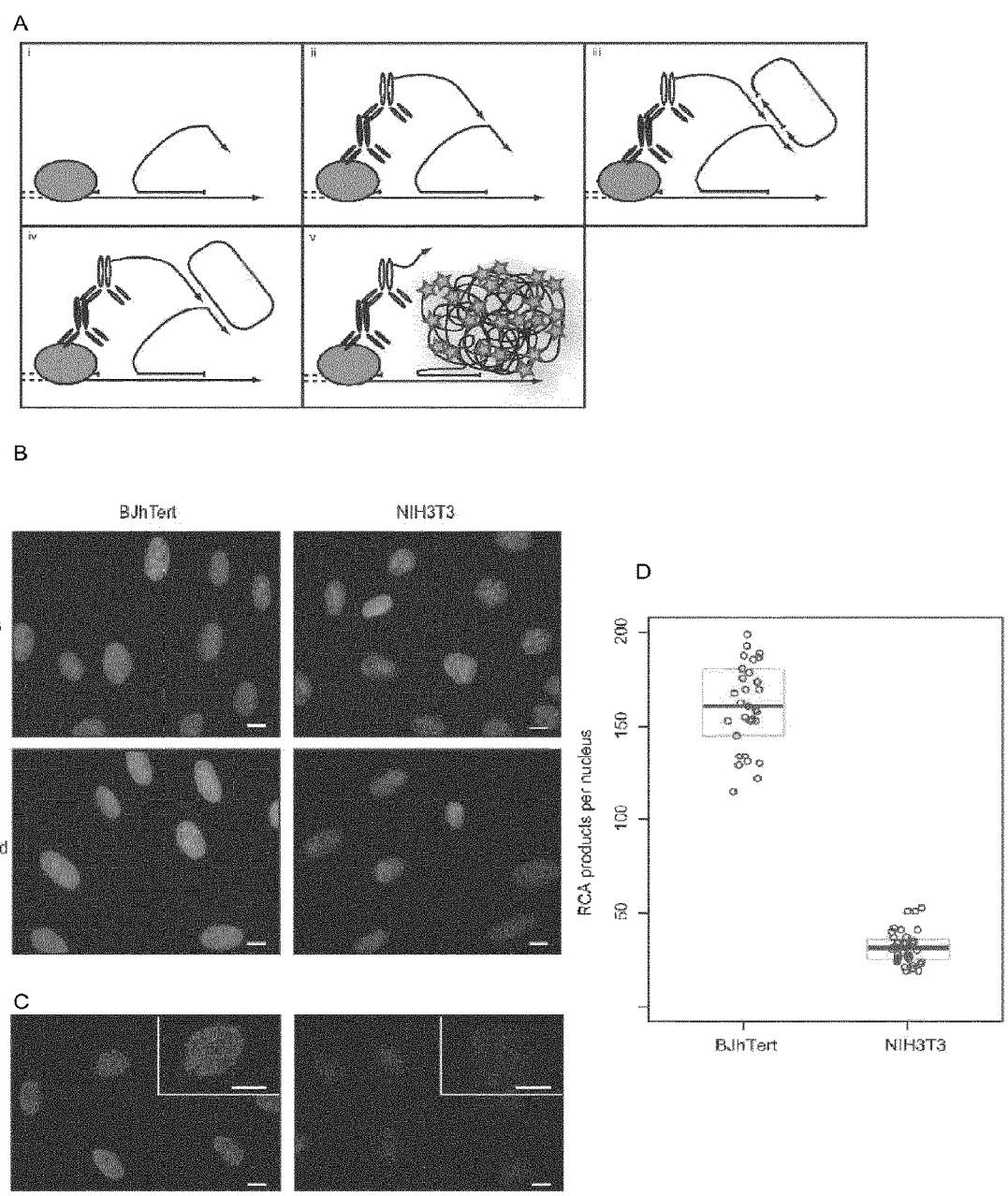

FIG. 17 shows a Hybridization based in situ proximity ligation assay (PLA), wherein: Ai shows the DNA-binding PLA-probe is hybridized to single stranded genomic DNA: Aii shows Histone H3 is detected by a primary antibody and a secondary PLA-probe; Aiii shows two circularization oligonucleotides, a padlock probe and a gap oligonucleotide (the padlock probe containing a hybridization site for fluorescence detection), which are hybridized to the nucleic acid domains of both PLA-probes; Aiv shows the subsequent ligation forming a circular DNA molecule; and Av shows the circular DNA molecule is now amplified by RCA and detected through hybridization with fluorescently labelled oligonucleotides. Bi shows the immunofluorescence detection of histone H3 in human (BJhTert) and mouse (NIH3T3) fibroblasts (scale bars represent 10 μm). Bii shows RCA-mediated detection of hybridized DNA-binding PLA-probe in human and mouse cells (scale bars represent 10 μm). C shows the detection of individual histone H3 proteins in proximity to an Alu-repeat (RCA products seen as spots). D shows the quantification of histone H3—Alu-repeat interactions in human and mouse cells and results from automated quantification of RCA products in 33 (human) and 36 (mouse) cells from one experiment out of three replicates are shown. Each dot represents the number of detected interactions in an individual cell. Median (line in the boxes), 25th and 75th percentile (boxes) are shown.

Figure 18:
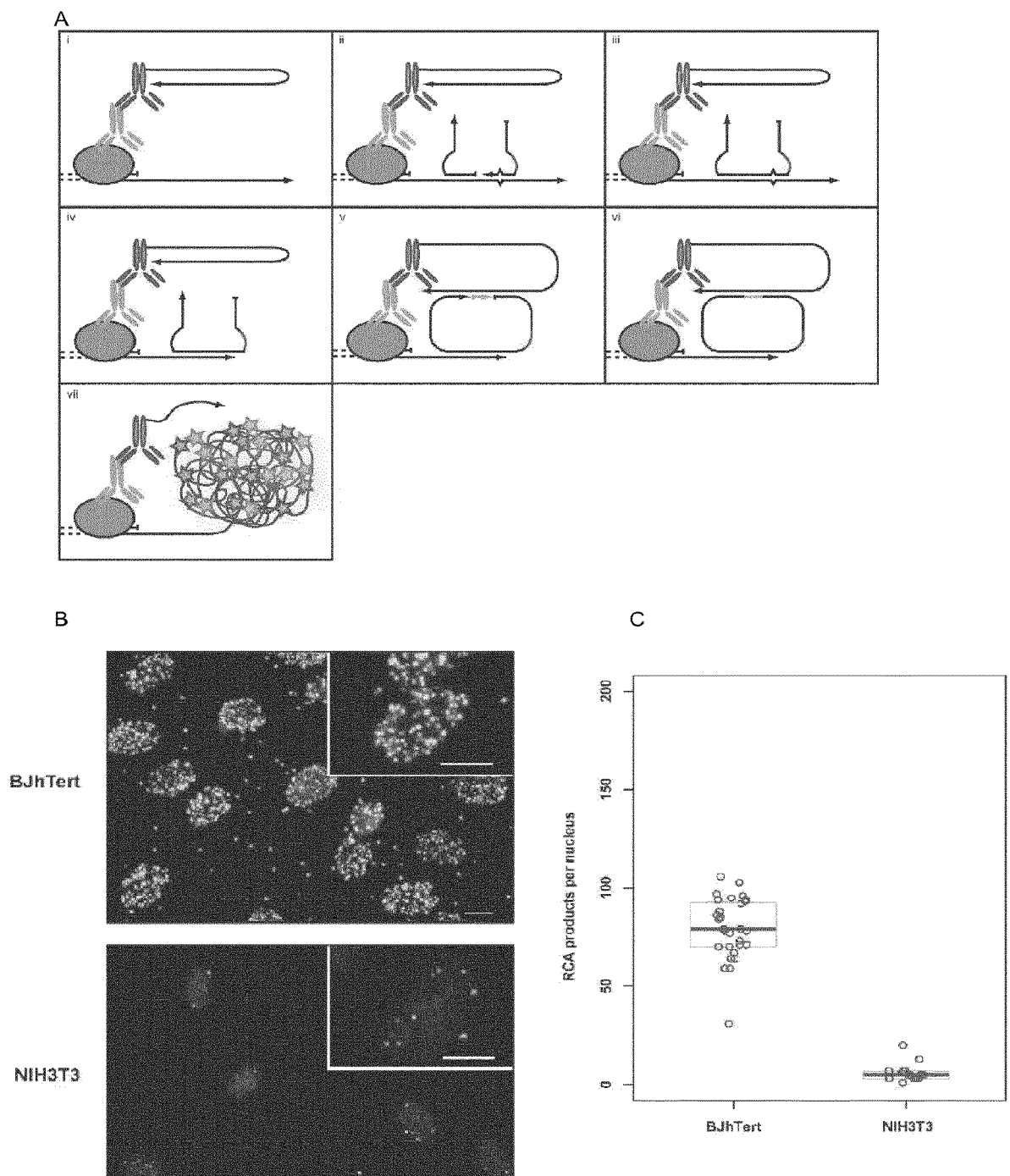

FIG. 18 shows a Genomic DNA-templated in situ PLA, wherein: Ai shows a primary antibody and a secondary PLA-probe bound to Histone H3; Aii shows a two part padlock probe (where one-part contains a hybridization site for fluorescence detection) hybridized to genomic DNA forming a single G/A mismatch with the genomic DNA; Aiii shows the first ligation of the two-part padlock probe; Aiv shows the creation of a free 3'end of genomic DNA utilizing MutY/EndoIV enzymes which cleave the G/A mismatch formed by the two-part padlock probe; Av shows hybridisation of the nucleic acid domain of the protein bound proximity probe to the unligated regions of the two-part padlock probe, incorporating an additional gap oligonucleotide (shown as an arrow); Avi shows the second ligation of the two-part padlock probe to incorporate the gap oligonucleotide to form a circular DNA molecule; and Avii shows the amplification of the circular DNA molecule by RCA and detection through hybridization of fluorescently labelled oligonucleotides to the two detection sites (the first from one part of the two-part padlock probe, and the second from the gap oligonucleotide) resulting in double coloured signals. B shows the detection of individual histone H3 proteins in proximity to an Alu-repeat (RCA products seen as spots) in human (top) and mouse (bottom) fibroblasts (scale bars represent 10 μm). C shows the quantification of histone H3—Alu-repeat interactions in human and mouse cells. Results from automated quantification of RCA products in 15 (mouse)—29 (human) cells from one experiment out of three replicates are shown. Each dot represents the number of detected interactions in an individual cell. Median (line in the boxes), 25th and 75th percentile (boxes) are shown.

Figure 19:
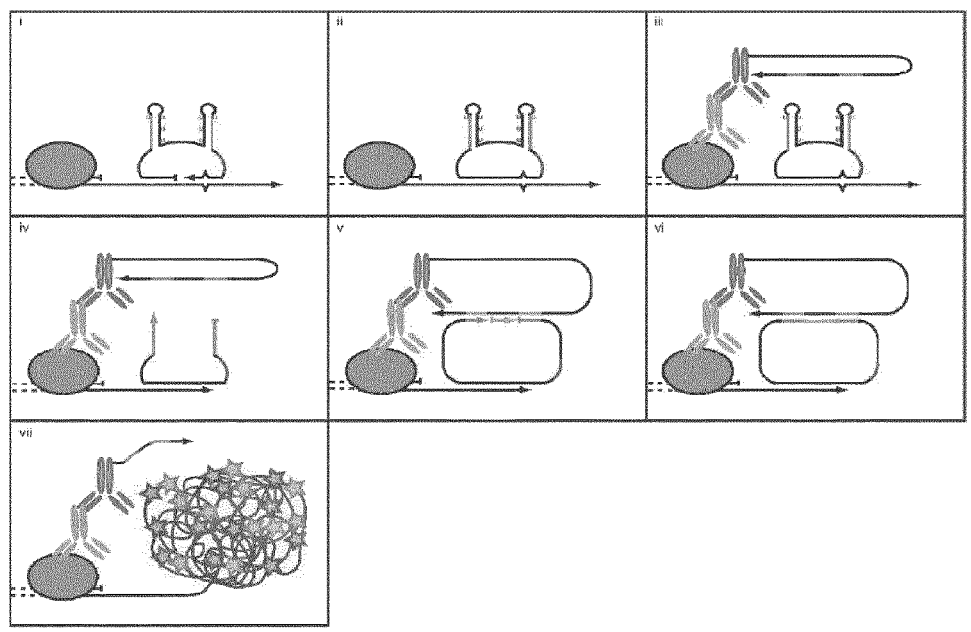
Figure 19:
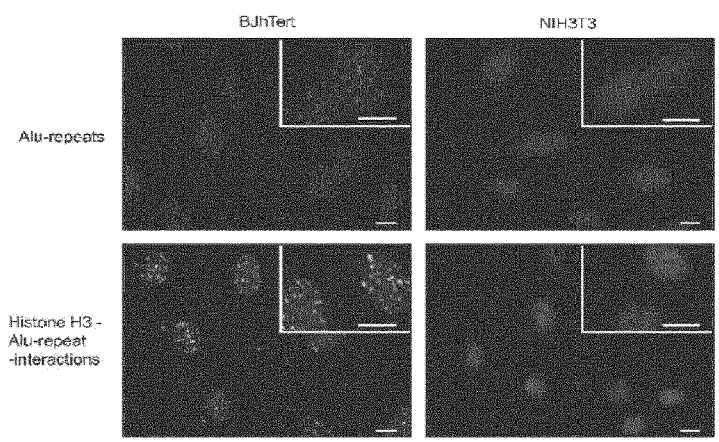
Figure 19:
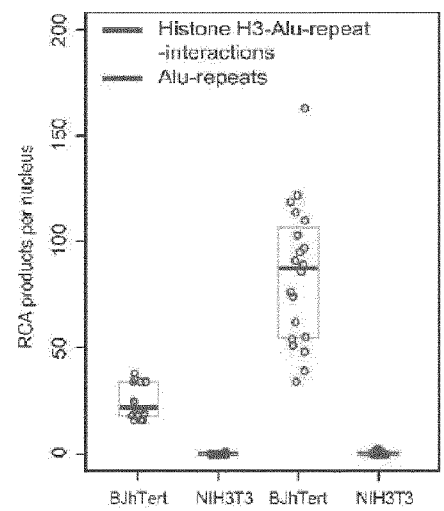

FIG. 19 shows a horn probe based in situ PLA, wherein: Ai—Alu repeats are detected by hybridization of the horn probe (hairpin containing padlock probe, also containing a hybridization site for fluorescence detection); Aii shows the first ligation of the horn probe, ligated by Ampligase; Aiii shows a primary antibody and the secondary PLA-probe bound to Histone H3; Aiv shows how the hairpin structure of the horn probe is opened by UNG/EndoIV treatment to free the complementary ends. In the same step MutY/EndoIV enzymes are utilized to create a free 3'end of genomic DNA by cleaving the G/A mismatch formed by the horn probe; Av shows hybridisation of the nucleic acid domain of the protein bound proximity probe to the unligated complementary ends of the horn probe, incorporating an additional gap oligonucleotide (shown as an arrow); Avi shows the second ligation of the horn probe to incorporate the gap oligonucleotide to form a circular DNA molecule; and Avii shows the amplification of the circular DNA molecule by RCA and detection through hybridization of fluorescently labelled oligonucleotides to the two detection sites (the first from one part of the horn probe, and the second from the gap oligonucleotide) resulting in double coloured signals. Bi shows the amplification of the horn probe in Aii alone results in detection of individual Alu-repeats (RCA products seen as spots) in human and mouse fibroblasts. Bii shows the detection of individual histone H3 proteins in proximity to an Alu-repeat (hybridization with both red and green fluorescence labelled oligonucleotides results in RCA products seen as yellow spots) in human and mouse fibroblasts (scale bars represent 10 μm). C shows the quantification of histone H3—Alu-repeat interactions (left half of graph) and Alu-repeats alone (right half of graph) in human and mouse cells. Results are from automated quantification of RCA products in 15 (human, PDI), 21 (mouse, PDI), 20 (human, Alu-repeat only) and 16 (mouse, Alu-repeat only) cells from one experiment out of three replicates are shown. Each dot represents detected interactions in an individual cell. Median (lines in boxes). 25% and 75% quartile (boxes) are shown.

Figure 20:
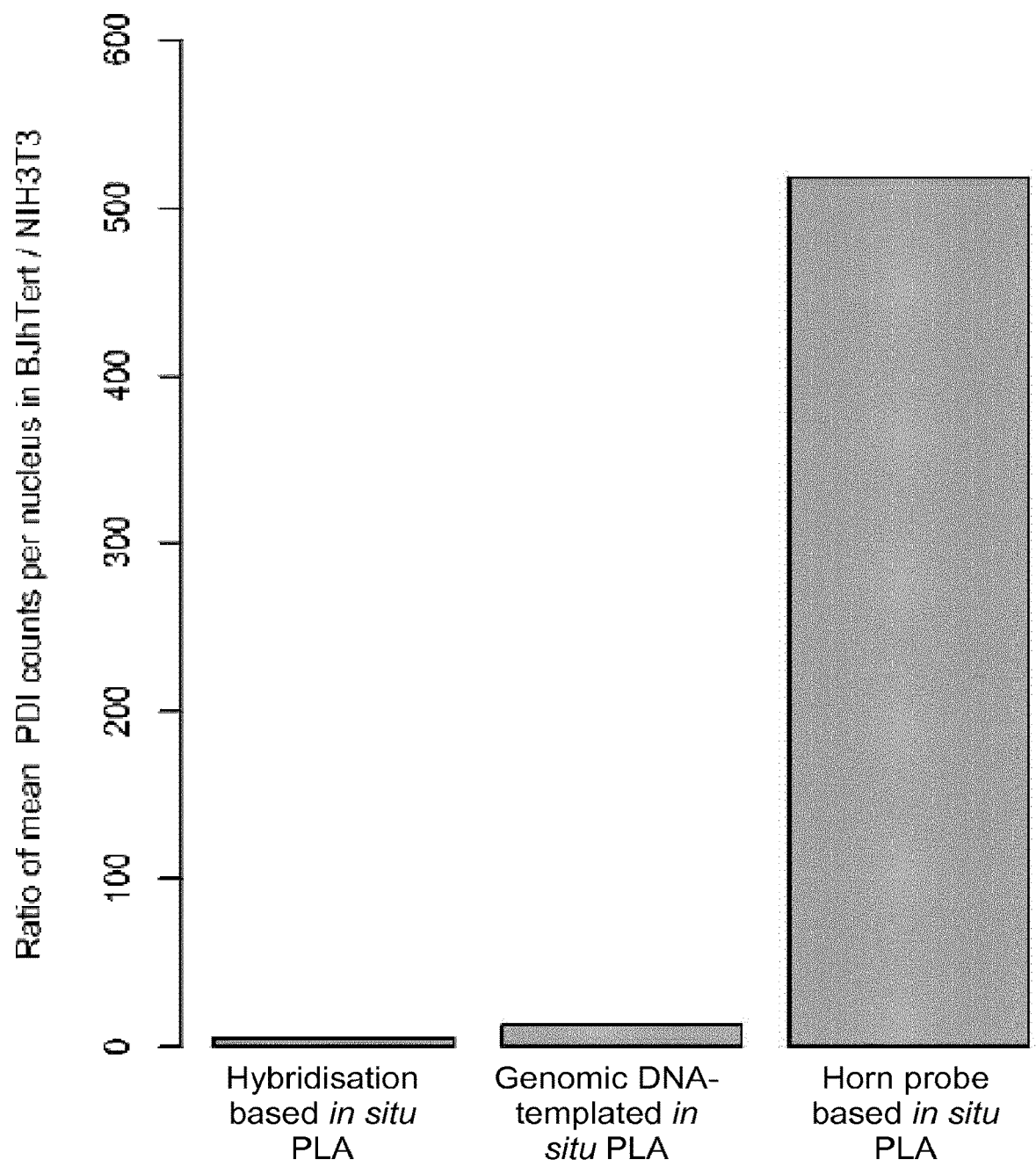

FIG. 20 shows the ratio of mean PDI counts per nucleus in BJhTert/NIH3T3 cells from the experiments shown in FIGS. 17-19.

Figure 21:
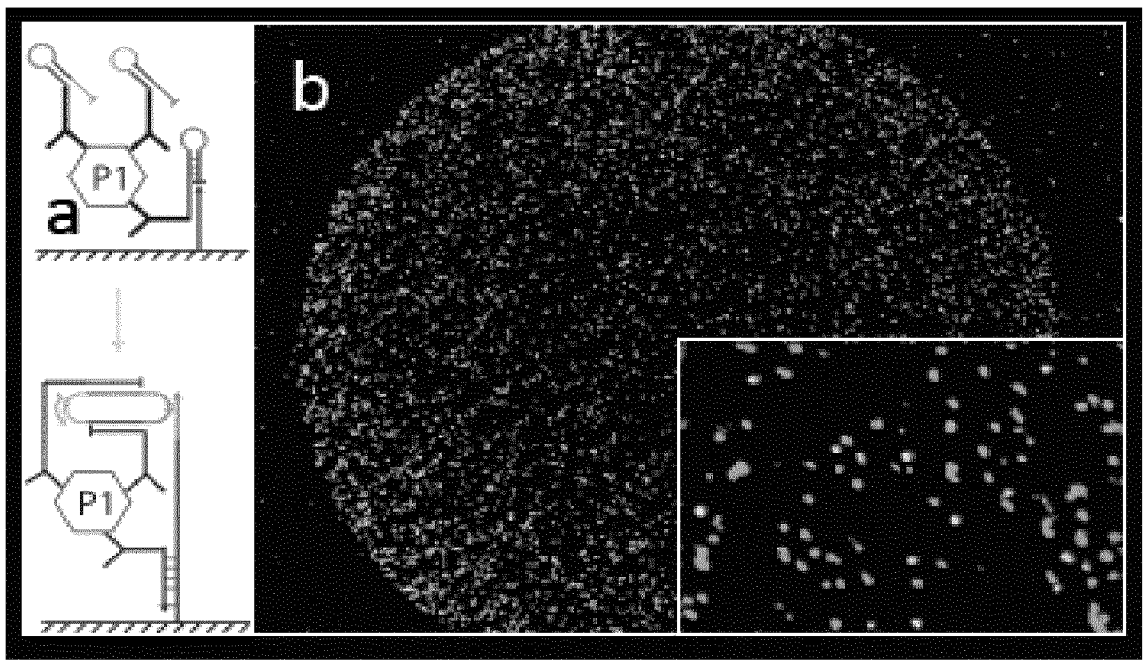

FIG. 21 shows an in situ blob sequencing readout of on chip PLA with dual ligation system, wherein: a) shows an illustration of on chip PLA with dual ligation system in which a set of three antibodies conjugated with hairpin structure oligonucleotides serve as proximity probes, i.e. unfolding proximity probes. One probes was immobilized on a glass slide by ligation to the short oligonucleotide affixed on the slide, and the other two proximity probes carry barcode sequences. Upon binding of the proximity probes to the same target molecule and unfolding of the nucleic acid domains of said probes, a circular DNA is formed with an addition of an extra ligation template; and b) shows a photograph of a chip on which VEGF and Mouse IgG were applied as target proteins and spiked in buffer with a ratio of 1:1. Specific protein barcode for each protein was included in the proximity probes. After on chip proximity ligation and RCA, the amplified products were visualized by calling the first base using Illumina sequencing reagents. Base 'T' encoding for Mouse IgG appears in both red and green channels, and base 'G' encoding for VEGF appears in only green channel.

Figure 22:
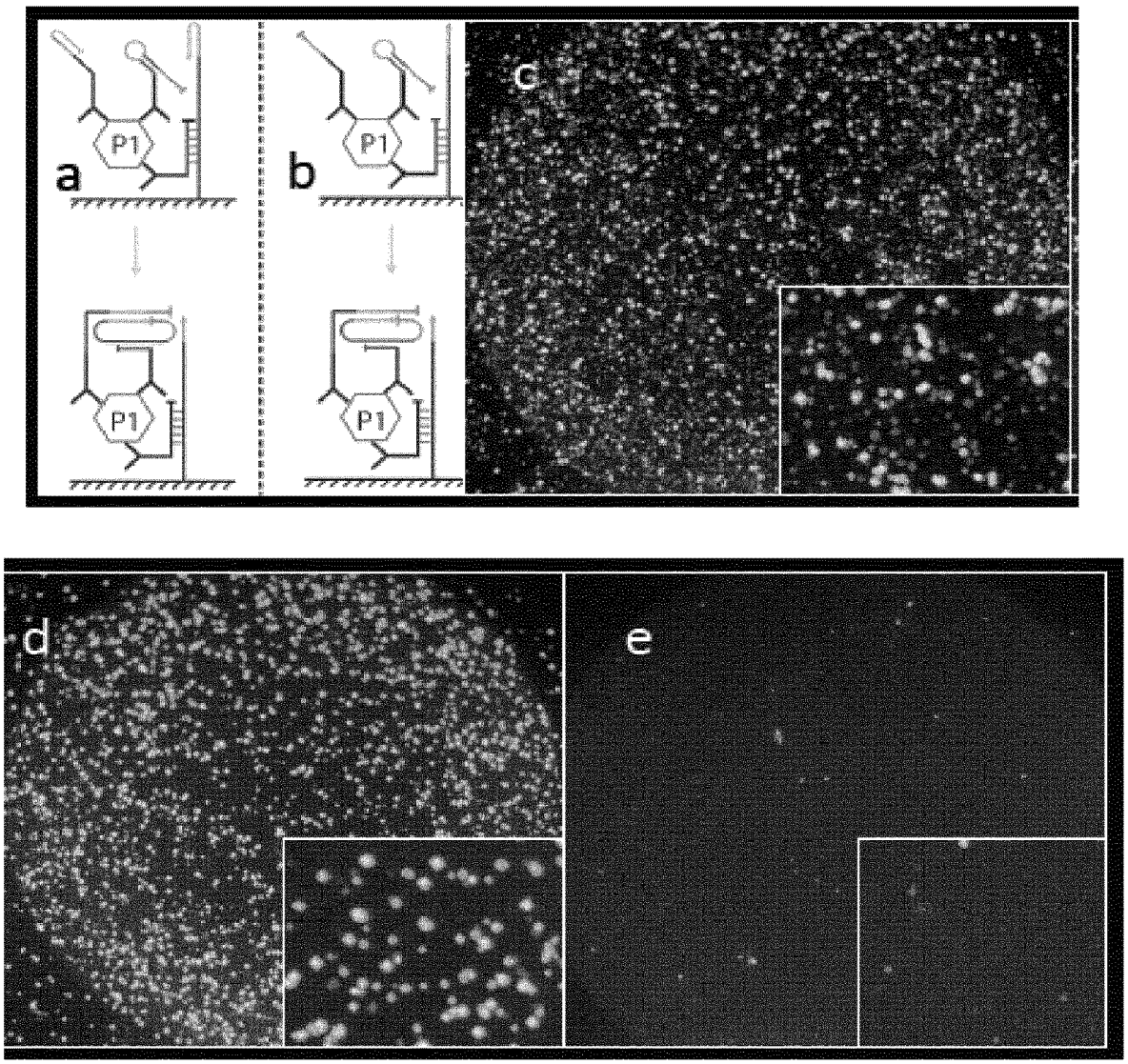

FIG. 22 shows an in situ blob sequencing readout of on chip PLA with a mono ligation system, wherein: a) shows an illustration of on chip PLA with a mono ligation system in which a set of three antibodies conjugated with hairpin structure oligonucleotides serve as unfolding proximity probes. Among the three probes, one is immobilized on a glass slide by hybridization to a long oligonucleotide affixed on the slide that later serves as the RCA primer; one carries a barcode sequence and the other serves as ligation template once probes are all unfolded; b) demonstrates how the system was validated first with a simplified version in which only one probes require an unfolding reaction. VEGF and Mouse IgG were applied as target proteins and spiked in buffer with a ratio of 1:1 (c) and 1:10 (d) and 0 protein (e). After on chip proximity ligation and RCA, the amplified products were visualized by calling the first base using Illumina sequencing reagents. Base 'T' encoding for VEGF appears in both red and green channels, and base 'G' encoding for Mouse IgG appears in only green channel.

Figure 23:
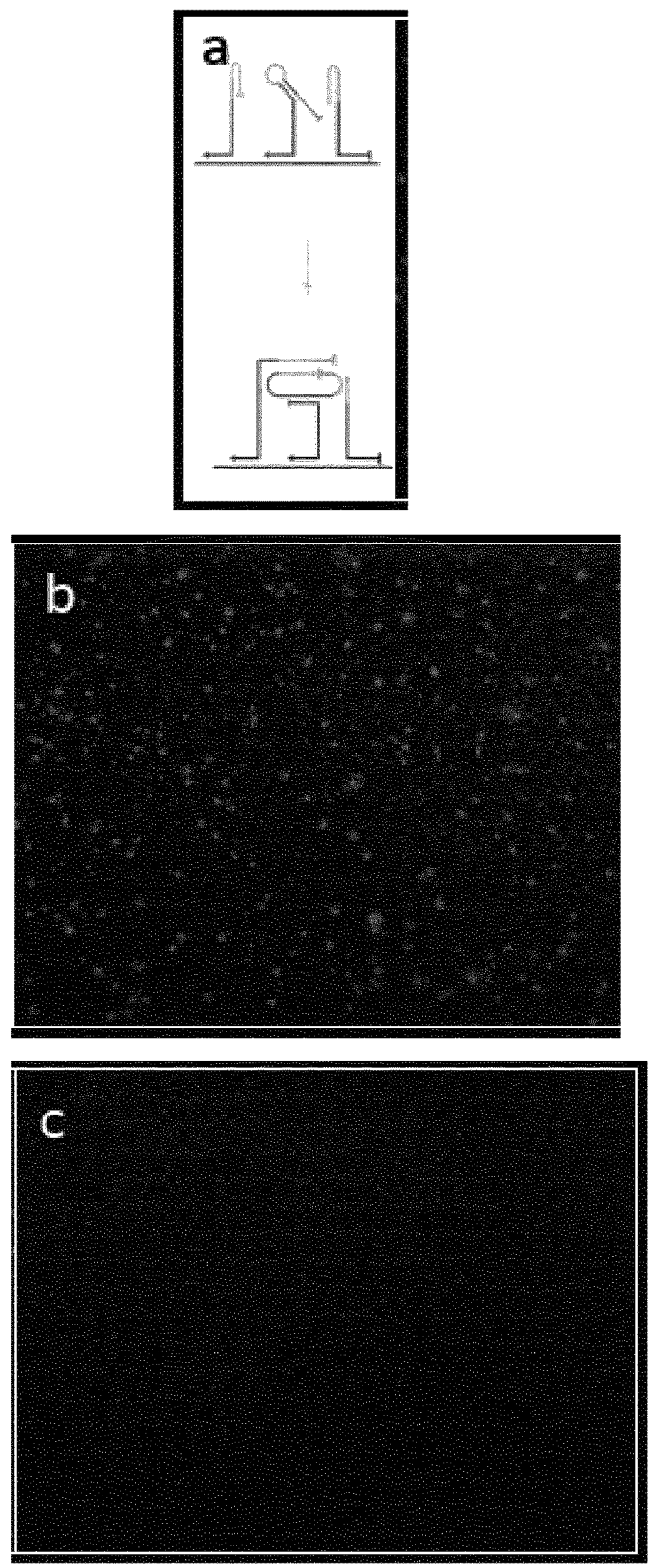

FIG. 23 shows an RNA detection using unfolding proximity probes with single molecule resolution, wherein a) shows an illustration of RNA detection by unfolding probes. A synthetic template was applied as validation system. Blobs were detected when UNG was applied (b); in contrast no blobs were detected when UNG was absent in the reaction mix (c).

FIG. 24 shows a set of three unfolding proximity probes targeting an individual nucleic acid molecule (a) and protein (e). After enzyme digestion, probes are unfolded and the remaining strands are allowed to hybridize to each other, based on sequence complementarity (b). Reporter DNA molecules are circularized by DNA ligation (c) followed by RCA and detection in situ (d). The probes used to detect synthetic DNA induce detection signals in the presence of templates and enzymes (f) whereas no signals were observed when either templates (g) or enzymes (h) were absent.

Figure 25:
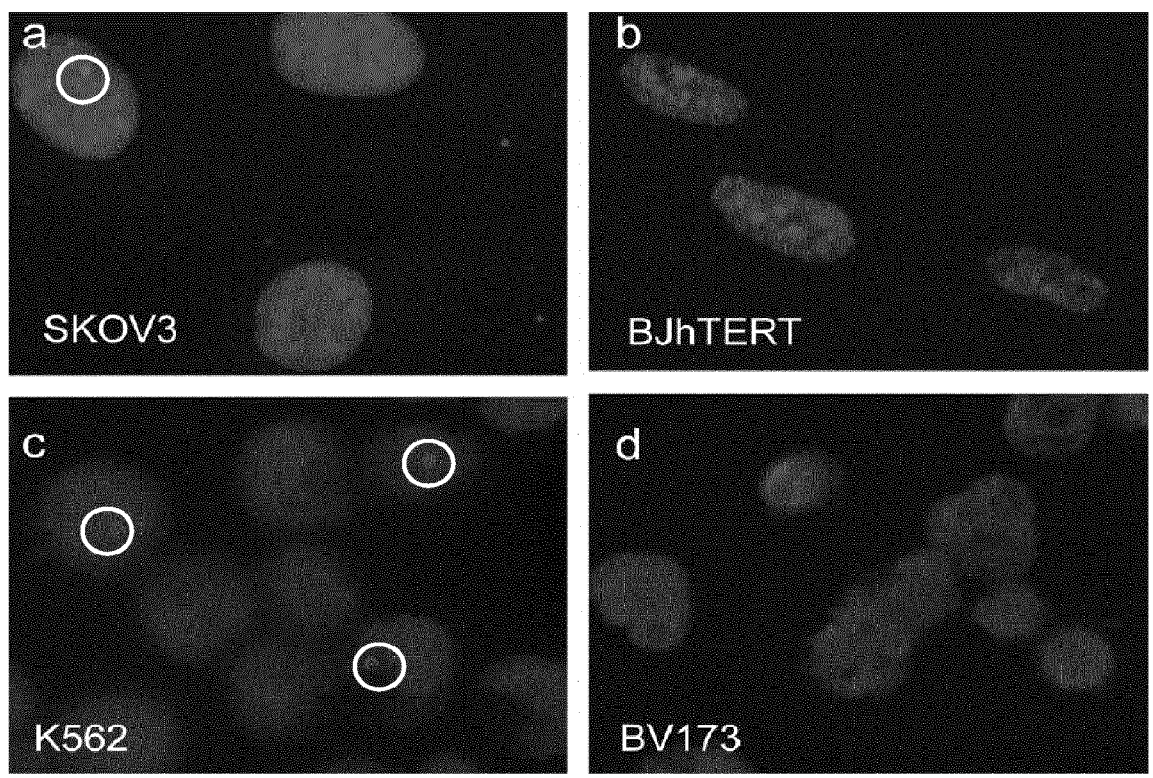

FIG. 25 shows the results of unfolding proximity probes directly targeting individual mRNA molecules in cells. Transcripts of HER2 (circled) were observed in the cell line SKOV3 (a) but they were not detectable in cell line BJhTERT (b). BCR-ABL fusion transcript b3a2 were detected in the cell line K562 (circled), carrying the targeted form of the fusion transcript (c) but they were not detectable in the cell line BV173 carrying a form of the fusion transcript lacking a target sequence for one of the unfolding proximity probes (d).

Figure 26:
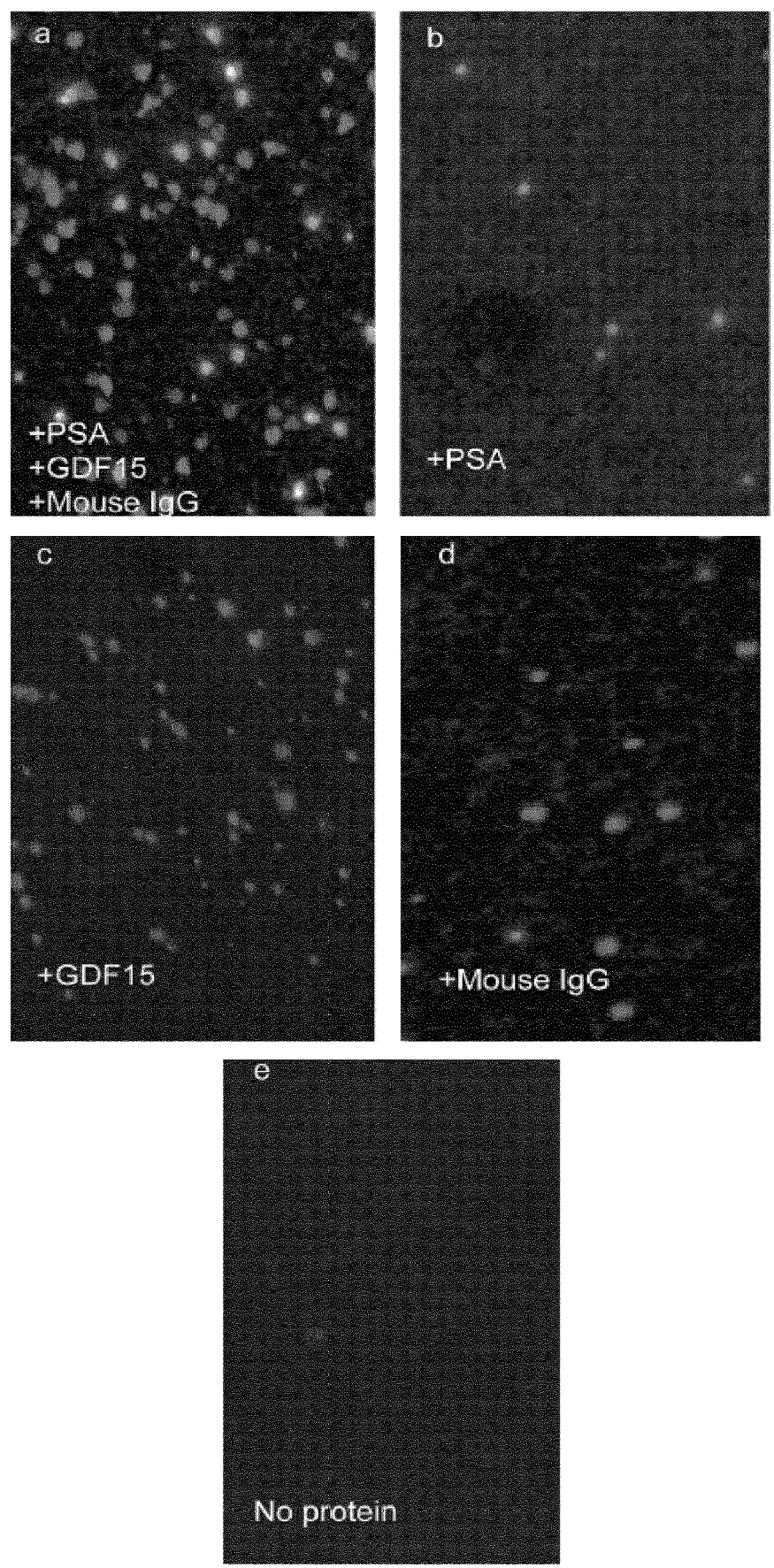

FIG. 26 shows the results of an assay in which three protein analytes, namely recombinant PSA, GDF15 and mouse IgG, were captured and reported by three-sets of unfolding proximity probes and in situ blob sequencing, (a) all three proteins were present, diluted in buffer, (b-d) proteins were individually spiked in, (e) none of the three proteins were spiked in.

EXAMPLES

Example 1

As described above, the methods described herein are based on the development of a modified in situ proximity ligation assay (PLA). The below examples describe the process of developing in situ PLA for analyses of PDIs (protein-DNA interactions) in situ, whereby three assays were evaluated and the efficiency and selectivity of each assay was compared. The comparison involved the investigation of the proximity of histone H3 protein to genomic Alu-repeats as a model system. The advantage of this model system is that histone H3 is present in large numbers and thus often present in conjunction with Alu-repeats; an abundant sequence in the genome. The 26 bp Alu-consensus sequence that we chose as a target sequence is present in humans, but no exact copies are present in mice. We compared a design using hybridization to a more stringent design based on ligation of padlock probes for DNA target recognition. The work presented here provides a basis for a novel approach to study epigenetic alterations in situ and as described above, the methods and probes that have been development are useful in a wide variety of assays for detecting an analyte in a sample.

Methods

Cell Culture

Human TERT immortalized fibroblasts (BJhTert) and mouse fibroblasts (NIH3T3) were seeded on 8-well collagen coated chamber slides (BD Bioscience), 33000 cells per well in Modified Eagle Medium (Gibco, for BJhTert cells) or Dulbecco's Modified Eagle Medium (Sigma, for NIH3T3 cells)+10% fetal calf serum (FCS, heat inactivated, Sigma) and incubated overnight at 37° C.

Fixation and Permeabilization

Cells were put on ice for 10 min and subsequently washed twice with ice cold PBS, 5 min each (900 µl per well). The cells were fixed with 2% (w/v) paraformaldehyde (PFA, Sigma) in PBS for 30 min on ice. After a short wash with 900 µl ice cold PBS per well, the cells were permeabilized with ice cold 70% ethanol for 30 min on ice. Next, the silicon masks of the chamber slides were removed and the slides were dried at room temperature. Subsequently the slides were rehydrated in PBS for 10 min and cells were permeabilized in 2.9 µM pepsin (Sigma, freshly diluted from 580 µM stock) in 37° C. warm 0.1 M HCl (Sigma) for 65 sec at 37° C. Prior and subsequently to a wash in 1 M NaCl, 0.1 M Tris-HCl pH 7.5 for 60 sec at 37° C., the slides were washed twice for approximately 1 min in PBS and finally dried by an ethanol series (70%/85%/99.6%, 2 min each) and a short spin in a table centrifuge. A hydrophobic barrier pen was applied to the borders of the wells and 8-chamber secure seals (9 mm in diameter, 0.8 mm deep; Grace Bio-Labs) were attached to the slides. The cells were rehydrated in washing buffer (100 mM Tris-HCl (pH 7.6), 150 mM NaCl, 0.05% Tween20 (Sigma)) for 10 min at 37° C. Thereafter, all incubations were done in a moisture chamber, and the wells were sealed with q-PCR tape when incubation time exceeded 30 min. Genomic DNA was digested with 0.5 U/µl AluI (New England Biolabs (NEB)) in 1×NEB-buffer-4 and 0.2 µg/µl BSA (NEB) for 10 min at 37° C. All subsequent washes were performed by removing the incubation solution from the wells first, and then flushing the wells with approximately 500 µl of the appropriate washing buffer. After the AluI-treatment, the cells were washed in washing buffer before the DNA was made partially single stranded by treatment with 0.2 U/µl lambda-exonuclease (NEB) in 1× lambda-exonuclease buffer (NEB). 0.2 µg/µl BSA and 10% glycerol (Sigma) for 30 min at 37° C. The cells were washed in washing buffer prior and subsequently to a post-fixation step with 1% (w/v) PFA in PBS for 5 min on ice.

Immunofluorescence

Cells were treated as described above. The cells were blocked in Starting Block T20 PBS (Pierce) containing 2.5 mM L-cysteine (Sigma) and 2.5 ng/µl sonicated salmon sperm DNA (Invitrogen) for 1 h at 37° C. Afterwards, 2.5 ng/µl of the primary rabbit-anti-histone H3 antibody (#1791, Abcam) was applied in blocking buffer at 4° C. overnight. The wells were washed in TBS (10 mM Tris-HCl, 150 mM NaCl, pH 7.7) with 0.05% Tween20 (TBS+T, 1000 µl per well) before 7.5 ng/µl donkey-anti-rabbit-FITC F(ab')2 fragment (Jackson Immunoresearch) was added in 2×SSC, 0.25 µg/µl BSA, 7.5 ng/µl poly(A) (Sigma), 0.05% Tween20 and incubated for 30 min at 37° C. Finally, the slides were rinsed once in TBS, secure seals were removed, and the slides washed 2×10 min in TBS before they were spun dry and mounted in Vectashield mounting medium (Vector) containing 100 ng/ml DAPI.

Conjugation of Anti-Rabbit PLA-Probe

One hundred µg donkey-anti-rabbit (Jackson ImmunoResearch) was dialyzed against PBS in a dialysis cup (Slide-A-lyzer Mini dialysis units 7,000 MWCO. Pierce) over night at 4° C. The antibody was subsequently concentrated to approximately 20 µl by centrifugation in Amicon Ultra 0.5 ml 10K; Ultracell 10K Membrane (Millipore), prewashed in PBS. Then SMCC (Pierce) freshly dissolved in DMSO (Sigma), was added in ~25× molar access over antibody for 2 h at room temperature. The PLA oligonucleotide (5' Thiol—GTC TTA ACT ATT AGC GAT ACG GTC TCG CAG ATC GCT GAC AGA ACT AGA CAC 3' (SEQ ID NO: 1). HPLC-pure, Biomers) was degassed for 5 min at 80° C., chilled, and reduced by incubation with 50 mM DTT (50 µM final concentration of the PLA oligonucleotide) for 1 h at 37° C. Afterwards the volume was filled up to approximately 50 µl through addition of buffer A (55 mM phosphate buffer, 150 mM NaCl, 20 mM EDTA, pH 7.0). Buffer A was also used to pre-wash G-50 columns (GE Healthcare). Both antibody and oligonucleotide were then purified over three such columns to remove activating reagents. Immediately afterwards, antibody and oligonucleotide were mixed and dialyzed against PBS over night at 4° C.

Hybridization Based In Situ PLA

Cells were fixed and permeabilized as described above before incubation with 200 nM Hyboligonucleotide, the "first" proximity probe (5' GCC TCC CAA AGT GCT GGG ATTACA GGA AAA AAC ATG GAT GTT CTT GAC ATG GCA ATG ACG CTA A 3' (SEQ ID NO: 2), PAGE pure, Integrated DNA Technologies (IDT), target complementary parts are shown in italic, mismatches to the mouse sequence are shown in bold) in 1×T4 DNA ligation buffer (10 mM Tris-acetate pH 7.5, 10 mM magnesium acetate, 50 mM potassium acetate), 250 mM NaCl, 0.25 µg/µl BSA and 0.05% Tween20 for 30 min at 37° C. Slides were then washed with washing buffer and subsequently in 2×SSC+ 0.1% Tween20 for 5 min at 37° C. Afterwards the buffer was changed to TBS+T. The cells were blocked in Starting Block T20 PBS containing 2.5 mM L-cysteine and 2.5 ng/µl sonicated salmon sperm DNA for 1 h at 37° C. Next, 2.5 ng/µl of the primary rabbit-antihistone H3 antibody or rabbit IgG (Jackson Immunoresearch) were applied in blocking buffer at 4° C. overnight. The wells were washed in TBS+T (1000 µl per well) and 2.5 ng/µl secondary anti-rabbit-PLA-probe (the "second" proximity probe) was preincubated in blocking buffer for 30 min at room temperature and then applied to the slides for 1 h at 37° C. After a wash in 10 mM Tris-HCl pH 7.5, 0.1% Tween20 for 5 min at 37° C. and a short rinse in TBS+T, two oligonucleotides (5' phosphate—AGC GAT CTG CGA GAC AGT GAA TGC GAG TCC GTC TAA GAG AGT ACA GCA GCC GTC TTA GCG TCA TTG CCA T 3', (SEQ ID NO: 3) PAGE pure, IDT: 5' phosphate—GTC AAG AAC ATC CAT GAA AGT GTC TAG TTC TGT C 3', (SEQ ID NO: 4) PAGE pure, IDT) were applied at a final concentration of 125 nM for 30 min at 37° C. in 1×T4 DNA ligation buffer, 0.05 U/μl T4 DNA ligase (Fermentas), 1 mM ATP (Fermentas), 0.25 μg/μl BSA, 250 mM NaCl and 0.05% Tween20. The oligonucleotides consist of a padlock probe and a gap oligonucleotide, such that the ligation of the padlock probe to produce a circular oligonucleotide was templated by the hyboligonucleotide and the nucleic acid domain of the anti-rabbit-PLA probe, as depicted in FIG. 17Aiii. The wells were washed with TBS+T before RCA with 1 U/μl phi29 DNA polymerase (Fermentas), 1×phi29 buffer (Fermentas), 0.25 mM dNTP (Fermentas), 0.2 μg/μl BSA, 5% glycerol and 1:1000 mouse-anti-histone H3 (phospho S10) (Abcam) for 1.5 h at 37° C. The nucleic acid domain of the first proximity probe was used as the primer for RCA. Detection was done after a wash with TBS+T with 250 nM detection oligonucleotide (5' Alexa Fluor 555—CAG TGA ATG CGA GTC CGT CT 3', (SEQ ID NO: 5) HPLC pure, TriLink) in 2×SSC, 0.25 μg/μl BSA, 7.5 ng/μl poly(A), 0.05% Tween20 and 6.5 ng/μl donkey-anti-mouse-FITC F'ab2-fragment (Jackson Immunoresearch) for 30 min at 37° C. Finally, the slides were rinsed once in TBS, secure seals were removed, and the slides washed 2×10 min in TBS before they were spun dry and mounted in Vectashield mounting medium containing 100 ng/ml DAPI.

Detection of Hybridization Oligonucleotides by Padlock Probes

Cells were treated as described for the Hybridisation based in situ PLA until the slides had been blocked. Then 125 nM padlock oligonucleotide (5'phosphate—TGT CAA GAA CAT CCA TGT CAG TGA ATG CGA GTC CGT CTA AGA GAG TAG TAC AGC AGC CGT TTA GCG TCA TTG CCA 3', (SEQ ID NO: 6) HPLC pure, IDT)—a padlock probe directed against the free part of the Hyb-oligonucleotide—was applied in 1×T4 DNA-ligation buffer, 0.25 μg/μl BSA, 0.05 U/μl T4 DNA ligase, 0.05% Tween20, 1 mM ATP and 250 mM NaCl and incubated for 30 min at 37° C. RCA, detection and mounting were performed as described above.

Genomic DNA-Templated In Situ PLA

Cells were fixed and permeabilized before the slides were blocked and incubated with primary antibody and secondary PLA probes (the "first" proximity probe), as described for the Hybridisation based in situ PLA. After washing, 200 nM GenomeTemplate oligonucleotide 1 (5' phosphate—CT G GGA TTA CAG GAA AAA AAG AGT GTC TAG TTC TGT C 3', (SEQ ID NO: 7) PAGE pure, IDT, target complementary parts are shown in italic, mismatches to the mouse sequence are shown in bold) and 200 nM GenomeTemplate-oligonucleotide 2 (5' phosphate-CGC TAA TAG TTA AGA CGC TCA GTG AAT GCG AGT CCG TCT AAA AAA AGC CGC CCA AAG TG 3', (SEQ ID NO: 8) PAGE pure, IDT, target complementary parts are shown in italic, mismatches to the mouse sequence are shown in bold, the G/A mismatch utilized for MutY-cleavage is shown with an underline) were applied in 1×T4 DNA ligation buffer, 0.25 μg/μl BSA, 0.05% Tween20 and 250 mM NaCl and incubated for 30 min at 37° C. The two oligonucleotides form a two-part padlock probe that may be viewed as the "second" proximity probe. After a washing step with washing buffer, 0.05 U/μl T4 DNA ligase in T4 DNA-ligation buffer, 1 mM ATP, 0.25 μg/μl BSA, 250 mM NaCl and 0.05% Tween20 was applied for 30 min at 37° C. The slide was washed in 2×SSC+0.05% Tween20 for 5 min at 37° C. and subsequently in TBS+T. Next, the probes were digested with MutY/endonuclease IV (EndoIV) using 0.64 μM MutY protein (USB). 0.1 U/μl EndoIV (Fermentas) in MutY buffer (20 mM Tris-HCl pH 7.6, 30 mM NaCl, 1 mM EDTA, 100 mM KCl, 1 mM DTT) and 0.5 μg/μl BSA for 30 min at 37° C. to generate a free 3' end of genomic DNA capable of priming the RCA of the circularised padlock probe. After an additional washing step in TBS+T 125 nM of the additional gap oligonucleotide (5' phosphate—AGC GAT CTG CGA GAC CGT AT 3', (SEQ ID NO: 9) HPLC pure, Biomers) in 0.05 U/μl T4 DNA ligase, 1×T4-ligation buffer, 1 mM ATP, 0.25 μg/μl BSA, 0.05% Tween20 and 250 mM NaCl were incubated for 30 min at 37° C. The nucleic acid domain of the first proximity probe acts to template the ligation of the padlock probe, via the gap oligonucleotide, as depicted in FIG. 18A. RCA (primed by the genomic DNA), detection and mounting were performed as described above, except that 250 nM of an additional detection oligonucleotide (5' Cy5—AGC GAT CTG CGA GAC CGT AT 3', (SEQ ID NO: 10) HPLC pure, IDT) were added to the mix.

Horn Probe-Based In Situ PLA

The horn probe was made by ligation of two parts A (5' phosphate—CT G GGA TTA CAG GAA AAA AAG AGT GTC TAG TTC TGT CUT AAA AAA ATA AGA CAG AAC UAG ACA CUC TAA AAA AAG CGT CUT AA 3' (SEQ ID NO: 11)—PAGE pure, IDT, target complementary parts are shown in italic, mismatches to the mouse sequence are shown in bold) and B (5' phosphate—CTA UTA GCG ACA AAA AAG UCG CTA ATA GTT AAG ACG CTC AGT GAA TGC GAG TCC GTC TAA AAA AAG CCG CCC AAA GTG 3' (SEQ ID NO: 12)—PAGE pure, IDT, target complementary parts are shown in italic, mismatches to the mouse sequence are shown in bold, the G/A mismatch utilized for MutY-cleavage is shown with an underline). The two oligonucleotides were mixed at a final concentration of 4.4 μM, 1×T4 DNA-ligation buffer and 2 mM ATP were added. The oligonucleotide mix was first incubated at 90° C., then 65° C. for 10 min each. After cooling to room temperature, 0.025 U/μl T4 DNA ligase was added. The sample was ligated for 30 min at 37° C. and then incubated for 10 min at 65° C. to inactivate the ligase.

Cells were fixed and permeabilized as described above, before incubation with 200 nM horn probe (the "first" proximity probe) in 1×T4 DNA ligation buffer, 250 mM NaCl, 0.25 μg/μl BSA and 0.05% Tween20 for 30 min at 37° C. Afterwards the slides were washed in washing buffer and the horn probe ligated with 0.25 U/μl Amp-ligase (Epicentre) in 1×Amp-ligase buffer (20 mM Tris-HCl (pH 8.3), 75 mM KCl, 10 mM MgCl$_2$, 0.5 mM NAD (Sigma), 0.01% Triton X-100 (PlusOne)), 0.25 μg/μl BSA and 5% glycerol for 30 min at 45° C. Slides were then washed and treated with primary antibody and secondary PLA probe (the "second" proximity probe) as described above. Next, probes were digested with MutY/EndoIV and uracil-DNA glycosylase (UNG) for PDI detection with 0.64 μM MutY glycosylase, 0.1 U/μl EndoIV, 0.05 U/μl UNG (Fermentas) in MutY buffer and 0.5 μg/μl BSA for 30 min at 37° C. The addition of the UNG results in the unfolding of the horn probe, as shown in FIG. 19A. For samples where the padlock probe was applied as DNA-detection probe only. UNG was omitted from this step. All subsequent steps were done as described above for Genomic DNA-templated in situ PLA.

Image Acquisition and Pre-Processing

Images were acquired using a Zeiss Axioplan 2 epifluorescence microscope, the AxioCam MRm CCD sensor and a 40×/1.3 Oil PlanNeofluar objective together with filters for DAPI, FITC, Cy3 and Cy5. Imaging positions were chosen using the FITC channel, avoiding cells showing staining for phosphohistone H3 S10, a mitotic marker. For each condition, z-stacks of 7 images, 0.275 μm apart were acquired at four positions of the well. Since cells in interphase are comparably flat, z-stacks were collapsed by taking maximum intensity projections of individual z-slices, while the purpose of imaging more than one focal plane was to avoid longitudinal chromatic aberrations. Lateral chromatic aberrations were corrected using a rigid geometrical transformation. Background illumination was reduced by subtracting the median intensity from Cy3 and Cy5 channels respectively.

Image Analysis

To quantify PDIs on a per cell basis, individual cells were identified as well as point-source signals. Cell nuclei imaged in DAPI were segmented from the image background by intensity thresholding and touching nuclei masks were separated based on shape. Individual signals were thereafter detected in the Cy3 (red) and Cy5 (green) channels separately using a point-source signal detection method. The method consists of two parts, a detector, which is a cosine filter to enhance the signals, and a verifier, which is a sine filter to validate the result from the detector. The results of signal detection in the Cy3 and Cy5 channels were combined, and the ratio of fluorescence intensity from the two colour dyes was extracted from each detected signal. Signals were thereafter classified as red, green or dual coloured based on the ratio distribution of green to red intensity. Compared to classification methods based on intensity thresholding, this type of ratio-based classification ensures that strong and weak signals are assigned to the same class. For the hybridization based in situ PLA single coloured Cy3 signals were regarded as detected PDIs, while for the genomic DNA-templated in situ PLA and for the horn probe based in situ PLA only double coloured (Cy3 and Cy5) signals were regarded as true PDIs. For each of the experiments performed under new conditions, image data were divided into a training and a test set. The training sets were used for fine tuning parameters related to signal size and intensity in the image analysis pipeline, followed by application of the algorithms to the larger test sets in order to present results per cell population.

Results

The proximity ligation assays described above were used to detect the co-location of a DNA-binding protein and a specific short genomic DNA-sequence in individual fixed cells, and these different assays (as depicted in FIGS. 17-19) were evaluated with regard to their selectivity. The cells to be investigated for specific PDIs were PFA-fixed and permeabilized with ethanol, followed by a pepsin treatment and a wash in high salt to render the nuclei more accessible for probing. Then genomic DNA was digested by AluI restriction enzyme treatment. As genomic sequence detection by hybridization requires single stranded DNA the cells were then treated with lambda-exonuclease, to use its 5'-3' activity in order to generate single stranded overhangs with free 3' ends at the sites of digestion. As proof-of-principle we choose to investigate the proximity between histone H3 and a 26 bp Alu-consensus sequence (5' CCTGTAATCCCAG-CACTTTGGGAGGC 3' (SEQ ID NO: 13)), present in approximately 60,000 copies per cell in humans as determined by searching perfect sequence-matches in the human genome sequence (NCBI 36, March 2006 assembly). Although the exact sequence is not present in mice, their genomes contain a sequence similar to the human 26 bp Alu-consensus sequence (5' CCTTTAATCCCAG-CACTCGGGAGGC 3' (SEQ ID NO: 14), differences to the human sequence are indicated in bold) in approximately 6,000 copies (perfect sequence matches per mouse genome. NCBI 36, October 2006 assembly), which is not present in humans. This provided a good model for studying the selectivity of probing. We confirmed that the antibody used to target the histone H3 stains human and mouse nuclei approximately equally using immunofluorescence on human (BJhTert) and mouse (NIH3T3) fibroblasts (FIG. 17B).

Hybridization-Based In Situ PLA

In situ PLA has previously been used for detection of individual protein-protein interactions. To extend the application to specific PDIs we first investigated a simple hybridization approach to detect the genomic DNA sequences. In this design we used an anti-rabbit immunoglobulin antibody conjugated with an oligonucleotide as a PLA probe to detect a primary rabbit antibody directed against histone H3 (i.e. the proximity probe was indirectly bound to the analyte). The other PLA probe was an oligonucleotide, complementary to the target sequence and extended with a sequence required for the PLA reaction (FIG. 17A). To investigate the specificity of the DNA-directed PLA-probe we used it for hybridization to human cells carrying the target sequence, and to mouse cells, that carry a similar but non-identical sequence in approximately 10-fold fewer copies. The bound probes were then visualized by RCA, using a padlock probe directed to the free 3' end of the hybridization probe. Padlock probes are single stranded oligonucleotides that hybridize to their target sequences with their 5' and 3' end facing each other. Upon perfect hybridization the ends can be joined by ligation, creating a circular DNA-molecule which may then be locally amplified by phi29 DNA polymerase through RCA. The resulting single stranded DNA molecule, consisting of approximately 1000 complementary repeats of the original circle, forms a sub-μm sized bundle of DNA. We detected these RCA products by hybridization of fluorescence labelled oligonucleotides. As the fluorophores are concentrated in a very small volume they were easily distinguished from background fluorescence and appeared as bright spots by fluorescence microscopy. Every detected RCA product gives rise to one distinct spot and enumeration of these enabled quantification in single cells. Prominent detection signals confirmed that the probe indeed hybridized to DNA in the nuclei of the human cells. However, signal concentration was so high, that individual RCA products could not be distinguished. Reaction products were also observed in the mouse cells, despite their lack of the exact target sequence (the mouse sequence differed from the human sequence in c.4G>C, c.18deT and c.19T>C positions in the region targeted by the probe) (FIG. 17Bii).

To detect the co-location of histone H3 with Alu-repeats in genomic DNA, the DNA-directed PLA probe was used together with the primary antibody and the secondary PLA-probe described above. Proximal binding of these two probes templated the hybridization and ligation of two subsequently added oligonucleotides, creating a circular DNA molecule, which was then replicated by RCA and detected using fluorescent hybridization probes as above (FIGS. 17C and D). Hybridization-based in situ PLA produced ~160 signals per cell in human cells, a more than 5-fold increase as compared to ~30 signals per cell observed in mouse cells lacking this precise genomic sequence (FIG. 20). When an irrelevant rabbit IgG was substituted for the primary antibody, or when the primary antibody or the DNA-binding PLA-probe were omitted negligible numbers of signals were detected (median=0, upper percentile s 1), regardless of which cell line was used (data not shown).

Genomic DNA-Templated In Situ PLA

In order to improve the selectivity of detection of the targeted genomic DNA sequence, we decided to utilize the genomic DNA sequence itself to template the ligase-dependent circularization of oligonucleotide probes. In this design the single stranded genomic DNA will thus act as a PLA probe. For this second design, the primary antibody and secondary PLA-probe were applied to the cells with fixed and partially digested DNAs. This genomic DNA provided one of two templates required for circularization of the pair of oligonucleotides (two part padlock probe), the other template being the oligonucleotide attached to the PLA-probe (FIG. 18A). An intentional G/A mismatch in the probe-target hybrid was used to enzymatically cleave the genomic sequence at the site of probe binding using the mismatch-specific MutY glycosylase (MutY) and endonuclease IV (EndoIV). This gave rise to a free 3' end in the genomic DNA sequence that can be used to prime the RCA. To ensure that the signals indeed reflect bona fide protein-DNA interactions, we designed the reactions so that a short so-called "gap" oligonucleotide was included in the circular DNA molecule, templated by the oligonucleotide attached to the anti-rabbit Immunoglobulin antibody. This sequence provided a second detection site in the RCA products in addition to the one already incorporated in the padlock probe oligonucleotide. The inclusion of this extra DNA segment allowed us to distinguish any padlock probes that had been circularized without the participation of the anti-histone antibody. We ensured that both segments were reflected in the RCA product by detecting these two motifs using hybridization probes with distinct fluorescence. Thus, only RCA products detectable with probes directed against both segments were considered indicative of PDI (FIGS. 18B and C). As expected, the use of genomic DNA as a PLA-probe increased the proportion of signals in human cells 13-fold as compared to mouse cells for which signals decrease to 5 signals per cell (FIG. 20). However, with this more stringent probing, the total number of signals found in human cells decreased to ~80 signals per cell. A median of 0 signals (upper percentile ≤1) was observed in both cell lines when an irrelevant rabbit IgG was applied instead of the primary antibody, or when no primary antibody or circularization oligonucleotides were added.

Horn Probe-Based In Situ PLA

Even though genomic DNA-templated in situ PLA improved signal detection selectivity, it still produced false positive signals in the mouse cells despite the absence of the exact target sequence. As discussed above, hybridization of the circularization oligonucleotides (two part padlock probe) to similar but not identical sequences might allow ligation and we thus wanted to replace T4 DNA ligase with a more stringent ligase, i.e. Amp-ligase, which tolerates higher temperatures and provides more specific target recognition. However, antibodies are likely to be sensitive to temperatures substantially exceeding 37° C. Hence, in order to use the more specific Amp-ligase the reaction scheme had to be changed. The padlock probe (in this case a horn probe, as discussed below) was first hybridized and ligated at the higher temperature of 45° C. prior to antibody incubation at 37° C. The DNA circle was formed from using a one-part padlock probe instead of using a two-part padlock probe as described above. Thereby both target-complementary sequences were linked into one molecule. However, when using a one-part padlock probe, the padlock probe must have partial complementarity to the PLA probe used for detecting the protein component of the PDI, but these reagents must not be brought together due to this complementarity during the incubation with the PLA-probe.

To overcome this obstacle we have found a general approach where one of the DNA reagents, here the padlock probe, includes two hairpin structures shielding the complementarity to the PLA-probe used for protein detection, a so-called horn probe. Several uracil bases were incorporated into one strand of each hairpin structure to provide a substrate for enzymatic digestion. This allowed us to liberate the sequences of the padlock probe that are complementary to the PLA probes after both probes had independently bound their targets (FIG. 19A). As a consequence, the padlock probe could be hybridized onto the genomic DNA and ligated by Amp-ligase without interfering with the subsequent primary antibody and the secondary PLA-probe incubations. Only when all probes had bound were the complements in the hairpin-structures removed by digestion with uracil-DNA glycosylase (UNG), to remove uracil bases, and the DNA-backbone was cut at the abasic sites by EndoIV-treatment. This liberated hybridization templates for adjacent PLA-probes that templated the ligation of the remaining parts of the horn probe to recreate circular, now somewhat smaller, DNA molecules. In the same step the G/A-mismatches between genomic DNA and circularized probes were MutY/EndoIV-cleaved to create a free 3' end in the genomic DNA at the site where the circularized probe had bound. As described for the genomic DNA-templated in situ PLA, incorporation of an additional sequence element (a gap oligonucleotide) in the horn probe was required to distinguish correctly reacted probes. This time the incorporation of the gap oligonucleotide—resulting in double coloured RCA products—also served to control for the UNG/EndoIV cleavage since the horn probe alone also could be amplified by RCA, if not digested by UNG/EndoIV. In that case it served as a regular padlock probe, detecting genomic DNA but independent of protein binding (FIG. 19B), while double coloured signals represented proximity between the DNA-sequence and the target protein (FIG. 19B).

In this manner, the proximity between Alu sequences and histone proteins interacting with the DNA was visualized with high selectivity, producing ~25 PDI-signals per human cell, while negligible numbers of signals were observed in the mouse cells, rendering the detected signal in human cells 500 times higher than in mouse cells (FIGS. 19C and 20). As above none of the technical controls utilizing irrelevant rabbit IgG, omitting the primary antibody or the DNA-binding PLA-probe resulted in signals (both median and upper percentile equals zero) in either cell types (data not shown). Results were similar when detection of genomic DNA using the hairpin-containing padlock probe (a horn probe) was compared to those using a regular padlock probe without hairpin segments, hence the hairpin structures did not impair detection or amplification (data not shown).

Discussion

The Alu sequence targeted in the assay described is present in ~60,000 copies in the human genome and histone H3, a component of the nucleosome is certainly located in proximity to most or all of these. To render the nucleus accessible to all reagents required for detection, the nuclear membrane had to be permeabilized and some proteins removed. Here we had to find a balance between gaining access to the target sequence and retaining proteins of interest in place. Therefore, the fixation and permeabilization steps required careful titrations that may need be redone for every new protein and sequence of interest.

We chose to exclude cells stained by the mitotic marker anti-histone H3 (phospho S10) from our analyses to avoid a source of variation among the investigated cells. When Alu-sequences were targeted with padlock probes, the detection efficiency of ~0.13% implies that a great part of the DNA is not accessible for probing under the conditions we used. Further work to increase the accessibility of the DNA will be required to improve the efficiency of the method presented herein for detection of proteins binding single copy genes.

As expected, the hybridization based approach for detecting the target DNA sequence shown herein was the least selective, producing ~160 signals per human cell, but also ~30 signals per mouse cell. Using genomic DNA directly to template one of the two ligation reactions required to form the amplifiable DNA circles instead of hybridizing an oligonucleotide to the target sequence and utilizing this as template for ligation, increased the ratio between signals detected in human and mouse cells to ~13. At the same time the number of signals in human cells dropped by approximately 50% compared to hybridization based in situ PLA. We assume that most of the signals lost were false positive signals, since the signals from the negative control mouse cells dropped by 80%. As restriction cleavage and exonucleolysis produce a substantial amount of single stranded DNA, increasing the risk of cross-hybridization of the circularization probes, we ensured that only RCA products resulting from recognition of both the genomic target sequence and the bound protein were scored. This was achieved by allowing the histone H3 bound PLA-probe to guide the incorporation of an additional "gap" oligonucleotide in the circularized (padlock or horn probe) DNA molecules. Thereby, two probes, labelled with distinct fluorophores, could be used to detect RCA products. One recognized a motif from the circularization (padlock or horn) probe specific for genomic DNA, and one revealed the presence of the additional "gap" oligonucleotide contributed by the anti-histone antibody. In the data analysis, only double coloured RCA products were regarded as true signals. Signals found outside the nucleus, in the cytoplasm or outside the cells were also disregarded from the analyses.

In order to further improve the selectivity of the assay to discriminate between closely related sequences we switched to the thermostable Amp-ligase, necessitating a more elaborate probe design. Amp-ligase requires a higher temperature and is more sensitive to mismatches at the ligation site than T4 DNA ligase. As a consequence, ligation of the DNA-binding probe would need to occur before the protein is detected since the antibodies do not endure incubations at temperatures substantially higher than 37° C. However, if the circularization (padlock probe) oligonucleotides were applied and ligated prior to binding of the PLA-probe, then the oligonucleotide carried by the PLA-probe intended for protein detection could hybridize to the DNA-bound circularization oligonucleotides and be brought in proximity independently of the presence of the appropriate target protein. Hence, we had to mask the PLA-probe complementary parts of the DNA-binding probe by introducing two hairpin structures, which hide the complementary parts of the oligonucleotide. With this horn probe based in situ PLA we observed a 500-fold increase in signal count in human cells as compared to mouse cells. Comparing the number of PDI signals and Alu-sequences detected by padlock probe based in situ PLA 40% of all detected Alu-sequences appear to be in close proximity to a histone H3.

The combination of horn probes for DNA detection with oligonucleotide-conjugated antibodies for protein detection thus resulted in selective detection of protein-DNA complexes via a proximity ligation reaction. Such methods will be helpful to identify cells with specific PDIs and epigenetic changes at certain sequences, and their location within a tissue section. However, it is evident that the methods and probes described herein will be useful for the detection of analytes in general and are not limited only to detection of PDIs. Thus, combined with related methods to detect genes, transcripts, and proteins at the single cell level much more detailed analyses of cellular function will become possible. In a further perspective new diagnostic opportunities may arise as studies of the regulation of gene expression at the single cell level are enabled.

Example 2

On-Chip Proximity Ligation Assay (PLA) with Unfolding Probes and In Situ Blob Sequencing Readout A first proximity probe (or capture probe) is immobilized on a glass slide by ligation to an oligonucleotide on the slide surface (FIG. 21a) or hybridization (FIG. 22a). Target protein (analyte) and a pair of proximity probes conjugated with nucleic acid domains comprising a hairpin-structure and a six nucleotide barcode motif are added sequentially. After the formation of analyte-probe complex, a nicking enzyme which recognizes the specific sequence in the hairpin structure is applied. The unfolded oligonucleotides, if in proximity, are able to form a circular DNA molecule. The oligonucleotide immobilised on the solid support then serves as the primer for rolling circle amplification (RCA). The DNA circles are amplified up to approximately 1000 copies within one hour. The RCA products remain linked to the glass slide. After hybridization with sequencing primers, the barcode sequences, which are downstream of the sequencing primer binding sites, are then recoded by sequential incorporation of nucleotides that are labelled with different fluorophores. Detection of the fluorescent signal correspondence to the presence of the analyte.

Methods & Materials

Antibody Immobilization on Glass Slides

Amined modified oligonucleotides (Biomers) were printed on TRIDIA™ codelink slide (SurModics). Each slide was printed with 14 sub-arrays of 20×20 features. The array printing and blocking protocols were described by Ericsson et al. Secure-Seal 16 (Grace Bio-labs) was attached to the slide prior to use. Forty μl of 50 nM capture conjugates were added to each reaction chamber and incubated over night at 4° C. Next, each well was gently flushed with 1 ml 1×PBS and dried. In the immobilization by ligation approach (FIG. 21a), 40 μl ligation mix (as described previously) was added and incubated for 10 min at 37° C. followed by washing and drying. After that the glass slide was stored at 4° C. and ready for PLA.

PLA on Glass Slides

Samples were prepared by diluting antigens to a useful concentration with PLA buffer. Forty μl were added to each reaction chamber and incubated at 37° C. for 1.5 h. Each well was flushed with 1 ml 1×PBS and dried. Next, 40 μl of PLA probe mix containing 5 nM of each proximity probe was added and incubated at 37° C. for another 1.5 h. After that the wells were washed and 40 μl of the nicking mix (1×NEB buffer (New England Biolabs), 0.1 μg/μl purified BSA (New England Biolabs), 0.5 unit of Nb.BtsI (New England Biolabs)) was added and incubated for 30 min at 37° C. After washing, 40 μl ligation mix (1×PCR buffer (Invitrogen), 2.5 mM MgCl$_2$(Invitrogen), 1 unit of T4 DNA ligase (Fermentas), 100 nM of two splint oligonucleotides and 0.08 mM ATP (Fermentas)) was added and incubated at 37° C. for 10 min. Each well was washed before the addition of 40 µl UNG mix (1×PCR buffer (Invitrogen), 2.5 mM $MgCl_2$ (Invitrogen), 1 unit of UNG (Fermentas)). After incubating at 37° C. for 5 min, each well was washed and reconstituted with 40 µl RCA mix (1×phi29 buffer (Fermentas), 0.5 µg/µl purified BSA (New England Biolabs), 0.2 mM dNTPs (Fermentas), 6 units of phi29 (Fermentas)). The RCA reaction was carried out at 37° C. for 60 min.

Readout by Sequencing

Upon 1 h RCA reaction at 37° C., the wells were washed and 40 µl of hybridization mix containing 100 nM sequence primer and 1× hybridization buffer was added. The glass slide was incubated at 37° C. for 30 min. Afterwards each well was equilibrated with 1× incorporation buffer (Illumina). The wells were dried and 40 µl incorporation mix (Illumina) was added and incubated at 55° C. for 10 min. Lastly, each well was washed and dried again. Mounting media was added and the glass slide was covered with coverslip and ready to observe under microscope. The microscopic images were analyzed with BlobFinder and the blobs were enumerated.

Example 3

Unfolding Probes for RNA Detection with Single Molecule Resolution

RNA of interest is targeted by a set of three oligonucleotides and translated into a circular DNA reporter molecule (FIG. 23a). Oligonucleotide probes comprise sequences complementary to the targeted RNA region, flanking hairpin structures which can be unfolded by removing uracil bases by uracil-DNA glycosylase (UNG) and cleaved at the abasic sites by endonuclease, e.g. EndoIV or Fpg. Among the three unfolded probes, one carries an oligonucleotide that can be circularized by hybridisation to a second probe, and the third probe serves as primer for RCA resulting in 1000 copies of the circle DNA after an hour at 37° C. The RCA products then can be visualized by hybridization of fluorescently labelled detection oligonucleotides.

Methods & Materials

Target Recognition by Unfolding Probes 20 nM synthetic DNA template was incubated with 60 nM of three unfolding probes in hybridization buffer (150 mM NaCl, 5 mM EDTA, 1×PBS and 0.05% Tween20). The oligonucleotide mix was then diluted 100 times with hybridization buffer. 50 µl of the diluted mix was spread on a poly L-lysine-coated microscope slide (Sigma-Aldrich) that attached with secure-Seal 8 (Grace Bio-labs) at RT for approximately 15 min. The slide was rinsed in 1×PBS and dried after an ethanol series.

50 µl UNG mix (1×PCR buffer (Invitrogen), 2.5 mM $MgCl_2$ (Invitrogen), 1 unit of UNG (Fermentas), 1 unit of EndoIV (New England Biolabs)) was added to each well. After incubation at 37° C. for 30 min followed by washing and drying, 50 µl ligation mix (1×PCR buffer (Invitrogen), 2.5 mM $MgCl_2$ (Invitrogen). 1 unit of T4 DNA ligase (Fermentas) and 0.08 mM ATP (Fermentas)). The ligation reaction was incubated at 37° C. for 30 min, followed by rinsing in 1×PBS and addition of 50 µl RCA mix (1×phi29 buffer (Fermentas), 0.5 µg/µl purified BSA (New England Biolabs), 0.2 mM dNTPs (Fermentas), 6 units of phi29 (Fermentas)). The RCA reaction was carried out at 37° C. for 60 min.

The RCA products were visualized by hybridization of 10 nM fluorescently labelled probes, incubating at 37° C. for 15 min, followed by rinsing in 1×PBS and ethanol series.

Thereafter slides were spun dry, mounted with approximately 10 µl VectaShield (Immunkemi) and a cover slip and imaged. The microscopic images were analyzed with BlobFinder and the blobs were enumerated.

Example 4

Unfolding Proximity Ligation Assay for Measuring and Imaging Individual Nucleic Acid and Protein Molecules Proximity ligation assays using sets of two or three affinity reagents added together to a biological sample comprising target nucleic acid molecules or protein molecules. Upon coincident target binding the probes are enzymatically "unfolded" to reveal mutually complementary sequences that initiate a series of reactions, i.e. hybridization, ligation, and priming of RCA-localized amplification. The results demonstrate that this provides a rapid and efficient, sensitive multiplex detection of either nucleic acids or proteins in a variety of contexts.

Each probe set consisted of three dual-function reagents, namely uPadlock (a proximity probe comprising a nucleic acid domain that is unfolded to generate two single stranded nucleic acid molecules that are partially hybridised, wherein one nucleic acid strand comprises a middle region that remains hybridised to part of the parent nucleic acid strand attached to the analyte binding domain and wherein said strand may be involved in an intramolecular ligation to produce a circular oligonucleotide), uSplint (a proximity probe comprising a nucleic acid domain that is unfolded to generate a ligation template capable of templating the ligation of the unfolded uPadlock) and uPrimer (a proximity probe comprising a nucleic acid domain that is unfolded to generate a primer capable of amplifying the circularised nucleic acid of the uPadlock) (FIGS. 24a and e). Each one of the reagents has an analyte-binding domain, which serves to recognize target nucleic acid or protein molecules, and one reporter region, which contributes to signal amplifications upon addition of enzymes. The affinity regions are designed to recognize specific target molecules, for example, complementary nucleotide sequences for detection of DNA or RNA molecules or using antibodies for protein detection. The reporter regions are folded hairpin-loop nucleic acid structures, each playing a distinct role within a set of probes. The uPadlock comprises two motifs complementary to the uSplint and one to the uPrimer. The uSplint and uPrimer each include motifs in their hairpin stems that are complementary to the uPadlock, designed so that they can be rendered single-stranded via enzyme digestion after the probes have bound their targets.

After target recognition, followed by enzymatic digestion, all the nucleic acid hairpin structures are induced to unfold. This causes the uPadlock to release one DNA strand whose middle region remains hybridized to the parent strand attached to the affinity reagent. The two ends of the released strand of the padlock probe can now hybridize to an exposed motif of the uSplint, while the unfolded uPrimer basepairs to another segment of the padlock probe (FIG. 24b). Next, the ends of the padlock probe are joined by a DNA ligase (FIG. 24c). The circularized DNA reporter is then amplified by RCA, initiated from the uPrimer. After a one-hour incubation each RCA product comprises up to 1000 concatemeric complements of the circularized probe. This long DNA strand forms a random coil with a diameter of up to one µm, located at the site of binding by the uPrimer (FIG. 24d). RCA products that form can be identified under a fluorescence microscope by various means, for example, via hybridization of fluorescence-labeled detection oligonucleotides, ligation of fluorescence-labeled short DNA tags or polymerase-assisted incorporation of fluorescence-labeled nucleotides to oligonucleotides that hybridize to the RCA products.

Materials and Methods

Designing uPLA Probes

Sequences of uPLA (unfolding proximity ligation assay) probes for DNA and mRNA detection are displayed in Table 1. Affinity regions for targeting mRNA were designed to have hybridizing segments with a Tm of approximately 60° C., and with an optimal size around 20 nt, minimal unwanted secondary structure, and minimal similarity to irrelevant genomic sequences. The sequences were initially designed using Primer3 (http://frodo.wi.mit.edu/primer3/), and "blasted" against the human genome (http://genome.ucsc.edu/cgi-bin/hgBlat). The reporter regions of the uPLA probes for protein detection are displayed in Table 2. The oligonucleotides were modified with thiol groups at one of the ends for conjugation to antibodies via the bifunctional linker Sulfo-SMCC (Table 3). All DNA probes were purchased from Integrated DNA Technologies (IDT) and antibodies were purchased from R&D Systems.

Probing Synthetic DNA with uPLA Probes

Fifty µl 20 µM biotinylated synthetic DNA template was added to a streptavidin-coated Codelink slide (SurModics) in 1×PBS and incubated at 37° C. for 15 min. After two washes in 1×PBS with 0.05% Tween 20, a 50 µl probe mix containing 5 pmol of each uPLA probe in 1×PBS was added to the slide for incubation at 37° C. for 30 min. After washing twice in 1×PBS with 0.05% Tween 20, a 50 µl uPLA probe mix containing 5 U Uracil-DNA glycosylase (UNG) (Fermentas), 5 U EndoIV (Fermentas), 1 µg/µl BSA in 1× unfolding buffer (MutY buffer) was added to the cells and incubated at 37° C. for 30 min. Then 50 µl ligation mix (1×PCR buffer (Invitrogen), 2.5 mM MgCl2 (Invitrogen). 1 unit of T4 DNA ligase (Fermentas) and 0.08 mM ATP (Fermentas)) was added. The ligation reaction was incubated at 37° C. for 30 min, followed by rinsing in 1×PBS and addition of 50 µl RCA mix (1×phi29 buffer (Fermentas), 0.5 µg/µl purified BSA (New England Biolabs), 0.2 mM dNTPs (Fermentas), 6 units of phi29 (Fermentas)). The RCA reaction was carried out at 37° C. for 60 min. Next, the RCA products were visualized by hybridization with 10 nM fluorescence labeled probes by incubation at 37° C. for 15 min, followed by rinsing in 1×PBS and an ethanol series. Thereafter slides were spun dry, mounted with ~10 µl VectaShield (Immunkemi) and a cover slip and imaged.

Cell Culture and Preparation

The cell lines K562, BV173 and SKOV3 were cultured in RPMI culture medium (Sigma), supplemented with 2 mM L-glutamin (Gibco), 10% FBS (Sigma) and 1× penicillin-streptomycin (PEST, Sigma). BJhTERT cells were cultured in MEM without phenol red and L-glutamine (Gibco), supplemented with 10% FBS (Sigma), 1× nonessential amino acids (Gibco) and 1×PEST (Sigma). BV173 cells were attached on Supefrost Plus Gold slides (Thermo Scientific) at 1500 g for 5 min. K562, SKOV3 and BJhTERT cells were seeded on the slides and allowed to attach and expand to desired confluence. Cells were then fixed in 3% (w/v) paraformaldehyde (Sigma) in PBS for 30 min at room temperature. After fixation, slides were washed twice in DEPC-treated PBS and stored in 70% ethanol at 4° C. for at least 8 hours before being used.

Probing mRNA with uPLA Probes

Fixed cells, grown on slides were incubated with 50 µl 2×SSC (300 mM NaCl, 30 mM Na-citrate), 50% formamide (Sigma), 5 U RNase Inhibitor (Fermentas) at 70° C. for 10 min. Twenty pmol of each probe were heated at 95° C. for 90 s and then allowed to cool to room temperature by snap cooling in 10 µl 400 mM NaCl 50 mM NaHPO4 on the benchtop for 30 min. A 50 µl probes mix containing 2×SSC, 5 U RNase Inhibitor, 0.5 µg/µl salmon sperm DNA (Invitrogen), 10% formamide, 0.2 µg/µl BSA (NEB), 5% dextran sulfate (Invitrogen) and 5 pmol of each uPLA probe was then added to the cells and incubated at 37° C. for 3-4 h. After washing twice with 50 µl 2×SSC, 10% formamide, a 50 µl unfolding mix containing 5 U UNG (Fermentas), 5 U EndoIV (Fermentas), 5 U RNase inhibitor, 1 µg/µl BSA in 1× unfolding buffer (MutY buffer) was added to the cells and incubated at 37° C. for 30 min. After washing twice with 50 µl 1×DEPC-PBS, 0.05% Tween20, a 50 µl ligation mix containing 12.5 U Ampligase (Epicenter), 5 U RNase Inhibitor, 20% Formamide, 50 mM KCl, 0.2 µg/µl BSA in 1× Ampligase buffer (Epicenter) was added to the cells and incubated at 45° C. for 45 min. The RCA was carried out thereafter by adding 50 µl RCA mix containing 25 U phi29 DNA polymerase (Fermentas), 5 U RNase Inhibitor, 5% glycerol (Invitrogen), 250 nM dNTP (Fermentas), 0.2 µg/µl BSA in 1×phi29 buffer (Fermentas) and incubating at 37° C. for 1 h. After washing twice with 50 µl 1×DEPC-PBS, 0.05% Tween20, a 50 µl detection mix containing 5 pmol detection oligonucleotides in 2×SSC, 20% formamide was added to the cells and incubated at 37° C. for 20 min, followed by washing twice in 50 µl 1×DEPC-PBS, 0.05% Tween20 and drying in ethanol series. Thereafter slides were spun dry, mounted with ~20 µl VectaShield (Immunkemi), containing 100 ng/ml DAPI, and a 25×40 mm cover slip and imaged.

Antibody Immobilization on Glass Slides

Amine-modified oligonucleotides (Biomers) were printed on TRIDIA™ codelink slides (SurModics). Each slide was printed with 14 sub-arrays of 20×20 features. Secure-Seal 16 (Grace Bio-labs) was attached to the slides prior to use. Forty µl of 50 nM capture conjugates (antibody conjugated to an oligonucleotide capable of hybridising to the amine-modified oligonucleotides printed on the slides) were added to each reaction chamber and incubated over-night at 4° C. in 1×PBS, 0.1% BSA (Sigma). Next, each well was gently flushed with 1 ml 1×PBS and dried.

Probing Protein with uPLA Probes

Samples were prepared by diluting recombinant proteins, GDF15 (957-GD-025, R&D), Mouse IgG (15381, Sigma) and PSA (1344-SE, R&D) individually or all together at 1 nM with PLA buffer (0.1% BSA (Sigma), 5 mM EDTA, 100 nM goat IgG (Sigma), 10 µg/µl salmon sperm DNA (Invitrogen), 0.05% Tween 20 (Sigma) and 1×PBS). Forty µl were added to each reaction chamber and incubated at 37° C. for 1.5 h. Each well was flushed with 1 ml 1×PBS and dried. Next, 40 µl of PLA probe mix containing 5 nM of three pairs of probes in PLA buffer was added and incubated at 37° C. for another 1.5 h. After that the wells were washed and the probes were digested, ligated and amplified according to the steps described in uPLA probes for detection of synthetic DNA.

In Situ Readout Via Sequencing of RCA Products

Upon a 1 h RCA reaction at 37° C., the wells were washed and 40 µl of hybridization mix containing 100 nM sequence primer and 1× hybridization buffer was added. The glass slide was incubated at 37° C. for 30 min. Afterwards each well was equilibrated with 1× incorporation buffer (Illumina). The wells were dried and 40 µl incorporation mix (Illumina) was added and incubated at 55° C. for 10 min. Lastly, each well was washed and dried again. Mounting media was added and the glass slide was covered with a coverslip, followed by observation under microscope.

Results

Unfolding PLA probes were targeted to synthetic DNA template molecules that were immobilized on a glass slide. The occurrence of detectable fluorescent spots clearly depended on the joint presence of templates and on the enzymes required for the unfolding reactions (FIG. 24f-h). To assess the relative advantages of using three rather than two probes, we also designed a set where coincident detection by two probes sufficed to produce signals. In these experiments the same uPadlock was used together with another reagent, which after unfolding could serve both as splint for ligation and primer for RCA. The results of this experiment reveal an enhanced signal to noise ratio when three rather than two probes were used.

Next, we tested our probes in biological systems by directly targeting individual mRNA molecules in situ. We first deigned a set of three probes specific for the cancer-related transcripts HER2, and applied these in two cell lines; the human ovarian carcinoma cell line SKOV3 and TERT-immortalized fibroblasts (BJhTERT). Signals (circled) were observed in the SKOV3 cells (FIG. 25a) but not in BJhTERT cells (FIG. 25b).

To further assess the specificity of our probes, we targeted a variant of the BCR-ABL fusion transcripts referred to as b3a2 present in the human erythromyeloblastoid leukemia cell line K562. The human leukemia cell line BV173 express another variant of a BCR-ABL fusion transcript called b2a2. We designed a uPrimer and a uSplint to target two common regions in both fusion variants, and a uPadlock specific for the unique breakpoint in b3a2, which is absent in transcript b2a2. As expected, detectable levels of signals (circled) were observed in K562 (FIG. 25c) whereas no signals were observed in BVI73 (FIG. 25d).

The uPLA probes lend themselves for parallel detection of single molecules representing several different targets. We developed an assay for simultaneous analysis of three purified proteins: growth differentiation factor (GDF)-15, prostate-specific antigen (PSA), and mouse immunoglobulins (IgG), diluted in buffer. We designed three sets of probes that all included 6-nt tag sequences in the reporter regions of the uPadlock probes. For each set of probes, the reporter regions of uPadlock and uSplint probes were covalently conjugated to different aliquots of the same batch of polyclonal antibodies specific for the targeted protein. Yet other aliquots of the polyclonal antibodies were conjugated to oligonucleotides that were immobilized on a glass slide, and the affinity regions of the uPrimers were hybridized to these immobilized DNA strands.

Proteins were first captured by the antibodies with the attached uPrimer immobilized on the slide. After washes the uPadlock and uSplint probes were added, followed by renewed washes. Next the probes were unfolded by enzymatic digestion, with subsequent circularization and RCA amplification of padlock probes from the immobilized primers. Finally, the RCA products representing detected protein molecules were identified by decoding the first nucleotides of the tag sequences, using the principle of DNA sequencing by synthesis (FIG. 26). The experiment demonstrated the feasibility of detecting individual protein molecules by in situ sequencing of individual RCA products, a technology that could be used to distinguish vast amounts of detected proteins.

TABLE 1

| SEQ ID NO: | Name | SEQUENCES 5'-3' | 3' modification | 5' modification |
|---|---|---|---|---|
| 15 | Synthetic DNA template | TCTCTATGAGTCTCC GGGGCTCTATTCTCT CTCTCTCTCTGCAGA GTTCAAAAGCCCTTC AGTCTCTCTCTCT CTTTGAGCCTCAGGG TCTGAGTTCT | Biotin | |
| 16 | BCRABL uPadlock | CGACGCTCTTCCGAT CTTGGTCATGTTGAT CGGCAGTGATGCACT CTTTCCCTACAUCAC TGCCGATCAACATCT CTCCTGAAGGGCTTT TGAACTCTGC | | Phosphate |
| 17 | BCRABL uPrimer | ACTCAGACCCTGAGG CTCAACTCTCTCTCT CTCTCTCTCTGACCA AGATCGCTCTCGAUC UUGGUCA | | |
| 18 | BCRABL uSplint | CCCTACACGACGCUC UUCTCTAAGAGCGTC GTGTAGGGAAATCTC TCTCTCTCTCTCT CATAGAGCCCCGGAG ACTCAT | | |
| 19 | HER2 uPadlock | CGACGCTCTTCCGAT CTTGGTCATGTTGAT CGGCAGTGATGCACT CTTTCCCTACAUCAC TGCCGATCAACATCT CTCCTCCTGGATATC CTGCAGGA | | Phosphate |
| 20 | HER2 uPrimer | GACCTGCCTCACTTG GTTGTCTUCTCTCTC TCTCTCTCTGACCAA GATCGCTCTCGAUCU UGGUCA | | |
| 21 | HER2 uSplint | CCCTACACGACGCUC UUCTCTAAGAGCGTC GTGTAGGGAAATCTC TCTCTCTCTCTCT CGCAGGTAGGTGAGT TCCAGG | | |

TABLE 2

| SEQ ID NO: | Name | SEQUENCES 5'-3' | 3' modification | 5' modification |
|---|---|---|---|---|
| 22 | uPadlock 1 | CGACGCTCTTCCGAT CTGATCTGTCGGCAG TGACACTCTTTCCCT ACAUUCACTGCCGAC AGATCCGTTTTTT | Thiol | Phosphate |
| 23 | uPadlock 2 | CGACGCTCTTCCGAT CTATTGGCTCGGCAG TGACACTCTTTCCCT ACAUUCACTGCCGAG CCAATCGTTTTTT | Thiol | Phosphate |
| 24 | uPadlock 3 | CGACGCTCTTCCGAT CTTGGTCATCGGCAG TGACACTCTTTCCCT ACAUUCACTGCCGAT GACCACGTTTTTT | Thiol | Phosphate |

TABLE 2-continued

| SEQ ID NO: | Name | SEQUENCES 5'-3' | 3' modification | 5' modification |
|---|---|---|---|---|
| 25 | uSplint | TACACGACGCUUTTT AGCGTCGTGTAGGGT CTCTCTCTCTCTCTC TCTC | Thiol | |
| 26 | uPrimer | TTTTTTTTTCAAGC AGAAGACGGCATACG ATTTTTTTTTAGAT CGGUUUCCGAUCU | | Thiol |

TABLE 3

| Antibody | Catalogue Number |
|---|---|
| Human GDF-15 Affinity Purified Polyclonal Ab, Goat IgG | AF957 |
| Human Kallikrein 3/PSA Affinity Purified Polyclonal Ab, Goat IgG | AF1344 |
| Goat Anti-Mouse IgG Unlabeled Affinity Purified Polyclonal Ab, Goat IgG | AF007 |

The invention claimed is:

1. An unfolding proximity probe comprising an analyte-binding domain coupled to a nucleic acid domain, wherein said nucleic acid domain comprises:
   (i) at least one region of complementarity to a target sequence, wherein said target sequence comprises part of a ligation template for the probe and is not the analyte or any part of the analyte; and
   (ii) regions of self-complementarity forming a hairpin structure present in the probe in the absence of the analyte, wherein said hairpin structure has a stem region and a loop region and inhibits said at least one region of complementarity from hybridizing to the target sequence;
   wherein the hairpin structure comprises a cleavable site which is cleavable to open the hairpin structure to result in a partially double stranded nucleic acid domain which comprises one strand having free 5' and 3' ends and hybridized to another strand in the stem region, thereby to release said at least one region of complementarity of the nucleic acid domain and enable it to hybridize to the target sequence.

2. The unfolding proximity probe of claim 1, wherein the analyte-binding domain is other than a nucleic acid.

3. The unfolding proximity probe of claim 1, wherein
   (i) the site at which cleavage occurs is located in the hairpin structure of the nucleic acid domain; and/or
   (ii) said cleavage is enzymatic cleavage; and/or
   (iii) the hairpin structure comprises a cleavage recognition site that is recognised by one or more enzymes capable of cleaving nucleic acid molecules; and/or
   (iv) said one or more enzymes is a nickase or a restriction endonuclease; and/or
   (v) the nickase enzyme is removed from the assay or inactivated following unfolding of the nucleic acid domain of the proximity probe.

4. The unfolding proximity probe of claim 1, wherein upon release, the at least one region of complementarity is capable of hybridizing to the target sequence comprising said ligation template in the form of a nucleic acid domain of a proximity probe.

5. The unfolding proximity probe of claim 1, wherein upon release, the at least one region of complementarity is capable of hybridizing to the target sequence comprising said ligation template in the form of a free oligonucleotide.

6. The unfolding proximity probe of claim 1, wherein the free 5' and 3' ends of the partially double stranded nucleic acid domain are ligatable directly or indirectly to form a circular oligonucleotide.

7. The unfolding proximity probe of claim 1, wherein the 5' end of the partially double stranded nucleic acid domain are ligatable directly or indirectly to the 3' end of the nucleic acid domain of a further proximity probe.

8. The unfolding proximity probe of claim 1, wherein the 3' end of the partially double stranded nucleic acid domain are ligatable directly or indirectly to the 5' end of the nucleic acid domain of a further proximity probe.

9. The unfolding proximity probe of claim 6, wherein the free 5' and 3' ends of the partially double stranded nucleic acid domain hybridize to their respective targets such that
  (i) the free 5' and 3' ends hybridise to one or more ligation templates which act to template the ligation of the free ends to each other directly or indirectly;
  (ii) the free 5' and 3' ends hybridise to the ligation template(s) directly adjacent to each other; or
  (iii) the free 5' and 3' ends hybridise to the ligation template with a space in between and optionally, (iiia) wherein the space in between the ends is filled by a gap oligonucleotide such that each ligatable end is ligated to one end of the gap oligonucleotide, or (iiib) wherein prior to the ligation reaction the space in between the ends of the ligatable nucleic acid domain(s) is filled-in by extension of the free 3' end using the ligation template as an extension template.

10. A sample comprising an analyte, a target sequence, and an unfolding proximity probe, wherein:
  the target sequence comprises part of a ligation template for the unfolding proximity probe and is not the analyte or any part of the analyte; and
  the unfolding proximity probe comprises an analyte-binding domain coupled to a nucleic acid domain, wherein said nucleic acid domain comprises:
    (i) at least one region of complementarity to the target sequence; and
    (ii) regions of self-complementarity forming a hairpin structure present in the probe in the absence of the analyte, wherein said hairpin structure has a stem region and a loop region and inhibits said at least one region of complementarity from hybridizing to the target sequence;
  wherein the hairpin structure comprises a cleavable site which is cleavable to open the hairpin structure to result in a partially double stranded nucleic acid domain which comprises one strand having free 5' and 3' ends and hybridized to another strand in the stem region, thereby to release said at least one region of complementarity of the nucleic acid domain and enable it to hybridize to the target sequence.

* * * * *

SEQUENCE LISTING

<160> NUMBER OF SEQ ID NOS: 26

<210> SEQ ID NO 1
<211> LENGTH: 51
<212> TYPE: DNA
<213> ORGANISM: Artificial sequence
<220> FEATURE:
<223> OTHER INFORMATION: PLA oligonucleotide
<220> FEATURE:
<221> NAME/KEY: misc_feature
<222> LOCATION: (1)..(1)
<223> OTHER INFORMATION: Thiol

<400> SEQUENCE: 1
gtcttaacta ttagcgatac ggtctcgcag atcgctgaca gaactagaca c            51

<210> SEQ ID NO 2
<211> LENGTH: 64
<212> TYPE: DNA
<213> ORGANISM: Artificial sequence
<220> FEATURE:
<223> OTHER INFORMATION: "First" proximity probe

<400> SEQUENCE: 2
gcctcccaaa gtgctgggat tacaggaaaa aacatggatg ttcttgacat ggcaatgacg   60
ctaa                                                                64

<210> SEQ ID NO 3
<211> LENGTH: 70
<212> TYPE: DNA
<213> ORGANISM: Artificial sequence
<220> FEATURE:
<223> OTHER INFORMATION: Padlock probe
<220> FEATURE:
<221> NAME/KEY: misc_feature
<222> LOCATION: (1)..(1)
<223> OTHER INFORMATION: Phosphate

<400> SEQUENCE: 3
agcgatctgc gagacagtga atgcgagtcc gtctaagaga gtacagcagc cgtcttagcg   60
tcattgccat                                                          70

<210> SEQ ID NO 4
<211> LENGTH: 34
<212> TYPE: DNA
<213> ORGANISM: Artificial sequence
<220> FEATURE:
<223> OTHER INFORMATION: Gap oligonucleotide
<220> FEATURE:
<221> NAME/KEY: misc_feature

```
<222> LOCATION: (1)..(1)
<223> OTHER INFORMATION: Phosphate

<400> SEQUENCE: 4
gtcaagaaca tccatgaaag tgtctagttc tgtc                                34

<210> SEQ ID NO 5
<211> LENGTH: 20
<212> TYPE: DNA
<213> ORGANISM: Artificial sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: Alexa fluor 555

<400> SEQUENCE: 5
cagtgaatgc gagtccgtct                                                20

<210> SEQ ID NO 6
<211> LENGTH: 75
<212> TYPE: DNA
<213> ORGANISM: Artificial sequence
<220> FEATURE:
<223> OTHER INFORMATION: Padlock oligonucleotide
<220> FEATURE:
<221> NAME/KEY: misc_feature
<222> LOCATION: (1)..(1)
<223> OTHER INFORMATION: Phosphate

<400> SEQUENCE: 6
tgtcaagaac atccatgtca gtgaatgcga gtccgtctaa gagagtagta cagcagccgt   60
ttagcgtcat tgcca                                                    75

<210> SEQ ID NO 7
<211> LENGTH: 37
<212> TYPE: DNA
<213> ORGANISM: Artificial sequence
<220> FEATURE:
<223> OTHER INFORMATION: GenomeTemplate oligonucleotide 1
<220> FEATURE:
<221> NAME/KEY: misc_feature
<222> LOCATION: (1)..(1)
<223> OTHER INFORMATION: Phosphate

<400> SEQUENCE: 7
ctgggattac aggaaaaaaa gagtgtctag ttctgtc                             37

<210> SEQ ID NO 8
<211> LENGTH: 59
<212> TYPE: DNA
<213> ORGANISM: Artificial sequence
<220> FEATURE:
<223> OTHER INFORMATION: GenomeTemplate oligonucleotide 2
<220> FEATURE:
<221> NAME/KEY: misc_feature
<222> LOCATION: (1)..(1)
<223> OTHER INFORMATION: Phosphate

<400> SEQUENCE: 8
cgctaatagt taagacgctc agtgaatgcg agtccgtcta aaaaaagccg cccaaagtg    59

<210> SEQ ID NO 9
<211> LENGTH: 20
<212> TYPE: DNA
<213> ORGANISM: Artificial sequence
<220> FEATURE:
```

```
<223> OTHER INFORMATION: Additional gap oligonucleotide
<220> FEATURE:
<221> NAME/KEY: misc_feature
<222> LOCATION: (1)..(1)
<223> OTHER INFORMATION: Phosphate

<400> SEQUENCE: 9
agcgatctgc gagaccgtat                                                    20

<210> SEQ ID NO 10
<211> LENGTH: 20
<212> TYPE: DNA
<213> ORGANISM: Artificial sequence
<220> FEATURE:
<223> OTHER INFORMATION: Additional detection oligonucleotide
<220> FEATURE:
<221> NAME/KEY: misc_feature
<222> LOCATION: (1)..(1)
<223> OTHER INFORMATION: Cy5

<400> SEQUENCE: 10
agcgatctgc gagaccgtat                                                    20

<210> SEQ ID NO 11
<211> LENGTH: 83
<212> TYPE: DNA
<213> ORGANISM: Artificial sequence
<220> FEATURE:
<223> OTHER INFORMATION: Horn probe part A
<220> FEATURE:
<221> NAME/KEY: misc_feature
<222> LOCATION: (1)..(1)
<223> OTHER INFORMATION: Phosphate

<400> SEQUENCE: 11
ctgggattac aggaaaaaaa gagtgtctag ttctgtcuta aaaaaataag acagaacuag        60
acacuctaaa aaaagcgtcu taa                                                83

<210> SEQ ID NO 12
<211> LENGTH: 78
<212> TYPE: DNA
<213> ORGANISM: Artificial sequence
<220> FEATURE:
<223> OTHER INFORMATION: Horn probe part B
<220> FEATURE:
<221> NAME/KEY: misc_feature
<222> LOCATION: (1)..(1)
<223> OTHER INFORMATION: Phosphate

<400> SEQUENCE: 12
ctautagcga caaaaaaguc gctaatagtt aagacgctca gtgaatgcga gtccgtctaa        60
aaaaagccgc ccaaagtg                                                      78

<210> SEQ ID NO 13
<211> LENGTH: 26
<212> TYPE: DNA
<213> ORGANISM: Homo sapiens

<400> SEQUENCE: 13
cctgtaatcc cagcactttg ggaggc                                             26

<210> SEQ ID NO 14
<211> LENGTH: 25
<212> TYPE: DNA
<213> ORGANISM: Mus musculus

<400> SEQUENCE: 14
```
cctttaatcc cagcactcgg gaggc    25

<210> SEQ ID NO 15
<211> LENGTH: 100
<212> TYPE: DNA
<213> ORGANISM: Artificial sequence
<220> FEATURE:
<223> OTHER INFORMATION: Synthetic DNA template
<220> FEATURE:
<221> NAME/KEY: misc_feature
<222> LOCATION: (100)..(100)
<223> OTHER INFORMATION: Biotin

<400> SEQUENCE: 15
tctctatgag tctccggggc tctattctct ctctctctct gcagagttca aaagcccttc    60
agtctctctc tctctctttg agcctcaggg tctgagttct    100

<210> SEQ ID NO 16
<211> LENGTH: 100
<212> TYPE: DNA
<213> ORGANISM: Artificial sequence
<220> FEATURE:
<223> OTHER INFORMATION: BCRABL uPadlock
<220> FEATURE:
<221> NAME/KEY: misc_feature
<222> LOCATION: (1)..(1)
<223> OTHER INFORMATION: Phosphate

<400> SEQUENCE: 16
cgacgctctt ccgatcttgg tcatgttgat cggcagtgat gcactctttc cctacaucac    60
tgccgatcaa catctctcct gaagggcttt tgaactctgc    100

<210> SEQ ID NO 17
<211> LENGTH: 67
<212> TYPE: DNA
<213> ORGANISM: Artificial sequence
<220> FEATURE:
<223> OTHER INFORMATION: BCRABL uPrimer

<400> SEQUENCE: 17
actcagaccc tgaggctcaa ctctctctct ctctctctct gaccaagatc gctctcgauc    60
uugguca    67

<210> SEQ ID NO 18
<211> LENGTH: 81
<212> TYPE: DNA
<213> ORGANISM: Artificial sequence
<220> FEATURE:
<223> OTHER INFORMATION: BCRABL uSplint

<400> SEQUENCE: 18
cccuacacga cgcucuuctc taagagcgtc gtgtagggaa atctctctct ctctctctct    60
catagagccc cggagactca t    81

<210> SEQ ID NO 19
<211> LENGTH: 98
<212> TYPE: DNA
<213> ORGANISM: Artificial sequence
<220> FEATURE:
<223> OTHER INFORMATION: HER2 uPadlock
<220> FEATURE:
<221> NAME/KEY: misc_feature
<222> LOCATION: (1)..(1)
<223> OTHER INFORMATION: Phosphate

```
<400> SEQUENCE: 19
cgacgctctt ccgatcttgg tcatgttgat cggcagtgat gcactctttc cctacaucac     60
tgccgatcaa catctctcct cctggatatc ctgcagga                             98

<210> SEQ ID NO 20
<211> LENGTH: 67
<212> TYPE: DNA
<213> ORGANISM: Artificial sequence
<220> FEATURE:
<223> OTHER INFORMATION: HER2 uPrimer

<400> SEQUENCE: 20
gacctgcctc acttggttgt ctctctctct ctctctctct gaccaagatc gctctcgauc     60
uugguca                                                               67

<210> SEQ ID NO 21
<211> LENGTH: 81
<212> TYPE: DNA
<213> ORGANISM: Artificial sequence
<220> FEATURE:
<223> OTHER INFORMATION: HER2 uSplint

<400> SEQUENCE: 21
cccuacacga cgcucuuctc taagagcgtc gtgtagggaa atctctctct ctctctctct     60
cgcaggtagg tgagttccag g                                               81

<210> SEQ ID NO 22
<211> LENGTH: 73
<212> TYPE: DNA
<213> ORGANISM: Artificial sequence
<220> FEATURE:
<223> OTHER INFORMATION: uPadlock 1
<220> FEATURE:
<221> NAME/KEY: misc_feature
<222> LOCATION: (1)..(1)
<223> OTHER INFORMATION: Phosphate
<220> FEATURE:
<221> NAME/KEY: misc_feature
<222> LOCATION: (73)..(73)
<223> OTHER INFORMATION: Thiol

<400> SEQUENCE: 22
cgacgctctt ccgatctgat ctgtcggcag tgacactctt tccctacauu cactgccgac     60
agatccgttt ttt                                                        73

<210> SEQ ID NO 23
<211> LENGTH: 73
<212> TYPE: DNA
<213> ORGANISM: Artificial sequence
<220> FEATURE:
<223> OTHER INFORMATION: uPadlock 2
<220> FEATURE:
<221> NAME/KEY: misc_feature
<222> LOCATION: (1)..(1)
<223> OTHER INFORMATION: Phosphate
<220> FEATURE:
<221> NAME/KEY: misc_feature
<222> LOCATION: (73)..(73)
<223> OTHER INFORMATION: Thiol

<400> SEQUENCE: 23
cgacgctctt ccgatctatt ggctcggcag tgacactctt tccctacauu cactgccgag     60
ccaatcgttt ttt                                                        73
```

```
<210> SEQ ID NO 24
<211> LENGTH: 73
<212> TYPE: DNA
<213> ORGANISM: Artificial sequence
<220> FEATURE:
<223> OTHER INFORMATION: uPadlock 3
<220> FEATURE:
<221> NAME/KEY: misc_feature
<222> LOCATION: (1)..(1)
<223> OTHER INFORMATION: Phosphate
<220> FEATURE:
<221> NAME/KEY: misc_feature
<222> LOCATION: (73)..(73)
<223> OTHER INFORMATION: Thiol

<400> SEQUENCE: 24
cgacgctctt ccgatcttgg tcatcggcag tgacactctt tccctacauu cactgccgat      60
gaccacgttt ttt                                                         73

<210> SEQ ID NO 25
<211> LENGTH: 49
<212> TYPE: DNA
<213> ORGANISM: Artificial sequence
<220> FEATURE:
<223> OTHER INFORMATION: uSplint
<220> FEATURE:
<221> NAME/KEY: misc_feature
<222> LOCATION: (49)..(49)
<223> OTHER INFORMATION: Thiol

<400> SEQUENCE: 25
tacacgacgc uutttagcgt cgtgtagggt ctctctctct ctctctctc                  49

<210> SEQ ID NO 26
<211> LENGTH: 58
<212> TYPE: DNA
<213> ORGANISM: Artificial sequence
<220> FEATURE:
<223> OTHER INFORMATION: uPrimer
<220> FEATURE:
<221> NAME/KEY: misc_feature
<222> LOCATION: (1)..(1)
<223> OTHER INFORMATION: Thiol

<400> SEQUENCE: 26 ttttttttt caagcagaag acggcatacg attttttttt tagatcgguu uccgaucu         58
```